United States Patent
Inaba et al.

(10) Patent No.: US 7,163,952 B2
(45) Date of Patent: Jan. 16, 2007

(54) AZOLE COMPOUND AND MEDICINAL USE THEREOF

(75) Inventors: Takashi Inaba, Takatsuki (JP); Tomoyuki Ikemoto, Takatsuki (JP); Shohei Sakata, Takatsuki (JP); Hiroshi Maegawa, Kusatsu (JP); Atsunori Kashiwagi, Ohtsu (JP)

(73) Assignee: Japan Tobacco Inc., Tokyo (JP)

( * ) Notice: Subject to any disclaimer, the term of this patent is extended or adjusted under 35 U.S.C. 154(b) by 273 days.

(21) Appl. No.: 10/497,492

(22) PCT Filed: Dec. 3, 2002

(86) PCT No.: PCT/JP02/12673

§ 371 (c)(1),
(2), (4) Date: Oct. 29, 2004

(87) PCT Pub. No.: WO03/048140

PCT Pub. Date: Jun. 12, 2003

(65) Prior Publication Data

US 2005/0065196 A1 Mar. 24, 2005

(30) Foreign Application Priority Data

Dec. 3, 2001 (JP) .............................. 2001-368567

(51) Int. Cl.
*A61K 31/425* (2006.01)
*A61K 31/42* (2006.01)
*A61K 31/535* (2006.01)
*C07D 401/00* (2006.01)
*C07D 415/00* (2006.01)

(52) U.S. Cl. ...................... 514/370; 514/371; 514/377; 514/236.8; 514/254.02; 548/194; 548/201; 548/234; 546/209; 544/133

(58) Field of Classification Search ................ 514/370, 514/371, 377, 236.8, 254.02; 548/194, 201, 548/234; 546/209; 544/133
See application file for complete search history.

(56) References Cited

U.S. PATENT DOCUMENTS

| | | | |
|---|---|---|---|
| 5,296,495 A | 3/1994 | Matsuo et al. | |
| 5,643,932 A | 7/1997 | Chihiro et al. | |
| 5,753,687 A | 5/1998 | Mjalli et al. | |
| 5,770,620 A | 6/1998 | Mjalli et al. | |
| 5,952,356 A | 9/1999 | Ikeda et al. | |
| 6,001,867 A | 12/1999 | Wrobel et al. | |
| 6,011,048 A | 1/2000 | Mathvink et al. | |
| 6,057,316 A | 5/2000 | Wrobel et al. | |
| 6,063,815 A | 5/2000 | Dollings | |
| 6,080,772 A | 6/2000 | Tang et al. | |
| 6,103,708 A | 8/2000 | Dollings et al. | |
| 6,110,962 A | 8/2000 | Wrobel et al. | |
| 6,110,963 A | 8/2000 | Malamas | |
| 6,329,539 B1 | 12/2001 | Sato et al. | |
| 6,344,470 B1 | 2/2002 | Fontaine et al. | |
| 6,395,786 B1 | 5/2002 | Sato et al. | |
| 6,939,629 B1 * | 9/2005 | Katagiri et al. | 429/12 |
| 6,960,606 B1 | 11/2005 | Uckun et al. | 514/371 |
| 7,037,929 B1 * | 5/2006 | Pevarello et al. | 514/371 |
| 7,053,089 B1 * | 5/2006 | Claiborne et al. | 514/252.03 |
| 7,056,939 B1 * | 6/2006 | Berg et al. | 514/371 |
| 7,087,623 B1 * | 8/2006 | Cuny et al. | 514/326 |
| 7,094,794 B1 * | 8/2006 | Petry et al. | 514/370 |
| 7,105,551 B1 * | 9/2006 | Cadilla et al. | 514/365 |
| 7,109,202 B1 * | 9/2006 | Press et al. | 514/255.05 |
| 2002/0137740 A1 | 9/2002 | Fontaine et al. | |
| 2004/0132788 A1 | 7/2004 | Chabrier De Lassauniere et al. | |
| 2005/0038087 A1 | 2/2005 | Chabrier De Lassauniere et al. | |
| 2006/0122181 A1 | 6/2006 | Ikemoto et al. | |

FOREIGN PATENT DOCUMENTS

| | | |
|---|---|---|
| JP | 05-202040 A | 8/1993 |
| JP | 09-67271 A | 3/1997 |
| JP | 11-508919 T | 8/1999 |
| JP | 2000-504039 | 4/2000 |

(Continued)

OTHER PUBLICATIONS

Elchebly et al., *Science*, 283(5407):1544-1548 (Mar. 5, 1999).
Maegawa et al., *J. Biol. Chem.*, 270(13): 7724-7730 (Mar. 31, 1995).
Obata et al., *J. Biochemistry*, 123(5): 813-820 (1998).

*Primary Examiner*—Deborah C. Lambkin
(74) *Attorney, Agent, or Firm*—Leydig, Voit & Mayer, Ltd

(57) ABSTRACT

The present invention relates to an azole compound represented by the formula [I]

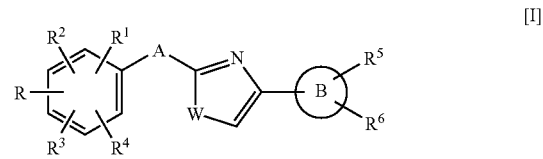

wherein W is S or O; R is —$COOR^7$, —$X^1$-$A^1$-$COOR^7$ ($R^7$ is H, alkyl) or tetrazolyl; $R^1$, $R^2$, $R^3$ and $R^4$ are H and the like; A is —$(CH_2)_m$—X— (X is —$N(R^8)$—, —$C(R^9)(R^{10})$—, —CO— or —CO—$N(R^8)$—); B is aryl or aromatic heterocyclic group; $R^5$ is H and the like; $R^6$ is —$(Y)_{s1}$-$(A^2)_s$-Z (Y is —O—, —$S(O)_t$—, —$N(R^{13})$—, —$N(R^{14})$—CO—, —$N(R^{14})$—$SO_2$—, —$SO_2$—$N(R^{14})$— and the like, $A^2$ is alkylene, and Z is cycloalkyl, aryl, aromatic heterocyclic group, indanyl, piperazinyl, a prodrug thereof or a pharmaceutically acceptable salt thereof. The compound [I] of the present invention has a protein tyrosine phosphatase 1B inhibitory activity, and is useful as a therapeutic agent for diabetes, a therapeutic drug for diabetic complications or a therapeutic drug for hyperlipidemia.

54 Claims, No Drawings

FOREIGN PATENT DOCUMENTS

| | | |
|---|---|---|
| JP | 2000-302680 A | 10/2000 |
| JP | 2002-114768 A | 4/2002 |
| JP | 2002-514633 A | 5/2002 |
| JP | 2003-511416 A | 3/2003 |
| JP | 2003-231679 A | 8/2003 |
| WO | WO 94/08982 A1 | 4/1994 |
| WO | WO 97/30053 A1 | 8/1997 |
| WO | WO 98/27092 A1 | 6/1998 |
| WO | WO 98/28264 A1 | 7/1998 |
| WO | WO 99/21555 A2 | 5/1999 |
| WO | WO 99/58511 | 11/1999 |
| WO | WO 99/58514 A1 | 11/1999 |
| WO | WO 99/58518 A2 | 11/1999 |
| WO | WO 99/58518 A3 | 11/1999 |
| WO | WO 99/58520 A1 | 11/1999 |
| WO | WO 99/58521 A1 | 11/1999 |
| WO | WO 99/58522 A1 | 11/1999 |
| WO | WO 99/61419 A1 | 12/1999 |
| WO | WO 99/61435 A1 | 12/1999 |
| WO | WO 00/17211 A1 | 3/2000 |
| WO | WO 00/45635 A1 | 8/2000 |
| WO | WO 01/26656 A2 | 4/2001 |
| WO | WO 02/34711 A1 | 5/2002 |
| WO | WO 02/39997 A2 | 5/2002 |
| WO | WO 02/39997 A3 | 5/2002 |
| WO | WO 02/83656 A2 | 10/2002 |
| WO | WO 02/83656 A3 | 10/2002 |
| WO | WO 02/100846 A1 | 12/2002 |
| WO | WO 2004/089918 A1 | 10/2004 |

* cited by examiner

AZOLE COMPOUND AND MEDICINAL USE THEREOF

TECHNICAL FIELD

The present invention relates to a novel azole compound, more particularly, the present invention relates to an azole compound or a pharmaceutically acceptable salt thereof having a protein tyrosine phosphatase 1B (PTP1B) inhibitory activity, and a pharmaceutical composition containing the same.

BACKGROUND ART

Diabetes causes various metabolic abnormalities including a chronic hyperglycemia state as a main characteristic, which shows various symptoms based on mouth dryness, polydipsia, polyuria, decrease in body weight and the like, based on hyperglycemia. It is known that, when such hyperglycemia state is maintained for a long time, various complications such as retinopathy, nephropathy, neuropathy, cardiac infarction and cerebral infarction based on arteriosclerosis, and the like are developed.

Diabetes is roughly divided into four types of type I diabetes (IDDM; Insulin Dependent Diabetes Mellitus), wherein pancreatic beta cells are damaged or destroyed to cause absolute insulin deficiency, type II diabetes (NIDDM; Non-Insulin Dependent Diabetes Mellitus) wherein relative insulin deficiency is developed due to insulin resistance and lower insulin secretion, specific diabetes which secondarily results from genetic abnormalities, other diseases and the like, and gestational diabetes. Some of those diagnosed with type II diabetes at the time of the onset may gradually lose their ability to secrete insulin with the progression of the disease and result in type I diabetes.

Considering the saccharometabolism of living organisms, energy sources and materials to be the constituent components of living organisms are taken into the body intermittently; for example, the brain keeps on consuming glucose. Under such situation, the blood glucose level is maintained almost constantly, and what enables such control of the blood glucose level includes hormones involved in control of the blood glucose level, metabolism in organs, interaction of exchanging sugar and the like between organs. Of such hormones, particularly the action of insulin involved in the control of the blood glucose level is important, and its disorder, namely, insulin resistance and lower secretion of insulin are considered to be deeply involved in diabetes.

Insulin is secreted from pancreatic beta cells, binds with an insulin receptor present on the membrane surface of the skeletal muscle cell and adipocyte, which are its target cells, after which tyrosine residue in the intracellular domain is self-phosphorylated. Then, tyrosine residues such as insulin receptor substrate (IRS), APS (adapter protein containing PH and SH2 domain) and the like are phosphorylated and $PI_3$ kinase -Akt pathway is activated, which causes translocation of glucose transporter to cell membrane, where glucose uptake occurs to lower the blood glucose level. On the other hand, tyrosine phosphatase that causes tyrosine dephosphorylation to negatively control intracellular signal transduction by insulin is also present, and suppresses activation thereof. In this way, while tyrosine phosphorylation plays a key role in the insulin action, considering that tyrosine phosphorylation depends on the activity balance between tyrosine kinase (phosphorylation enzyme) and tyrosine phosphatase (dephosphorylation enzyme), tyrosine phosphatase is presumed to have function to significantly control insulin signal transduction directly together with tyrosine kinase.

At present, tyrosine phosphatase forms a large gene family and more than 70 some kinds of isozyme have been reported. Of such isozymes, protein tyrosine phosphatase 1B (PTP1B) is considered to be a phosphatase specific to insulin signal transduction. Particularly, given the reports on increased gene expression of PTP1B by high glucose culture, and shift of intracellular localization thereof, which decreases insulin receptor and IRS-1 tyrosine phosphorylation and induces insulin resistance (J. Biol. Chem., 270: 7724–7730, 1995; J. Biochem. (Tokyo), 123: 813–820, 1998); and introduction of wild-type PTP1B prevents translocation of glucose transporter GLUT4, resulting in ineffectiveness in a phosphatase activity deficient mutant, and recently on enhanced insulin sensitivity of PTP1B knockout mouse to be obesity resistant to high-fat diet (Science, 283: 1544–1548, 1999), this enzyme is suggested to be one possible target of insulin resistance improvement. In fact, an insulin resistance improvement effect of vanadic acid long known as a tyrosine phosphatase inhibitor has been acknowledged in animal test and the like.

Accordingly, such tyrosine phosphatase, particularly a drug that suppresses and/or inhibits abnormal activation of PTP1B can be a new type of therapeutic agent for diabetes, which enhances insulin sensitivity, insulin resistance and/or glucose resistance, and restores normal insulin intracellular signal transduction. In addition, application to a therapeutic drug for various diseases such as obesity, neurodegenerative disease and the like is also expected.

Recently, various reports have been documented on compounds aiming at treatment of diseases such as diabetes and the like, by inhibiting protein tyrosine phosphatase.

For example, WO 00/17211 discloses a phosphonic acid derivative having a PTP1B inhibitory action. However, this publication does not disclose a compound having a structure as that of the compound of the present invention, not to mention a description suggestive thereof.

JP-11-508919A (U.S. Pat. No. 5,770,620) discloses an arylacrylic acid derivative useful as a protein tyrosine phosphatase inhibitor. However, this publication does not disclose a compound having a structure as that of the compound of the present invention, not to mention a description suggestive thereof.

WO 98/27092 (U.S. Pat. No. 6,080,772) discloses a thiazole compound having a protein tyrosine phosphatase inhibitory action. However, this publication does not disclose a compound having a structure as that of the compound of the present invention, not to mention a description suggestive thereof.

WO 99/58522 discloses a naphtho[2,3-B]heteroal-4-yl derivative, WO 99/58511 discloses an oxa/thiazole-arylcarboxylic acid derivative, WO 99/58521 and U.S. Pat. No. 6,110,962 disclose 11-aryl-benzo[B]naphtho[2,3-D]furan and 11-aryl-benzo[B]naphtho[2,3-D]thiophene derivatives, WO 99/58518 discloses a biphenyl-oxo-acetic acid derivative, WO 99/61419 discloses a 2,3,5-substituted biphenyl derivative, WO 99/58520 discloses a biphenyl-sulfonyl-aryl-carboxylic acid derivative, WO 99/61435 discloses benzothiophene, benzofuran and indole derivatives, U.S. Pat. No. 6,103,708 discloses furan, benzofuran and thiophene derivatives, U.S. Pat. No. 6,110,963 discloses an aryl-oxo-acetic acid derivative, U.S. Pat. No. 6,001,867 discloses a 1-aryl-dibenzothiophene derivative, U.S. Pat. No. 6,057,316 discloses a 4-aryl-1-oxa-9-thia-cyclopenta[B] fluorene derivative, U.S. Pat. No. 6,063,815 discloses a benzophenone derivative, as each having a protein tyrosine phosphatase inhibitory action. However, these publications do not disclose compounds having a structure as that of the compound of the present invention, not to mention a description suggestive thereof.

As compounds having a thiazole or oxazole structure, the following have been reported.

WO 00/45635 discloses a 2-substituted thiazole derivative. However, the compound of this publication has a carbamoyl group at the terminal of the substituent at the 2-position of the thiazole ring and this publication does not disclose a compound having a structure as that of the compound of the present invention, not to mention a description suggestive thereof. In addition, the compound of this publication is useful as an antimicrobial agent or an analgesic, and the publication does not disclose its usefulness as a PTP1B inhibitor, not to mention a description suggestive thereof.

JP-2000-504039A describes a 2-anilino-4-phenylthiazole derivative. However, the compound of this publication has an anilino group substituted by a hydroxyl group or a carboxyl group at the 2-position of a thiazole ring, a phenyl group at the 4-position, and a substituent at the 2-position of the 4-position phenyl group, and this publication does not disclose a compound having a structure as that of the compound of the present invention, not to mention a description suggestive thereof. In addition, the compound of this publication is useful as a CRF (corticotropin releasing factor) antagonist, and the publication does not disclose its usefulness as a PTP1B inhibitor, not to mention a description suggestive thereof.

JP-A-4-154773 describes a thiazole derivative represented by the formula

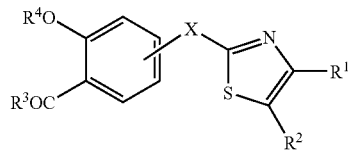

wherein $R^1$ and $R^2$ are the same or different and each is hydrogen atom, halogen atom, lower alkyl group, phenyl group, substituted phenyl group, pyridyl group or substituted pyridyl group, $R^3$ is hydroxyl group, lower alkoxy group or —N($R^5$)($R^6$) wherein $R^5$ and $R^6$ are the same or different and each is hydrogen atom or lower alkyl group, $R^4$ is hydrogen atom or lower alkyl group, and X is amino group, amide group, carbonyl group, alkylene group, oxygen atom or sulfur atom. However, this publication does not disclose a compound having a structure as that of the compound of the present invention, not to mention a description suggestive thereof. In addition, the compound of this publication is useful as an antiinflammatory agent, and the publication does not disclose its usefulness as a PTP1B inhibitor, not to mention a description suggestive thereof.

WO 94/08982 describes a 4-phenylthiazole derivative. However, the compound of this publication has phenyl group at the 4-position of a thiazole ring, and a substituent such as halogen and the like at the 2-position of the 4-position phenyl group. This publication does not disclose a compound having a structure as that of the compound of the present invention, not to mention a description suggestive thereof. In addition, the compound of this publication is useful as a pest control agent, and the publication does not disclose its usefulness as a PTP1B inhibitor, not to mention a description suggestive thereof.

WO 02/39997 describes compounds represented by the formula

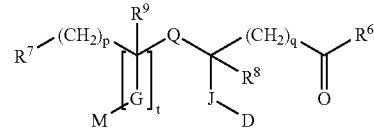

wherein $R^6$ is hydroxyl group or protected prodrug moiety, $R^7$ is hydrogen atom, carboxy group, arylaminocarbonyl group, aroyl group, aryl group, alkylaminocarbonyl group, aminocarbonyl group, alkenylaminocarboxy group, hydroxyl group, alkoxy group, ether, thiol, amino group-containing heterocyclic group or protected prodrug moiety, $R^8$ is hydrogen atom or alkyl group that may be bonded with D to form a ring, $R^9$ is lower alkyl group or hydrogen atom, Q is bond, oxygen atom, sulfur atom, $CR^3OH$, $CR^3SH$, $CR^3NR^{3a}R^{3b}$, $NR^3$, $(CR^3R^{3a})_n$, $O(CR^3R^{3b})_n$ or $(C R_3 R^{3a})_n O (CR^{3b}R^{3c})_n$ wherein n is an integer of 0 or 1 to 3, $R^3$, $R^{3a}$, $R^{3b}$ and $R^{3c}$ are each independently hydrogen atom, optionally substituted straight chain, cyclic or branched chain $C_{1-6}$ alkyl group, $C_{2-6}$ alkenyl group, acyl group, arylalkyl group, aryloxycarbonyl group, arylaminocarbonyl group, arylalkylsulfonyl group or aryl group, G is a linking moiety, M is anchor moiety, J is bond, alkylene group, alkenylene group or alkynylene group, D is hydrogen atom, alkoxy group, amine, alkyl group, alkenyl group, alkynyl group, aryl group or heteroaryl group that may be bonded with G, M or Q to form a ring, t is 0 or 1, p is 0 or an integer of 1 to 5, and q is 0 or an integer of 1 to 3, and the formula

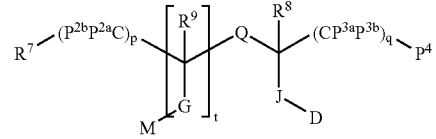

wherein $P^4$ is carboxy group, cleavable prodrug moiety, $COOP^{4'}$, $(CH_2)_{1-4}SP^{4'}$ or $C(O)NP^{4'}P^{4''}$, $R^7$ is hydrogen atom, carboxy group, optionally substituted lower alkyl ester, lower alkenyl ester, ester added with secondary amine substituted by lower alkyl, arylaminocarbonyl group, aroyl group, aryl group, alkylaminocarbonyl group, aminocarbonyl group, $COOR^{7'}$, $CONR^{7'}R^{7''}$, hydroxyl group, ether, thiol, amino group, $(CH_2)_{1-4}SR^{7'}$, heterocyclic group or cleavable prodrug moiety, $P^{4'}$, $P^{4''}$, $R^{7'}$ and $R^{7''}$ are each independently hydrogen atom, $C_{1-6}$ alkyl group, $C_{2-6}$ alkenyl group, $C_{2-6}$ alkynyl group or optionally substituted aryl group, $R^8$ is hydrogen atom, alkyl group or covalent bond with D, $R^9$ is lower alkyl group or hydrogen atom, Q is bond, oxygen atom, sulfur atom, $CR^3OH$, $CR^3SH$, $CR^3NR^{3a}R^{3b}$, $NR^3$, $(CR^3R^{3a})_n$, $O(CR^3R^{3b})_n$ or $(CR^3R^{3a})_nO(CR^{3b}R^{3c})_n$ wherein n is 0 or an integer of 1 to 3, $R^3$, $R^{3a}$, $R^{3b}$ and $R^{3c}$ are each independently hydrogen atom, optionally substituted $C_{1-6}$ straight chain or branched chain alkyl group, $C_{2-6}$ straight chain or branched chain alkenyl group, aryloxycarbonyl group, arylaminocarbonyl group, arylalkylsulfonyl group, arylalkyl group, optionally substituted acyl group, aryl group or C$_{3-8}$ ring optionally substituted by up to 4 hetero atoms, P$^{2a}$, P$^{2b}$, P$^{3a}$ and P$^{3b}$ are each independently hydrogen atom or optionally substituted straight chain, branched chain or cyclic C$_{1-5}$ alkyl group, G is linking moiety, M is anchor moiety, J is bond, alkylene group, alkenylene group or alkynylene group, D is hydrogen atom, alkyl group, alkenyl group, alkynyl group or aryl group or may be bonded with G, M or Q to form a ring, t is 0 or 1, p is 0 or an integer of 1 to 5, and q is 0 or an integer of 1 to 3, wherein the anchor moiety in each formula is exemplified by thiazole group and oxazole group having, as a substituent, aryl group or heteroaryl group substituted by —NR'R", —CONR'R", —S(O)$_2$NR'R", —S(O)$_{0-2}$R', —NR'R", —O(CR'R")$_{0-2}$CF$_3$, —COR', —CO$_2$R' and —OR' wherein R' and R" are each independently hydrogen atom, C$_{1-6}$ alkyl group, C$_{2-6}$ alkenyl group, C$_{2-6}$ alkynyl group or optionally substituted aryl group, and the linking moiety is exemplified by covalent bond and C$_{1-6}$ alkyl group.

Moreover, a compound represented by the formula

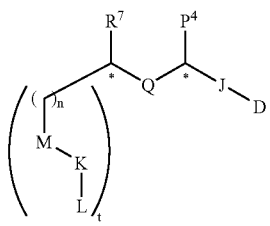

wherein M is carbocyclic group, heterocyclic group or CONR'R" wherein R' and R" are each independently hydrogen atom, C$_{1-6}$ alkyl group, C$_{2-6}$ alkenyl group, C$_{2-6}$ alkynyl group or optionally substituted aryl group, Q is bond, oxygen atom, sulfur atom, CR$^3$OH, CR$^3$SH, CR$^3$NR$^{3a}$R$^{3b}$, NR$^3$, (CR$^3$R$^{3a}$)$_n$, O(CR$^3$R$^{3b}$)$_n$ or (CR$^3$R$^{3a}$)$_n$O(CR$^{3b}$R$^{3c}$)$_n$ wherein n is 0 or an integer of 1 to 3, R$^3$, R$^{3a}$R$^{3b}$ and R$^{3c}$ are each independently hydrogen atom, optionally substituted branched chain, cyclic or straight chain C$_{1-6}$ alkyl group, C$_{2-6}$ alkenyl group, acyl group, arylalkyl group, aryloxycarbonyl group, arylaminocarbonyl group, arylalkylsulfonyl group or aryl group, K is independently selected sublinking moiety, L is independently selected subanchor moiety, P$^4$ is hydrogen atom, carboxy group, (CH$_2$)$_{1-4}$SP$^{4'}$, cleavable prodrug moiety, COOP$^{4'}$ or CONP$^{4'}$P$^{4''}$, R$^7$ is hydrogen atom, carboxy group, aroyl group, aryl group, COOR$^{7'}$, C(O) NR$^{7'}$R$^{7''}$, hydroxyl group, ether, thiol, (CH$_2$)$_{1-4}$SR$^{7'}$, heterocyclic group or cleavable prodrug moiety, P$^{4'}$, P$^{4''}$, R$^{7'}$ and R$^{7''}$ are each independently hydrogen atom, C$_{1-6}$ alkyl group, C$_{2-6}$ alkenyl group, C$_{2-6}$ alkynyl group or optionally substituted aryl group, n is 0 or an integer of 1 to 4, D is hydrogen atom, alkyl group, alkoxy group, alkenyl group, amine, hydroxyl group, alkynyl group, aryl group or heteroaryl group, and t is 0 or 1, is described, wherein the sublinking moiety has a covalent bond and the subanchor moiety has an optionally substituted aryl group.

However, this publication does not disclose a compound having a structure as that of the compound of the present invention, not to mention a description suggestive thereof. In addition, the compound of this publication is useful as an angiotensin converting enzyme (ACE)-2 regulator, and the publication does not disclose its usefulness as a PTP1B inhibitor, not to mention a description suggestive thereof.

DISCLOSURE OF THE INVENTION

An object of the present invention is to provide a compound having a superior PTP1B inhibitory action and useful as a therapeutic agent for diabetes, a therapeutic agent for hyperlipidemia or a therapeutic drug of diseases such as obesity, neurodegenerative disease and the like.

Another object of the present invention is to provide a PTP1B inhibitor, a therapeutic agent for diabetes and a therapeutic agent for hyperlipidemia.

The present inventors have conducted intensive studies in an attempt to achieve the above-mentioned objects and found that an azole compound represented by the following formula [I] has a superior PTP1B inhibitory action and is useful as a PTP1B inhibitor, a therapeutic agent for diabetes and a therapeutic agent for hyperlipidemia, which resulted in the completion of the present invention.

The present invention relates to the compounds shown in the following [1] to [54] and use thereof as a pharmaceutical agent.

[1] An azole compound represented by the formula [I]

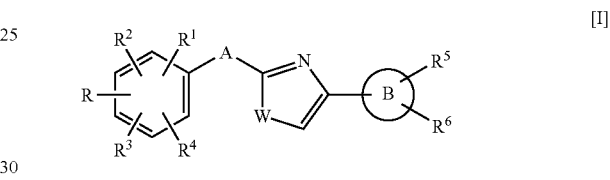

wherein
W is a sulfur atom or an oxygen atom;
R is
(1) —COOR$^7$ wherein R$^7$ is a hydrogen atom or a lower alkyl group),
(2) —X$^1$-A$^1$-COOR$^7$
wherein
X$^1$ is —O—, —N(R$^{15}$)— or —S(O)$_p$— wherein R$^{15}$ is a hydrogen atom or a lower alkyl group, p is 0, 1 or 2,
A$^1$ is a lower alkylene group, and
R$^7$ is a hydrogen atom or a lower alkyl group, or
(3) a tetrazolyl group;
R$^1$, R$^2$, R$^3$ and R$^4$ are each independently
(1) a hydrogen atom,
(2) a halogen atom,
(3) a hydroxyl group,
(4) an optionally substituted lower cycloalkylalkyloxy group,
(5) an optionally substituted aralkyloxy group,
(6) a cyano group,
(7) a nitro group,
(8) a lower alkyl group,
(9) a lower haloalkyl group,
(10) a lower alkoxy group or
(11) a lower haloalkoxy group;
A is a group represented by —(CH$_2$)$_m$—X—
wherein
X is —N(R$^8$)—, —C(R$^9$)(R$^{10}$)—, —CO— or —CO—N (R$^8$)—
wherein
R$^8$ is a hydrogen atom, —SO$_2$R$^{16}$ (R$^{16}$ is a lower alkyl group or an aryl group) or a lower alkyl group, wherein said lower alkyl group is optionally substituted by a substituent selected from the group consisting of a lower alkoxy group, an aryloxy group, —N(R$^{11}$)(R$^{12}$) (R$^{11}$ and R$^{12}$ are each independently a hydrogen atom or a lower alkyl group or may form, together with a nitrogen atom bonded thereto, a 5- to 7-membered hetero ring optionally further having at least one hetero atom selected from the group consisting of nitrogen atom, oxygen atom and sulfur atom), a carboxy group, a lower cycloalkyl group and an optionally substituted aryl group, and R$^9$ and R$^{10}$ are each independently a hydrogen atom or a lower alkyl group or may form lower cycloalkane together with a carbon atom bonded thereto, or may form, together with a carbon atom bonded thereto, a 5- to 7-membered hetero ring optionally further having at least one hetero atom selected from the group consisting of nitrogen atom, oxygen atom and sulfur atom, and m is 0 or an integer of 1 to 3;

B is an aryl group or an aromatic heterocyclic group;

R$^5$ is
(1) a hydrogen atom,
(2) a halogen atom,
(3) a lower alkyl group,
(4) a lower alkoxy group,
(5) a cyano group,
(6) a nitro group,
(7) a lower haloalkyl group or
(8) —S(O)$_r$—R$^{17}$ (R$^{17}$ is a lower alkyl group or an aryl group and r is 0, 1 or 2); and R$^6$ is —(Y)$_{s1}$-(A$^2$)$_s$-Z wherein
s1 and s are each independently 0 or 1,
Y is —O—, —S(O)$_t$—, —N(R$^{13}$)—, —N(R$^{14}$)—CO—, —N(R$^{14}$)—SO$_2$—, —SO$_2$—N(R$^{14}$)—, —C(R$^{18}$)(R$^{19}$)— or —CO—

(wherein
t is 0, 1 or 2,
R$^{13}$ is
(1) a hydrogen atom,
(2) a lower alkyl group (wherein said lower alkyl group optionally substituted by a substituent selected from the group consisting of
    (a) a lower cycloalkyl group,
    (b) an optionally substituted aryl group,
    (c) an optionally substituted heterocyclic group and
    (d) a hydroxyl group),
(3) a lower alkenyl group,
(4) a lower alkylsulfonyl group or
(5) a lower alkylcarbonyl group (wherein said lower alkylcarbonyl group is optionally substituted by a hydroxyl group or a lower alkoxy group), R$^{14}$ is a hydrogen atom or a lower alkyl group, and R$^{18}$ and R$^{19}$ are each independently a hydrogen atom or a lower alkyl group or may form lower cycloalkane together with a carbon atom bonded thereto, or may form, together with a carbon atom bonded thereto, a 5- to 7-membered hetero ring optionally further having at least one hetero atom selected from the group consisting of nitrogen atom, oxygen atom and sulfur atom), A$^2$ is a lower alkylene group optionally substituted by a lower cycloalkyl group, and Z is
(1) a lower cycloalkyl group (wherein said a lower cycloalkyl group is optionally substituted by an optionally substituted phenyl group), (2) an aryl group (wherein said aryl group is optionally substituted by a substituent selected from the group consisting of
    (a) a heterocyclic group optionally substituted by a substituent selected from the group consisting of a lower alkyl group and a lower alkylcarbonyl group,
    (b) a lower cycloalkyl group optionally substituted by a substituent selected from the group consisting of a hydroxyl group, an oxo group, a halogen atom and a lower alkyl group,
    (c) a carboxy group,
    (d) a halogen atom,
    (e) an alkyl group,
    (f) a lower haloalkyl group,
    (g) a lower alkylamino group,
    (h) a di(lower alkyl)amino group,
    (i) a lower alkylthio group and
    (j) a lower alkoxy group),
(3) an optionally substituted aromatic heterocyclic group,
(4) an indanyl group or
(5) a piperazinyl group (wherein said piperazinyl group is optionally substituted by a substituent selected from the group consisting of
    (a) a phenyl group,
    (b) a phenyl lower alkyl group,
    (c) a benzoyl group optionally substituted by a halogen atom and
    (d) a phenyl lower alkoxycarbonyl group), a prodrug thereof or a pharmaceutically acceptable salt thereof.

[2] The azole compound of [1], wherein, in the formula [I], W is a sulfur atom or an oxygen atom;

R is
(1) —COOR$^7$ wherein R$^7$ is a hydrogen atom or a C$_{1-4}$ alkyl group,
(2) —X$^1$-A$^1$-COOR$^7$ wherein
X$^1$ is —O—, —N(R$^{15}$)— or —S(O)$_p$— wherein R$^{15}$ is a hydrogen atom or a C$_{1-4}$ alkyl group and p is 0, 1 or 2,
A$^1$ is a C$_{1-4}$ alkylene group,
R$^7$ is a hydrogen atom or a C$_{1-4}$ alkyl group or
(3) a tetrazolyl group, R$^1$, R$^2$, R$^3$ and R$^4$ are each independently,
(1) a hydrogen atom,
(2) a halogen atom,
(3) a hydroxyl group,
(4) an optionally substituted C$_{3-7}$ cycloalkyl C$_{1-4}$ alkyloxy group,
(5) an optionally substituted aralkyloxy group,
(6) a cyano group,
(7) a nitro group,
(8) a C$_{1-4}$ alkyl group,
(9) a C$_{1-4}$ haloalkyl group,
(10) a C$_{1-4}$ alkoxy group or
(11) a C$_{1-4}$ haloalkoxy group;

A is a group represented by —(CH$_2$)$_m$—X— wherein
X is —N(R$^8$)—, —C(R$^9$)(R$^{10}$)—, —CO— or —CO—N(R$^8$)— wherein
R$^8$ is a hydrogen atom, —SO$_2$R$^{16}$ (R$^{16}$ is a C$_{1-6}$ alkyl group or an aryl group) or a C$_{1-6}$ alkyl group, wherein said C$_{1-6}$ alkyl group is optionally substituted by a substituent selected from the group consisting of a $C_{1-4}$ alkoxy group, an aryloxy group, —N(R$^{11}$)(R$^{12}$) (R$^{11}$ and R$^{12}$ are each independently a hydrogen atom or a $C_{1-4}$ alkyl group or may form, together with a nitrogen atom bonded thereto, a 5- to 7-membered hetero ring optionally further having at least one hetero atom selected from the group consisting of nitrogen atom, oxygen atom and sulfur atom), a carboxy group, a $C_{3-7}$ cycloalkyl group and an optionally substituted aryl group, R$^9$ and R$^{10}$ are each independently a hydrogen atom or a $C_{1-4}$ alkyl group, or may form a $C_{3-7}$ cycloalkane together with a carbon atom bonded thereto, or may form, together with a carbon atom bonded thereto, a 5- to 7-membered hetero ring optionally further having at least one hetero atom selected from the group consisting of nitrogen atom, oxygen atom and sulfur atom, m is 0 or an integer of 1 to 3;

B is an aryl group or an aromatic heterocyclic group;

R$^5$ is (1) a hydrogen atom, (2) a halogen atom, (3) a $C_{1-4}$ alkyl group, (4) a $C_{1-4}$ alkoxy group, (5) a cyano group, (6) a nitro group, (7) a $C_{1-4}$ haloalkyl group or (8) —S(O)$_r$—R$^{17}$ (R$^{17}$ is a $C_{1-6}$ alkyl group or an aryl group and r is 0, 1 or 2);

R$^6$ is —(Y)$_{s1}$-(A$^2$)$_s$-Z wherein s1 and s are each independently 0 or 1, Y is —O—, —S(O)$_t$—, —N(R$^{13}$)—, —N(R$^{14}$)—CO—, —N(R$^{14}$)—SO$_2$—, —SO$_2$—N(R$^{14}$)—, —C(R$^{18}$)(R$^{19}$)— or —CO—

(wherein t is 0, 1 or 2,

R$^{13}$ is (1) a hydrogen atom, (2) a $C_{1-4}$ alkyl group (wherein said $C_{1-4}$ alkyl group is optionally substituted by a substituent selected from the group consisting of (a) a $C_{3-7}$ cycloalkyl group, (b) an optionally substituted aryl group, (c) an optionally substituted heterocyclic group and (d) a hydroxyl group), (3) a $C_{2-4}$ alkenyl group, (4) a $C_{1-4}$ alkylsulfonyl group or (5) a $C_{1-4}$ alkylcarbonyl group (wherein said $C_{1-4}$ alkylcarbonyl group is optionally substituted by a hydroxyl group or a $C_{1-4}$ alkoxy group), R$^{14}$ is a hydrogen atom or a $C_{1-4}$ alkyl group, R$^{18}$ and R$^{19}$ are each independently a hydrogen atom or a $C_{1-4}$ alkyl group, or may form $C_{3-7}$ cycloalkane together with a carbon atom bonded thereto, or may form, together with a carbon atom bonded thereto, a 5- to 7-membered hetero ring optionally further having at least one hetero atom selected from the group consisting of nitrogen atom, oxygen atom and sulfur atom), A$^2$ is a $C_{1-4}$ alkylene group optionally substituted by a $C_{3-7}$ cycloalkyl group, Z is (1) a $C_{3-7}$ cycloalkyl group (wherein said $C_{3-7}$ cycloalkyl group is optionally substituted by a phenyl group optionally substituted by a halogen atom), (2) an aryl group (wherein said aryl group is optionally substituted by a substituent selected from the group consisting of (a) a heterocyclic group optionally substituted by a substituent selected from the group consisting of a $C_{1-4}$ alkyl group and a $C_{1-4}$ alkylcarbonyl group, (b) a $C_{3-7}$ cycloalkyl group optionally substituted by a substituent selected from the group consisting of a hydroxyl group, an oxo group, a halogen atom and a $C_{1-4}$ alkyl group, (c) a carboxy group, (d) a halogen atom, (e) a $C_{1-8}$ alkyl group, (f) a $C_{1-4}$ haloalkyl group, (g) a $C_{1-4}$ alkylamino group, (h) a di($C_{1-4}$ alkyl)amino group, (i) a $C_{1-4}$ alkylthio group and (j) a $C_{1-4}$ alkoxy group), (3) an aromatic heterocyclic group (wherein said aromatic heterocyclic group is optionally substituted by a substituent selected from the group consisting of (a) a heterocyclic group optionally substituted by a $C_{1-4}$ alkyl group, (b) a $C_{1-6}$ alkyl group, (c) an aryl group optionally substituted by a halogen atom or a $C_{1-4}$ haloalkyl group, (d) a halogen atom, (e) a $C_{1-4}$ haloalkyl group, (f) a carboxy group, (g) a $C_{3-7}$ cycloalkyl group and (h) a $C_{1-4}$ alkoxy group), (4) an indanyl group or (5) a piperazinyl group (wherein said piperazinyl group is optionally substituted by a substituent selected from the group consisting of (a) a phenyl group, (b) a phenyl $C_{1-4}$ alkyl group, (c) a benzoyl group optionally substituted by a halogen atom and (d) a phenyl $C_{1-4}$ alkoxycarbonyl group), a prodrug thereof or a pharmaceutically acceptable salt thereof.

[3] The azole compound of [2], wherein W is a sulfur atom or an oxygen atom,

R is (1) —COOR$^7$ wherein R$^7$ is a hydrogen atom, (2) —X$^1$-A$^1$-COOR$^7$ wherein X$^1$ is —O—, A$^1$ is a $C_{1-4}$ alkylene group, R$^7$ is a hydrogen atom or (3) a tetrazolyl group;

R$^1$, R$^2$, R$^3$ and R$^4$ are each independently (1) a hydrogen atom, (2) a halogen atom, (3) a hydroxyl group, (4) an optionally substituted $C_{3-7}$ cycloalkyl $C_{1-4}$ alkyloxy group or (5) an optionally substituted aralkyloxy group;

A is a group represented by —(CH$_2$)$_m$—X— wherein

X is —N(R$^8$)—, —C(R$^9$)(R$^{10}$)— or —CO— wherein

R$^8$ is a hydrogen atom or a C$_{1-6}$ alkyl group, wherein said C$_{1-6}$ alkyl group is optionally substituted by a substituent selected from the group consisting of a C$_{1-4}$ alkoxy group, an aryloxy group, —N(R$^{11}$)(R$^{12}$) (R$^{11}$ and R$^{12}$ are each independently a hydrogen atom or a C$_{1-4}$ alkyl group or may form, together with a nitrogen atom bonded thereto, a 5- to 7-membered hetero ring optionally further having at least one hetero atom selected from the group consisting of nitrogen atom, oxygen atom and sulfur atom), a carboxy group, a C$_{3-7}$ cycloalkyl group and an optionally substituted aryl group, R$^9$ and R$^{10}$ are each independently a hydrogen atom or a C$_{1-4}$ alkyl group, or may form C$_{3-7}$ cycloalkane together with a carbon atom bonded thereto, or may form, together with a carbon atom bonded thereto, a 5- to 7-membered hetero ring optionally further having at least one hetero atom selected from the group consisting of nitrogen atom, oxygen atom and sulfur atom, m is 0 or an integer of 1 to 3;

B is an aryl group or an aromatic heterocyclic group;

R$^5$ is (1) a hydrogen atom,
(2) a halogen atom,
(3) a C$_{1-4}$ alkyl group or
(4) a C$_{1-4}$ alkoxy group;

R$^6$ is —(Y)$_{s1}$-(A$^2$)$_s$-Z wherein s1 and s are each independently 0 or 1, Y is —O—, —S(O)$_t$—, —N(R$^{13}$)—, —N(R$^{14}$)—CO— or —N(R$^{14}$)—SO$_2$— wherein t is 0, 1 or 2,

R$^{13}$ is (1) a hydrogen atom,
(2) a C$_{1-4}$ alkyl group (wherein said C$_{1-4}$ alkyl group is optionally substituted by a substituent selected from the group consisting of
  (a) a C$_{3-7}$ cycloalkyl group,
  (b) an optionally substituted aryl group,
  (c) an optionally substituted heterocyclic group and
  (d) a hydroxyl group),
(3) a C$_{2-4}$ alkenyl group,
(4) a C$_{1-4}$ alkylsulfonyl group or
(5) a C$_{1-4}$ alkylcarbonyl group (wherein said C$_{1-4}$ alkylcarbonyl group is optionally substituted by a hydroxyl group or a C$_{1-4}$ alkoxy group), R$^{14}$ is a hydrogen atom or a C$_{1-4}$ alkyl group, A$^2$ is a C$_{1-4}$ alkylene group optionally substituted by a C$_{3-7}$ cycloalkyl group, Z is (1) a C$_{3-7}$ cycloalkyl group (wherein said C$_{3-7}$ cycloalkyl group is optionally substituted by a phenyl group), (2) an aryl group (wherein said aryl group is optionally substituted by a substituent selected from the group consisting of
  (a) a heterocyclic group optionally substituted by a C$_{1-4}$ alkyl group or a C$_{1-4}$ alkylcarbonyl group,
  (b) a C$_{3-7}$ cycloalkyl group optionally substituted by a substituent selected from the group consisting of a hydroxyl group, an oxo group, a halogen atom and a C$_{1-4}$ alkyl group,
  (c) a carboxy group,
  (d) a halogen atom,
  (e) a C$_{1-8}$ alkyl group,
  (f) a C$_{1-4}$ haloalkyl group,
  (g) a C$_{1-4}$ alkylamino group and
  (h) a di(C$_{1-4}$ alkyl)amino group,
  (i) a C$_{1-4}$ alkylthio group and
  (j) a C$_{1-4}$ alkoxy group),
(3) an aromatic heterocyclic group (wherein said aromatic heterocyclic group is optionally substituted by a substituent selected from the group consisting of
  (a) a heterocyclic group,
  (b) a C$_{1-4}$ alkyl group and
  (c) a phenyl group optionally substituted by a halogen atom or a C$_{1-4}$ haloalkyl group),
(4) an indanyl group or
(5) a piperazinyl group (wherein said piperazinyl group is optionally substituted by a substituent selected from the group consisting of
  (a) a phenyl group,
  (b) a phenyl C$_{1-4}$ alkyl group and
  (c) a phenyl C$_{1-4}$ alkoxycarbonyl group), a prodrug thereof or a pharmaceutically acceptable salt thereof.

[4] The azole compound of [3], wherein W is a sulfur atom and m is 0 or 1, a prodrug thereof or a pharmaceutically acceptable salt thereof.

[5] The azole compound of [4], wherein A is —(CH$_2$)$_m$—X— wherein

X is —N(R$^8$)— wherein R$^8$ is a hydrogen atom or a C$_{1-6}$ alkyl group, wherein said C$_{1-6}$ alkyl group is optionally substituted by a substituent selected from the group consisting of a C$_{1-4}$ alkoxy group, an aryloxy group, —N(R$^{11}$)(R$^{12}$) (R$^{11}$ and R$^{12}$ are each independently a hydrogen atom or a C$_{1-4}$ alkyl group or may form, together with a nitrogen atom bonded thereto, a 5- to 7-membered hetero ring optionally further having at least one hetero atom selected from the group consisting of nitrogen atom, oxygen atom and sulfur atom), a carboxy group, a C$_{3-7}$ cycloalkyl group and an optionally substituted aryl group, and m is 0 or 1, a prodrug thereof or a pharmaceutically acceptable salt thereof.

[6] The azole compound of [5], wherein R is —X$^1$-A$^1$-COOR$^7$ wherein each symbol is as defined in [3], a prodrug thereof or a pharmaceutically acceptable salt thereof.

[7] The azole compound of [5], wherein R is —COOR$^7$ wherein

R$^7$ is a hydrogen atom, a prodrug thereof or a pharmaceutically acceptable salt thereof.

[8] The azole compound of [7], wherein R$^1$, R$^2$, R$^3$ and R$^4$ are hydrogen atoms, a prodrug thereof or a pharmaceutically acceptable salt thereof.

[9] The azole compound of [8], wherein B is a phenyl group, a thiazolyl group, a pyridyl group, a benzothiazolyl group, a benzoimidazolyl group or a benzoxazolyl group, a prodrug thereof or a pharmaceutically acceptable salt thereof.

[10] The azole compound of [9], wherein B is a phenyl group, a prodrug thereof or a pharmaceutically acceptable salt thereof.

[11] The azole compound of [10], wherein $R^5$ is a hydrogen atom, a prodrug thereof or a pharmaceutically acceptable salt thereof.

[12] The azole compound of [11], wherein, for $R^6$, Z is
(1) a $C_{3-7}$ cycloalkyl group
(wherein said $C_{3-7}$ cycloalkyl group is optionally substituted by a phenyl group),
(2) an aryl group
(wherein said aryl group is optionally substituted by a substituent selected from the group consisting of
  (a) a heterocyclic group optionally substituted by a $C_{1-4}$ alkyl group or a $C_{1-4}$ alkylcarbonyl group,
  (b) a $C_{3-7}$ cycloalkyl group optionally substituted by a substituent selected from the group consisting of a hydroxyl group, an oxo group, a halogen atom and a $C_{1-4}$ alkyl group,
  (c) a carboxy group,
  (d) a halogen atom,
  (e) a $C_{1-8}$ alkyl group,
  (f) a $C_{1-4}$ haloalkyl group,
  (g) a $C_{1-4}$ alkylamino group,
  (h) a di($C_{1-4}$ alkyl)amino group,
  (i) a $C_{1-4}$ alkylthio group and
  (j) a $C_{1-4}$ alkoxy group) or
(3) an aromatic heterocyclic group
(wherein said aromatic heterocyclic group is optionally substituted by a substituent selected from the group consisting of
  (a) a heterocyclic group,
  (b) a $C_{1-4}$ alkyl group and
  (c) a phenyl group optionally substituted by a halogen atom or a $C_{1-4}$ haloalkyl group), a prodrug thereof or a pharmaceutically acceptable salt thereof.

[13] The azole compound of [12], wherein Z is an aryl group optionally substituted by a substituent selected from the group consisting of
(a) a heterocyclic group optionally substituted by a $C_{1-4}$ alkyl group or a $C_{1-4}$ alkylcarbonyl group,
(b) a $C_{3-7}$ cycloalkyl group optionally substituted by a substituent selected from the group consisting of a hydroxyl group, an oxo group, a halogen atom and a $C_{1-4}$ alkyl group,
(c) a carboxy group,
(d) a halogen atom,
(e) a $C_{1-8}$ alkyl group,
(f) a $C_{1-4}$ haloalkyl group,
(g) a $C_{1-4}$ alkylamino group,
(h) a di($C_{1-4}$ alkyl)amino group,
(i) a $C_{1-4}$ alkylthio group and
(j) a $C_{1-4}$ alkoxy group, a prodrug thereof or a pharmaceutically acceptable salt thereof.

[14] The azole compound of [13], wherein Z is a phenyl group substituted by a substituent selected from the group consisting of
(a) a cyclohexyl group or a cyclopentyl group optionally substituted by a substituent selected from the group consisting of a hydroxyl group, an oxo group, a halogen atom and a $C_{1-4}$ alkyl group,
(b) a heterocyclic group optionally substituted by a $C_{1-4}$ alkyl group or a $C_{1-4}$ alkylcarbonyl group (wherein said heterocyclic group is selected from the group consisting of a piperidinyl group, a morpholinyl group, a piperazinyl group, a tetrahydropyranyl group, a pyrrolidinyl group and a pyrrolyl group) and
(c) a $C_{1-8}$ alkyl group, a prodrug thereof or a pharmaceutically acceptable salt thereof.

[15] The azole compound of [14], wherein Z is a phenyl group substituted by a cyclohexyl group optionally substituted by a substituent selected from the group consisting of a hydroxyl group, an oxo group, a halogen atom and a $C_{1-4}$ alkyl group, a prodrug thereof or a pharmaceutically acceptable salt thereof.

[16] The azole compound of [13] or [14] wherein, for $R^6$, Y is —O—, —N($R^{13}$)— or —N($R^{14}$)—CO—
wherein
$R^{13}$ is a hydrogen atom, a $C_{1-4}$ alkyl group or a $C_{2-4}$ alkenyl group, wherein said $C_{1-4}$ alkyl group is optionally substituted by a substituent selected from the group consisting of a $C_{3-7}$ cycloalkyl group, an optionally substituted aryl group, an optionally substituted heterocyclic group and a hydroxyl group, $R^{14}$ is a hydrogen atom or a $C_{1-4}$ alkyl group, and s1 is 1, a prodrug thereof or a pharmaceutically acceptable salt thereof.

[17] The azole compound of [16], wherein, for $R^6$, $A^2$ is a methylene group, a prodrug thereof or a pharmaceutically acceptable salt thereof.

[18] A pharmaceutical composition comprising an azole compound of any of [1] to [17], a prodrug thereof or a pharmaceutically acceptable salt thereof, and a pharmaceutically acceptable carrier.

[19] A pharmaceutical composition for inhibiting protein Tyrosine Phosphatase 1B, which comprises an azole compound of any of [1] to [17], a prodrug thereof or a pharmaceutically acceptable salt thereof, and a pharmaceutically acceptable carrier.

[20] A pharmaceutical composition for treating diabetes, which comprises an azole compound of any of [1] to [17], a prodrug thereof or a pharmaceutically acceptable salt thereof, and a pharmaceutically acceptable carrier.

[21] A pharmaceutical composition for treating hyperlipidemia, which comprises an azole compound of any of [1] to [17], a prodrug thereof or a pharmaceutically acceptable salt thereof, and a pharmaceutically acceptable carrier.

[22] The pharmaceutical composition of [18], which is used in combination with a different therapeutic drug for hyperlipidemia.

[23] The pharmaceutical composition of [22], wherein the therapeutic drug for hyperlipidemia is a statin pharmaceutical agent.

[24] The pharmaceutical composition of [23], wherein the statin pharmaceutical agent is selected from the group consisting of lovastatin, simvastatin, pravastatin, fluvastatin, atorvastatin and cerivastatin.

[25] The pharmaceutical composition of [18], which is used in combination with a different therapeutic drug for diabetes.

[26] The pharmaceutical composition of [25], which is used in combination with a therapeutic agent for diabetes selected from the group consisting of an insulin secretagogue, a sulfonylurea, a sulfonamide, a biguanide, an α glucosidase inhibitor, an insulin preparation and an insulin sensitizer.

[27] The pharmaceutical composition of [26], wherein the therapeutic agent for diabetes is selected from the group consisting of nateglide, glimepiride, glibenclamide, gliclazide, acetohexamide, tolbutamide, glyclopyramide, tolazamide, glybuzole, metformin hydrochloride, buformin hydrochloride, voglibose, acarbose, insulin and pioglitazone hydrochloride.

[28] The pharmaceutical composition of [20], which is used in combination with a different therapeutic drug for hyperlipidemia.

[29] The pharmaceutical composition of [28], wherein the therapeutic drug for hyperlipidemia is a statin pharmaceutical agent.

[30] The pharmaceutical composition of [29], wherein the statin pharmaceutical agent is selected from the group consisting of lovastatin, simvastatin, pravastatin, fluvastatin, atorvastatin and cerivastatin.

[31] The pharmaceutical composition of [20], which is used in combination with a different therapeutic drug for diabetes.

[32] The pharmaceutical composition of [31], which is used in combination with a therapeutic drug for diabetes selected from the group consisting of an insulin secretagogue, a sulfonylurea, a sulfonamide, a biguanide, an α glucosidase inhibitor, an insulin preparation and an insulin sensitizer.

[33] The pharmaceutical composition of [32], wherein the therapeutic agent for diabetes is selected from the group consisting of nateglide, glimepiride, glibenclamide, gliclazide, acetohexamide, tolbutamide, glyclopyramide, tolazamide, glybuzole, metformin hydrochloride, buformin hydrochloride, voglibose, acarbose, insulin and pioglitazone hydrochloride.

[34] The pharmaceutical composition of [21], which is used in combination with a different therapeutic drug for hyperlipidemia.

[35] The pharmaceutical composition of [34], wherein the therapeutic drug for hyperlipidemia is a statin pharmaceutical agent.

[36] The pharmaceutical composition of [35], wherein the statin pharmaceutical agent is selected from the group consisting of lovastatin, simvastatin, pravastatin, fluvastatin, atorvastatin and cerivastatin.

[37] The pharmaceutical composition of [21], which is used in combination with a different therapeutic drug for diabetes.

[38] The pharmaceutical composition of [37], which is used in combination with a therapeutic drug for diabetes selected from the group consisting of an insulin secretagogue, a sulfonylurea, a sulfonamide, a biguanide, an α glucosidase inhibitor, an insulin preparation and an insulin sensitizer.

[39] The pharmaceutical composition of [38], wherein the therapeutic agent for diabetes is selected from the group consisting of nateglide, glimepiride, glibenclamide, gliclazide, acetohexamide, tolbutamide, glyclopyramide, tolazamide, glybuzole, metformin hydrochloride, buformin hydrochloride, voglibose, acarbose, insulin and pioglitazone hydrochloride.

[40] A method of inhibiting protein Tyrosine Phosphatase 1B, which comprises administering an effective amount of an azole compound of any of [1] to [17], a prodrug thereof or a pharmaceutically acceptable salt thereof to a mammal.

[41] A method of treating diabetes, which comprises administering an effective amount of an azole compound of any of [1] to [17], a prodrug thereof or a pharmaceutically acceptable salt thereof to a mammal.

[42] A method of treating hyperlipidemia, which comprises administering an effective amount of an azole compound of any of [1] to [17], a prodrug thereof or a pharmaceutically acceptable salt thereof to a mammal.

[43] Use of an azole compound of any of [1] to [17], a prodrug thereof or a pharmaceutically acceptable salt thereof for the production of a protein tyrosine phosphatase 1B inhibitor.

[44] Use of an azole compound of any of [1] to [17], a prodrug thereof or a pharmaceutically acceptable salt thereof for the production of a therapeutic agent for diabetes.

[45] Use of an azole compound of any of [1] to [17], a prodrug thereof or a pharmaceutically acceptable salt thereof for the production of a therapeutic agent for hyperlipidemia.

[46] A commercial package comprising the pharmaceutical composition of [18] and a written matter associated therewith, the written matter stating that said pharmaceutical composition can or should be used for inhibiting protein Tyrosine Phosphatase 1B.

[47] A commercial package comprising the pharmaceutical composition of [18] and a written matter associated therewith, the written matter stating that said pharmaceutical composition can or should be used for treating diabetes.

[48] A commercial package comprising the pharmaceutical composition of [18] and a written matter associated therewith, the written matter stating that said pharmaceutical composition can or should be used for treating hyperlipidemia.

[49] A method of treating hyperlipidemia, which comprises administering an effective amount of an azole compound of any of [1] to [17], a prodrug thereof or a pharmaceutically acceptable salt thereof to a mammal, and administering an effective amount of a different therapeutic drug for hyperlipidemia to said mammal.

[50] The method of treating of [49], wherein the therapeutic drug for hyperlipidemia is a statin pharmaceutical agent.

[51] The method of treating of [50], wherein the statin pharmaceutical agent is selected from the group consisting of lovastatin, simvastatin, pravastatin, fluvastatin, atorvastatin and cerivastatin.

[52] A method of treating diabetes, which comprises administering an effective amount of an azole compound of any of [1] to [17], a prodrug thereof or a pharmaceutically acceptable salt thereof to a mammal, and administering an effective amount of a different therapeutic agent for diabetes to said mammal.

[53] The method of treating of [52], wherein the therapeutic agent for diabetes is selected from the group consisting of an insulin secretagogue, a sulfonylurea, a sulfonamide, a biguanide, an α glucosidase inhibitor, an insulin preparation and an insulin sensitizer.

[54] The method of treating of [53], wherein the therapeutic agent for diabetes is selected from the group consisting of nateglide, glimepiride, glibenclamide, gliclazide, acetohexamide, tolbutamide, glyclopyramide, tolazamide, glybuzole, metformin hydrochloride, buformin hydrochloride, voglibose, acarbose, insulin and pioglitazone hydrochloride.

The definitions of respective substituents and respective moieties used in the present specification are as follows.

In the present specification, "$C_{1-6}$" means that the carbon number is 1 to 6.

The "halogen atom" is a fluorine atom, a chlorine atom, a bromine atom or an iodine atom, with preference given to a fluorine atom and a chlorine atom.

The "lower alkyl group" is a linear or branched chain alkyl group having 1 to 6 carbon atoms, which is exemplified by methyl group, ethyl group, propyl group, isopropyl group, butyl group, isobutyl group, sec-butyl group, tert-butyl group, pentyl group, isopentyl group, neopentyl group, tert-pentyl group, 1-ethylpropyl group and hexyl group. Preferred is a linear or branched chain alkyl group having 1 to 4 carbon atoms.

Preferably, it is a $C_{1-4}$ alkyl group for $R^1$, $R^2$, $R^3$, $R^4$, $R^5$, $R^7$, $R^9$, $R^{10}$, $R^{11}$, $R^{12}$, $R^{13}$, $R^{14}$, $R^{15}$, $R^{18}$ and $R^{19}$, and a $C_{1-6}$ alkyl group for $R^8$, $R^{16}$ and $R^{17}$.

The "lower haloalkyl group" is a haloalkyl group wherein a linear or branched chain alkyl group having 1 to 6 carbon atoms is substituted by the above-defined "halogen atom", which is exemplified by fluoromethyl group, difluoromethyl group, trifluoromethyl group, bromomethyl group, chloromethyl group, 1,2-dichloromethyl group, 2,2-dichloromethyl group, 2,2,2-trifluoroethyl group and the like. Preferred is a linear or branched chain haloalkyl group having 1 to 4 carbon atoms, and particularly preferred is trifluoromethyl group.

Preferably, it is a $C_{1-4}$ haloalkyl group for $R^1$, $R^2$, $R^3$, $R^4$ and $R^5$.

The "lower alkylene group" is a linear or branched chain alkylene group having 1 to 6 carbon atoms, which is exemplified by methylene group, ethylene group, trimethylene group, propylene group, tetramethylene group, pentamethylene group, hexamethylene group and the like. Preferred is a linear or branched chain alkylene group having 1 to 4 carbon atoms and particularly preferred is methylene group.

Preferably, it is a $C_{1-4}$ alkylene group for $A^1$ and $A^2$.

The "lower alkoxy group" is a linear or branched chain alkoxy group having 1 to 6 carbon atoms, which is exemplified by methoxy group, ethoxy group, propoxy group, isopropoxy group, butoxy group, isobutoxy group, tert-butoxy group, pentyloxy group, hexyloxy group and the like. Preferred is a linear or branched chain alkoxy group having 1 to 4 carbon atoms.

Preferably, it is a $C_{1-4}$ alkoxy group for $R^1$, $R^2$, $R^3$, $R^4$ and $R^5$.

The "lower haloalkoxy group" is a haloalkoxy group wherein a linear or branched chain alkoxy group having 1 to 6 carbon atoms is substituted by the above-defined "halogen atom", which is exemplified by fluoromethyloxy group, difluoromethyloxy group, trifluoromethyloxy group, bromomethyloxy group, chloromethyloxy group, 1,2-dichloromethyloxy group, 2,2-dichloromethyloxy group, 2,2,2-trifluoroethyloxy group and the like. Preferred is a linear or branched chain haloalkoxy group having 1 to 4 carbon atoms, and particularly preferred is a trifluoromethyloxy group.

Preferably, it is a $C_{1-4}$ haloalkoxy group for $R^1$, $R^2$, $R^3$ and $R^4$.

The "aryl group" is an aromatic hydrocarbon group having 6 to 14 carbon atoms, which is exemplified by phenyl group, naphthyl group, biphenylyl group (e.g., 2-biphenylyl group, 3-biphenylyl group, 4-biphenylyl group etc.), anthryl group and the like. Preferred are a phenyl group and a biphenylyl group, and more preferred is a phenyl group.

Preferably, it is a $C_{6-14}$ aryl group for $R^{16}$, $R^{17}$, B and Z.

The "aryloxy group" is an aryloxy group wherein the "aryl moiety" is the above-defined "aryl group", which is exemplified by phenoxy group, naphthyloxy group, biphenylyloxy group (e.g., 2-biphenylyloxy group, 3-biphenylyloxy group, 4-biphenylyloxy group), anthryloxy group and the like. Preferred are a phenoxy group and a biphenylyloxy group, and more preferred is a phenoxy group.

The "aralkyloxy group" is an aralkyloxy group wherein the "aryl moiety" is the above-defined "aryl group" and the "alkyl moiety" is a linear or branched chain alkyl group having 1 to 4 carbon atoms, which is exemplified by benzyloxy group, phenethyloxy group, 3-phenylpropyloxy group and the like. Preferred is a benzyloxy group.

Preferably, it is a $C_{6-14}$ aryl $C_{1-4}$ alkyloxy group for $R^1$, $R^2$, $R^3$ and $R^4$.

The "lower cycloalkyl group" is a cycloalkyl group having 3 to 7 carbon atoms, which is exemplified by cyclopropyl group, cyclobutyl group, cyclopentyl group, cyclohexyl group and cycloheptyl group. Preferred is a cycloalkyl group having 5 to 7 carbon atoms, and particularly preferred is a cyclohexyl group.

Preferably, it is a $C_{3-7}$ cycloalkyl group for Z.

The "lower cycloalkylalkyloxy group" is a cycloalkylalkyloxy group wherein the "cycloalkyl moiety" is the above-defined "lower cycloalkyl group" and the "alkyl moiety" is the above-defined "lower alkyl group", which is exemplified by cyclopropylmethyloxy group, cyclobutylmethyloxy group, cyclopentylmethyloxy group, cyclohexylmethyloxy group, cycloheptylmethyloxy group, 2-cyclopropylethyloxy group, 2-cyclobutylethyloxy group, 2-cyclopentylethyloxy group, 2-cyclohexylethyloxy group, 2-cycloheptylethyloxy group, 3-cyclohexylpropyloxy, 4-cyclohexylbutyloxy group and the like. Preferred is a $C_{3-7}$ cycloalkyl $C_{1-4}$ alkyloxy group, more preferred is a $C_{5-7}$ cycloalkyl $C_{1-4}$ alkyloxy group, and particularly preferred is a cyclohexyl $C_{1-4}$ alkyloxy group.

Preferably, it is a $C_{5-7}$ cycloalkyl $C_{1-4}$ alkyloxy group for $R^1$, $R^2$, $R^3$ and $R^4$.

The "lower alkenyl group" is a linear or branched chain alkenyl group having 2 to 6 carbon atoms, which is exemplified by vinyl group, 1-propenyl group, allyl group, 1-methyl-2-propenyl group, 1-butenyl group, 2-butenyl group, 3-butenyl group, 1-pentenyl group, 2-pentenyl group, 1-hexenyl group, 2-hexenyl group and the like. Preferred is a linear or branched chain alkenyl group having 2 to 4 carbon atoms.

Preferably, it is a $C_{2-4}$ alkenyl group for $R^{13}$.

The "lower alkylsulfonyl group" is an alkylsulfonyl group wherein the "alkyl moiety" is the above-defined "lower alkyl group", which is exemplified by methylsulfonyl group, ethylsulfonyl group, propylsulfonyl group, isopropylsulfonyl group, butylsulfonyl group, isobutylsulfonyl group, sec-butylsulfonyl group, tert-butylsulfonyl group, pentylsulfonyl group, isopentylsulfonyl group, tert-pentylsulfonyl group, hexylsulfonyl group and the like. Preferred is a $C_{1-4}$ alkylsulfonyl group.

Preferably, it is a $C_{1-4}$ alkylsulfonyl group for $R^{13}$.

The "lower alkylcarbonyl group" is an alkylcarbonyl group wherein the "alkyl moiety" is the above-defined "lower alkyl group", which is exemplified by acetyl group, propionyl group, butyryl group, isobutyl group, valeryl group, isovaleryl group, pivaloyl group, pentanoyl group, hexanoyl group and the like. Preferred is a $C_{1-4}$ alkylcarbonyl group wherein the "alkyl moiety" is a linear or branched chain alkyl group having 1 to 4 carbon atoms.

Preferably, it is a $C_{1-4}$ alkylcarbonyl group for $R^{13}$.

When R is a group represented by —COOR$^7$ or —X$^1$-A$^1$-COOR$^7$, and R$^7$ is a hydrogen atom, this carboxy group may form a salt. As the salt, alkali metal salts (e.g., potassium salt, sodium salt etc.), alkaline earth metal salts (e.g., calcium salt, magnesium salt etc.) and the like can be mentioned. Preferred is an alkali metal salt.

The tetrazole ring in the tetrazolyl group for R may form an alkali metal salt. As such alkali metal salt, potassium salt, sodium salt and the like can be mentioned.

The "lower cycloalkane" that may be formed by R$^9$ and R$^{10}$ together with a carbon atom bonded thereto is cycloalkane having 3 to 7 carbon atoms, which is exemplified by cyclopropane, cyclobutane, cyclopentane, cyclohexane and cycloheptane. Preferred is cycloalkane having 5 to 7 carbon atoms, and particularly preferred is cyclopentane or cyclohexane.

The "5- to 7-membered hetero ring optionally further having at least one hetero atom selected from the group consisting of nitrogen atom, oxygen atom and sulfur atom" that may be formed by R$^9$ and R$^{10}$ together with a carbon atom bonded thereto is preferably a "saturated 5- to 7-membered hetero ring optionally further having 1 to 3 hetero atoms selected from the group consisting of nitrogen atom, oxygen atom and sulfur atom", which is exemplified by tetrahydropyran, thiane and the like, particularly preferably tetrahydropyran.

The "aromatic heterocyclic group" for B is a "monocyclic or fused 5- to 14-membered aromatic heterocyclic group containing 1–3 hetero atoms selected from the group consisting of nitrogen atom, oxygen atom and sulfur atom", which is exemplified by furyl group, thienyl group, pyrrolyl group, oxazolyl group, isooxazolyl group, thiazolyl group, isothiazolyl group, imidazolyl group, pyrazolyl group, pyridyl group, pyridazinyl group, pyrimidinyl group, pyrazinyl group, indolyl group, isoindolyl group, benzofuranyl group, benzothienyl group, benzoimidazolyl group, benzothiazolyl group, benzoxazolyl group, indolizinyl group, quinolyl group, isoquinolyl group, quinazolinyl group, cinnolinyl group, quinoxalinyl group, phthalazinyl group, acrydinyl group, phenazinyl group, naphthyridinyl group and the like. Preferred is a "monocyclic or fused 5- to 10-membered aromatic heterocyclic group containing 1 to 3 hetero atoms selected from the group consisting of nitrogen atom, oxygen atom and sulfur atom", and furyl group, thienyl group, pyrrolyl group, oxazolyl group, isooxazolyl group, thiazolyl group, isothiazolyl group, imidazolyl group, pyrazolyl group, pyridyl group, pyridazinyl group, pyrimidinyl group, pyrazinyl group, indolyl group, isoindolyl group, benzofuranyl group, benzothienyl group, benzoimidazolyl group, benzothiazolyl group, benzoxazolyl group and the like can be mentioned. Particularly preferred are thiazolyl group, pyridyl group, benzothiazolyl group, benzoimidazolyl group and benzoxazolyl group.

The "lower cycloalkylalkyloxy group" for R$^1$, R$^2$, R$^3$ and R$^4$ is optionally substituted by 1 to 3 substituents selected from the following. As such substituent, halogen atom, $C_{1-4}$ alkyl group, $C_{1-4}$ haloalkyl group, $C_{1-4}$ alkoxy group, carboxy group, hydroxyl group, cyano group, nitro group, amino group, alkoxycarbonyl group (alkoxy moiety has 1 to 4 carbon atoms) and the like can be mentioned.

The "optionally substituted lower cycloalkylalkyloxy group" for R$^1$, R$^2$, R$^3$ and R$^4$ is preferably 2-cyclohexylethyloxy group.

The "aralkyloxy group" for R$^1$, R$^2$, R$^3$ and R$^4$ is optionally substituted by 1 to 3 substituents selected from the following. As such substituent, halogen atom, $C_{1-4}$ alkyl group, $C_{1-4}$ haloalkyl group, $C_{1-4}$ alkoxy group, carboxy group, hydroxyl group, cyano group, nitro group, amino group, alkoxycarbonyl (alkoxy moiety has 1 to 4 carbon atoms) group and the like can be mentioned. Preferable substituent is carboxy group.

The "optionally substituted aralkyloxy group" for R$^1$, R$^2$, R$^3$ and R$^4$ is preferably benzyloxy group, carboxybenzyloxy group and the like.

The "lower alkyl group" for R$^8$ is optionally substituted by a substituent selected from the group consisting of a lower alkoxy group, an aryloxy group, —N(R$^{11}$)(R$^{12}$) (R$^{11}$ and R$^{12}$ are each independently a hydrogen atom or a lower alkyl group or may form, together with a nitrogen atom bonded thereto, a 5- to 7-membered hetero ring optionally further having at least one hetero atom selected from the group consisting of nitrogen atom, oxygen atom and sulfur atom), a carboxy group, a lower cycloalkyl group and an optionally substituted aryl group.

The "optionally substituted aryl group" which is a substituent on the "lower alkyl group" for R$^8$ is optionally substituted by 1 to 3 substituents selected from the following. As such substituent, halogen atom, $C_{1-4}$ alkyl group, $C_{1-4}$ haloalkyl group, $C_{1-4}$ alkoxy group, carboxy group, hydroxyl group, cyano group, nitro group, amino group, alkoxycarbonyl group (alkoxy moiety has 1 to 4 carbon atoms) and the like can be mentioned. Preferable substituents are halogen atom and $C_{1-4}$ haloalkyl group.

The "5- to 7-membered hetero ring optionally further having at least one hetero atom selected from the group consisting of nitrogen atom, oxygen atom and sulfur atom" that may be formed by R$^{11}$ and R$^{12}$ together with the nitrogen atom bonded thereto is preferably "a saturated or unsaturated 5- to 7-membered hetero ring optionally further having 1–3 hetero atoms selected from the group consisting of nitrogen atom, oxygen atom and sulfur atom", which is exemplified by a hetero ring selected from the group consisting of

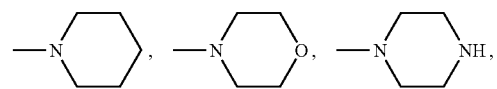

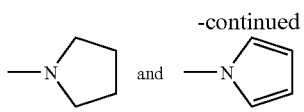

particularly preferably

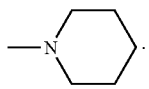

The "lower alkyl group" for $R^{13}$ is optionally substituted by a substituent selected from the group consisting of $C_{3-7}$ cycloalkyl group, optionally substituted aryl group, optionally substituted heterocyclic group and hydroxyl group.

The "optionally substituted aryl group" which is a substituent on the "lower alkyl group" for $R^{13}$ is optionally substituted by 1 to 3 substituents selected from the following. As such substituent, halogen atom, $C_{1-4}$ alkyl group, $C_{1-4}$ haloalkyl group, $C_{1-4}$ alkoxy group, carboxy group, hydroxyl group, cyano group, nitro group, amino group, alkoxycarbonyl group (alkoxy moiety has 1 to 4 carbon atoms) and the like can be mentioned. Preferable substituent is a halogen atom or $C_{1-4}$ haloalkyl group.

The "optionally substituted heterocyclic group" which is a substituent on the "lower alkyl group" for $R^{13}$ is preferably a "saturated or unsaturated 5- to 7-membered heterocyclic group containing 1 to 3 hetero atoms selected from the group consisting of nitrogen atom, oxygen atom and sulfur atom", which is exemplified by furyl group, thienyl group, pyrrolyl group, oxazolyl group, isooxazolyl group, thiazolyl group, isothiazolyl group, imidazolyl group, pyrazolyl group, pyridyl group, pyridazinyl group, pyrimidinyl group, pyrazinyl group, tetrahydrofuryl group, tetrahydrothienyl group, pyrrolidinyl group, pyrazolidinyl group, imidazolidinyl group, oxazolidinyl group, thiazolidinyl group, tetrahydropyranyl group, dioxanyl group, piperidinyl group, piperazinyl group, morpholinyl group and the like, with preference given to tetrahydropyranyl group.

The "optionally substituted hetero ring" which is a substituent on the "lower alkyl group" for $R^{13}$ is optionally substituted by 1 to 3 substituents selected from the following. As such substituent, halogen atom, $C_{1-4}$ alkyl group, $C_{1-4}$ haloalkyl group, $C_{1-4}$ alkoxy group, carboxy group, hydroxyl group, cyano group, nitro group, amino group, alkoxycarbonyl group (alkoxy moiety has 1 to 4 carbon atoms) and the like can be mentioned.

The "lower alkylcarbonyl group" for $R^{13}$ is optionally substituted by a hydroxyl group or a lower alkoxy group.

As the lower alkoxy group which is a substituent on the "lower alkylcarbonyl group" for $R^{13}$, the above-defined "lower alkoxy group" can be mentioned, with preference given to $C_{1-4}$ alkoxy group.

The "lower cycloalkane" that may be formed by $R^{18}$ and $R^{19}$ together with a carbon atom bonded thereto is cycloalkane having 3 to 7 carbon atoms, which is exemplified by cyclopropane, cyclobutane, cyclopentane, cyclohexane and cycloheptane. It is preferably cycloalkane having 5 to 7 carbon atoms, and particularly preferably cyclopentane or cyclohexane.

The "5- to 7-membered hetero ring optionally further having at least one hetero atom selected from the group consisting of nitrogen atom, oxygen atom and sulfur atom" that may be formed by $R^{18}$ and $R^{19}$ together with a carbon atom bonded thereto is preferably, a "saturated 5- to 7-membered hetero ring optionally further having 1 to 3 hetero atoms selected from the group consisting of nitrogen atom, oxygen atom and sulfur atom", which is exemplified by tetrahydropyran, thiane and the like, particularly preferably tetrahydropyran.

The lower alkylene group for $A^2$ is optionally substituted by a lower cycloalkyl group. As such lower cycloalkyl group, cycloalkyl group having 3 to 7 carbon atoms can be mentioned, which is exemplified by cyclopropyl group, cyclobutyl group, cyclopentyl group, cyclohexyl group and cycloheptyl group. It is preferably a cycloalkyl group having 5 to 7 carbon atoms, particularly preferably a cyclohexyl group.

The "lower alkylene group optionally substituted by a lower cycloalkyl group" for $A^2$ is preferably a "$C_{1-4}$ alkylene group optionally substituted by $C_{3-7}$ cycloalkyl group", more preferably,

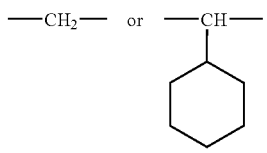

The "lower cycloalkyl group" for Z is preferably a $C_{3-7}$ cycloalkyl group, more preferably a cyclopentyl group or a cyclohexyl group, still more preferably a cyclohexyl group.

The "lower cycloalkyl group" for Z may be substituted by (a) a halogen atom, (b) a $C_{1-6}$ alkyl group, (c) a $C_{1-4}$ haloalkyl group, (d) a carboxy group, (e) a $C_{3-7}$ cycloalkyl group, (f) a $C_{1-4}$ alkoxy group, (g) a heterocyclic group optionally substituted by a $C_{1-4}$ alkyl group or (h) a phenyl group, wherein said phenyl group is further optionally substituted by 1 to 5 (preferably 1 to 3) halogen atoms. Such substituent of the "lower cycloalkyl group" is preferably a phenyl group optionally substituted by 1 to 3 halogen atoms, more preferably a phenyl group.

The "aryl group" for Z is preferably a phenyl group or a biphenylyl group (e.g., 2-biphenylyl group, 3-biphenylyl group, 4-biphenylyl group), more preferably a phenyl group.

The "aryl group" for Z is optionally substituted by 1 to 5 (preferably 1 to 3) substituents selected from the following;
(a) a heterocyclic group optionally substituted by a substituent selected from the group consisting of a lower alkyl group and a lower alkylcarbonyl group,
(b) a lower cycloalkyl group optionally substituted by a substituent selected from the group consisting of a hydroxyl group, an oxo group, a halogen atom and a lower alkyl group,
(c) a carboxy group,
(d) a halogen atom,
(e) an alkyl group,
(f) a lower haloalkyl group,
(g) a lower alkylamino group,
(h) a di(lower alkyl)amino group,
(i) a lower alkylthio group and
(j) a lower alkoxy group.

The "heterocyclic group" of the "heterocyclic group optionally substituted by a substituent selected from the group consisting of lower alkyl group and lower alkylcarbonyl group" is preferably a "saturated or unsaturated 5- to 7-membered heterocyclic group containing 1 to 3 hetero atoms selected from the group consisting of nitrogen atom, oxygen atom and sulfur atom", which is exemplified by furyl group, thienyl group, pyrrolyl group, oxazolyl group, isooxazolyl group, thiazolyl group, isothiazolyl group, imidazolyl group, pyrazolyl group, pyridyl group, pyridazinyl group, pyrimidinyl group, pyrazinyl group, tetrahydrofuryl group, tetrahydrothienyl group, pyrrolidinyl group, pyrazolidinyl group, imidazolidinyl group, oxazolidinyl group, thiazolidinyl group, tetrahydropyranyl group, dioxanyl group, piperidinyl group, piperazinyl group, morpholinyl group and the like. It is preferably piperidinyl group, morpholinyl group, piperazinyl group, pyrrolidinyl group, pyrrolyl group or tetrahydropyranyl group, more preferably a group selected from the group consisting of

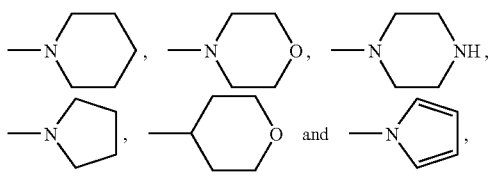

particularly preferably a group selected from the group consisting of

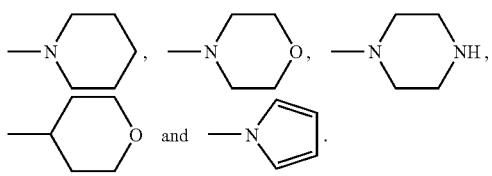

The substituent on said "heterocyclic group" is preferably a $C_{1-4}$ alkyl group or a $C_{1-4}$ alkylcarbonyl group (alkyl moiety has 1 to 4 carbon atoms).

The "lower cycloalkyl" of the "lower cycloalkyl group optionally substituted by a substituent selected from the group consisting of hydroxyl group, an oxo group, a halogen atom and lower alkyl group" is preferably $C_{3-7}$ cycloalkyl group, more preferably cyclohexyl group. The "lower cycloalkyl group" is optionally substituted by 1 to 5 (preferably 1 to 3) substituents selected from the group consisting of a hydroxyl group, an oxo group, a halogen atom and a lower alkyl group. The substituent on the "lower cycloalkyl group" is preferably a hydroxyl group, an oxo group, a halogen atom or a $C_{1-4}$ alkyl group.

As the "halogen atom" which is a substituent on "aryl group" for Z, the above-defined "halogen atom" can be preferably mentioned, such as fluorine atom, chlorine atom and bromine atom.

The "alkyl group" which is a substituent on the "aryl group" for Z is preferably a linear or branched chain alkyl group having 1 to 8 carbon atoms, which is exemplified by methyl group, ethyl group, propyl group, isopropyl group, butyl group, isobutyl group, sec-butyl group, tert-butyl group, pentyl group, isopentyl group, neopentyl group, tert-pentyl group, 1-ethylpropyl group, hexyl group, heptyl group, 1-propylbutyl group, octyl group and the like.

The "lower haloalkyl group" which is a substituent on the "aryl group" for Z is the above-defined "lower haloalkyl group", which is preferably a $C_{1-4}$ haloalkyl group.

The "lower alkylamino group" which is a substituent on the "aryl group" for Z is an alkylamino group wherein the "alkyl moiety" is the above-defined "lower alkyl group", which is exemplified by methylamino group, ethylamino group, propylamino group, isopropylamino group, butylamino group, isobutylamino group, sec-butylamino group, tert-butylamino group, pentylamino group, isopentylamino group, neopentylamino group, tert-pentylamino group, hexylamino group and the like. It is preferably a $C_{1-4}$ alkylamino group.

The "di(lower alkyl)amino group" which is a substituent on the "aryl group" for Z is dialkylamino group wherein the "alkyl moiety" is the above-defined "lower alkyl group", which is exemplified by dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like. Preferred is a di($C_{1-4}$ alkyl)amino group.

The "lower alkylthio group" which is a substituent on the "aryl group" for Z is alkylthio group wherein the "alkyl moiety" is the above-defined "lower alkyl group", which is exemplified by methylthio group, ethylthio group, propylthio group, isopropylthio group, butylthio group, isobutylthio group, sec-butylthio group, tert-butylthio group, pentylthio group, isopentylthio group, neopentylthio group, tert-pentylthio group, hexylthio group and the like. It is preferably a $C_{1-4}$ alkylthio group.

The "lower alkoxy group" which is a substituent on the "aryl group" for Z is the above-defined "lower alkoxy group", preferably a $C_{1-4}$ alkoxy group.

The "aromatic heterocyclic group" for Z is preferably a "monocycle or fused 5- to 10-membered aromatic heterocyclic group containing 1–3 hetero atoms selected from the group consisting of nitrogen atom, oxygen atom and sulfur atom", and furyl group, thienyl group, pyrrolyl group, oxazolyl group, isooxazolyl group, thiazolyl group, isothiazolyl group, imidazolyl group, pyrazolyl group, pyridyl group, pyridazinyl group, pyrimidinyl group, pyrazinyl group, indolyl group, isoindolyl group, benzofuranyl group, benzothienyl group, benzoimidazolyl group, benzothiazolyl group, benzoxazolyl group and the like can be mentioned. It is particularly preferably a thiazolyl group or a pyridyl group.

The "aromatic heterocyclic group" for Z is optionally substituted by 1 to 5 (preferably 1 to 3) substituents selected from the following;
(a) a heterocyclic group optionally substituted by $C_{1-4}$ alkyl group,
(b) a $C_{1-6}$ alkyl group,
(c) an aryl group optionally substituted by a halogen atom or a $C_{1-4}$ haloalkyl group,
(d) a halogen atom,
(e) a $C_{1-4}$ haloalkyl group,
(f) a carboxy group,
(g) a $C_{3-7}$ cycloalkyl group and
(h) a $C_{1-4}$ alkoxy group.

Such substituent is preferably (a) a heterocyclic group, (b) a $C_{1-6}$ alkyl group or (c) an aryl group optionally substituted by a halogen atom or a $C_{1-4}$ haloalkyl group.

The "heterocyclic group" which is a substituent on the "aromatic heterocyclic group" for Z is preferably a "saturated or unsaturated 5- to 7-membered heterocyclic group containing 1 to 3 hetero atoms selected from the group consisting of nitrogen atom, oxygen atom and sulfur atom", which is exemplified by furyl group, thienyl group, pyrrolyl group, oxazolyl group, isooxazolyl group, thiazolyl group, isothiazolyl group, imidazolyl group, pyrazolyl group, pyridyl group, pyridazinyl group, pyrimidinyl group, pyrazinyl group, tetrahydrofuryl group, tetrahydrothienyl group, pyrrolidinyl group, pyrazolidinyl group, imidazolidinyl group, oxazolidinyl group, thiazolidinyl group, tetrahydropyranyl group, dioxanyl group, piperidinyl group, piperazinyl group, morpholinyl group and the like. It is preferably piperidinyl group, morpholinyl group, piperazinyl group, tetrahydropyranyl group, pyrrolidinyl group or pyrrolyl group, more preferably a group selected from the group consisting of

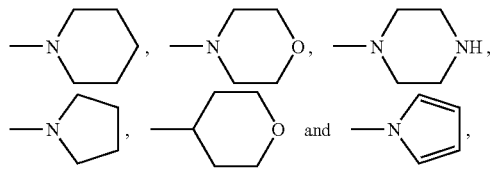

particularly preferably

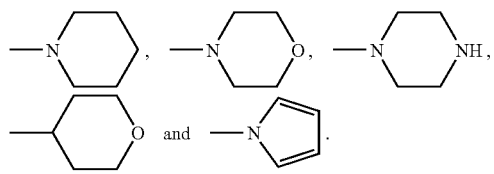

The "aryl group optionally substituted by a halogen atom or a $C_{1-4}$ haloalkyl group" which is a substituent on the "aromatic heterocyclic group" for Z is preferably a "phenyl group optionally substituted by a halogen atom or a $C_{1-4}$ haloalkyl group".

The "piperazinyl group" for Z is optionally substituted by 1 to 5 (preferably 1 to 3) substituents selected from the following;
(a) a phenyl group,
(b) a phenyl lower alkyl group,
(c) a benzoyl group optionally substituted by a halogen atom and
(d) a phenyl lower alkoxycarbonyl group.

The "phenyl lower alkyl group" which is a substituent on the "piperazinyl group" for Z is a phenylalkyl group wherein the "alkyl moiety" is the above-defined "lower alkyl group", which is exemplified by benzyl group, phenethyl group, 1-phenylethyl group, 3-phenylpropyl group and the like. Preferably, it is a phenyl $C_{1-4}$ alkyl group.

The "benzoyl group optionally substituted by a halogen atom" which is a substituent on the "piperazinyl group" for Z is preferably a benzoyl group optionally substituted by 1 to 5 the above-defined "halogen atoms", which is exemplified by chlorobenzoyl group, bromobenzoyl group and the like.

The "phenyl lower alkoxycarbonyl group" which is a substituent on the "piperazinyl group" for Z is a phenylalkoxycarbonyl group wherein the "alkoxy moiety" is the above-defined "lower alkoxy group", which is exemplified by a benzyloxycarbonyl group and the like. Preferably, it is a phenyl $C_{1-4}$ alkoxycarbonyl group.

In the formula [I], preferable substituents are as follows.
W is preferably a sulfur atom.
R is preferably —COOR$^7$ wherein R$^7$ is a hydrogen atom.

R$^1$, R$^2$, R$^3$ and R$^4$ are preferably hydrogen atoms.
A is preferably —(CH$_2$)$_m$—X—
wherein
X is a group represented by —N(R$^8$)— wherein R$^8$ is a hydrogen atom or a $C_{1-6}$ alkyl group, wherein said $C_{1-6}$ alkyl group is optionally substituted by a substituent selected from the group consisting of a $C_{1-4}$ alkoxy group, an aryloxy group, —N(R$^{11}$)(R$^{12}$) (R$^{11}$ and R$^{12}$ are each independently a hydrogen atom or a $C_{1-4}$ alkyl group or may form, together with a nitrogen atom bonded thereto, a 5- to 7-membered hetero ring optionally further having at least one hetero atom selected from the group consisting of nitrogen atom, oxygen atom and sulfur atom), a carboxy group, a $C_{3-7}$ cycloalkyl group and an optionally substituted aryl group, and
m is 0 or an integer of 1 to 3.

B is preferably a phenyl group, a thiazolyl group, a pyridyl group, a benzothiazolyl group, a benzoimidazolyl group or a benzoxazolyl group, more preferably a phenyl group.

R$^5$ is preferably a hydrogen atom.
Z is preferably
(1) a $C_{3-7}$ cycloalkyl group
(wherein said $C_{3-7}$ cycloalkyl group is optionally substituted by a phenyl group optionally substituted by a halogen atom),
(2) an aryl group
(wherein said aryl group is optionally substituted by a substituent selected from the group consisting of
(a) a heterocyclic group optionally substituted by a $C_{1-4}$ alkyl group or a $C_{1-4}$ alkylcarbonyl group,
(b) a $C_{3-7}$ cycloalkyl group optionally substituted by a substituent selected from the group consisting of a hydroxyl group, an oxo group, a halogen atom and a $C_{1-4}$ alkyl group,
(c) a carboxy group,
(d) a halogen atom,
(e) a $C_{1-8}$ alkyl group,
(f) a $C_{1-4}$ haloalkyl group,
(g) a $C_{1-4}$ alkylamino group,
(h) a di($C_{1-4}$ alkyl)amino group,
(i) a $C_{1-4}$ alkylthio group and
(j) a $C_{1-4}$ alkoxy group) or
(3) an aromatic heterocyclic group
(wherein said aromatic heterocyclic group is optionally substituted by a substituent selected from the group consisting of
(a) a heterocyclic group,
(b) a $C_{1-4}$ alkyl group and
(c) a phenyl group optionally substituted by a halogen atom or a $C_{1-4}$ haloalkyl group).

Z is more preferably an aryl group optionally substituted by a substituent selected from the group consisting of
(a) a heterocyclic group optionally substituted by a $C_{1-4}$ alkyl group or a $C_{1-4}$ alkylcarbonyl group,
(b) a $C_{3-7}$ cycloalkyl group optionally substituted by a substituent selected from the group consisting of a hydroxyl group, an oxo group, a halogen atom and a $C_{1-4}$ alkyl group,
(c) a carboxy group,
(d) a halogen atom,
(e) a $C_{1-8}$ alkyl group,
(f) a $C_{1-4}$ haloalkyl group,
(g) a $C_{1-4}$ alkylamino group,
(h) a di($C_{1-4}$ alkyl)amino group and
(i) a $C_{1-4}$ alkylthio group.

Z is further preferably a phenyl group substituted by a substituent selected from the group consisting of
(a) a cyclohexyl group or a cyclopentyl group optionally substituted by a substituent selected from the group consisting of a hydroxyl group, an oxo group, a halogen atom and a $C_{1-4}$ alkyl group,
(b) a heterocyclic group optionally substituted by a $C_{1-4}$ alkyl group or a $C_{1-4}$ alkylcarbonyl group (wherein said heterocyclic group is selected from the group consisting of a piperidinyl group, a morpholinyl group, a piperazinyl group, a tetrahydropyranyl group, a pyrrolidinyl group and a pyrrolyl group) and
(c) $C_{1-8}$ alkyl groups.

Z is particularly preferably a phenyl group substituted by a cyclohexyl group optionally substituted by a substituent selected from the group consisting of a hydroxyl group, an oxo group, a halogen atom and a $C_{1-4}$ alkyl group.

For $R^6$, Y is preferably —O—, —N($R^{13}$)— or —N($R^{14}$)—CO—
wherein
$R^{13}$ is a hydrogen atom, a $C_{1-4}$ alkyl group or a $C_{2-4}$ alkenyl group, wherein said $C_{1-4}$ alkyl group is optionally substituted by a substituent selected from the group consisting of a $C_{3-7}$ cycloalkyl group, an optionally substituted aryl group and an optionally substituted heterocyclic group,
$R^{14}$ is a hydrogen atom or a $C_{1-4}$ alkyl group, and s1 is 0 or 1.

$A^2$ is preferably a methylene group.

The "pharmaceutically acceptable salt" may be any salt as long as it forms a non-toxic salt with the compound represented by the above-mentioned formula [I], and can be obtained by reacting with inorganic acids such as hydrochloric acid, sulfuric acid, phosphoric acid, hydrobromic acid and the like; organic acids such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid and the like; inorganic bases such as sodium hydroxide, potassium hydroxide, calcium hydroxide, magnesium hydroxide, ammonium hydroxide and the like; organic bases such as methylamine, diethylamine, triethylamine, triethanolamine, ethylenediamine, tris(hydroxymethyl)methylamine, guanidine, choline, cinchonine, N-methyl-D-glucamine and the like; or amino acids such as lysin, histidine, arginine, alanine and the like. The present invention also encompasses water-containing product, hydrate and solvate of each compound.

The compound represented by the above-mentioned formula [I] contains various isomers. For example, E-form and Z-form are present as geometric isomers, and when an asymmetric carbon atom is present, enantiomer and diastereomer are present as stereoisomers based thereon. In some cases, a tautomer may be present. Accordingly, the present invention encompasses all of these isomers and mixtures thereof.

The present invention encompasses prodrug and metabolite of the compound of the formula [I].

A "prodrug" is a derivative of the compound of the present invention, which has a chemically or metabolically decomposable group, and, after administration to a living organism, restores to the original compound to show the inherent efficacy. It includes a complex free of covalent bond and salt.

For example, known ester derivatives can be used as prodrugs in the field of pharmaceutical drugs. To be specific, ester derivatives wherein R is a group represented by the following formula can be mentioned.

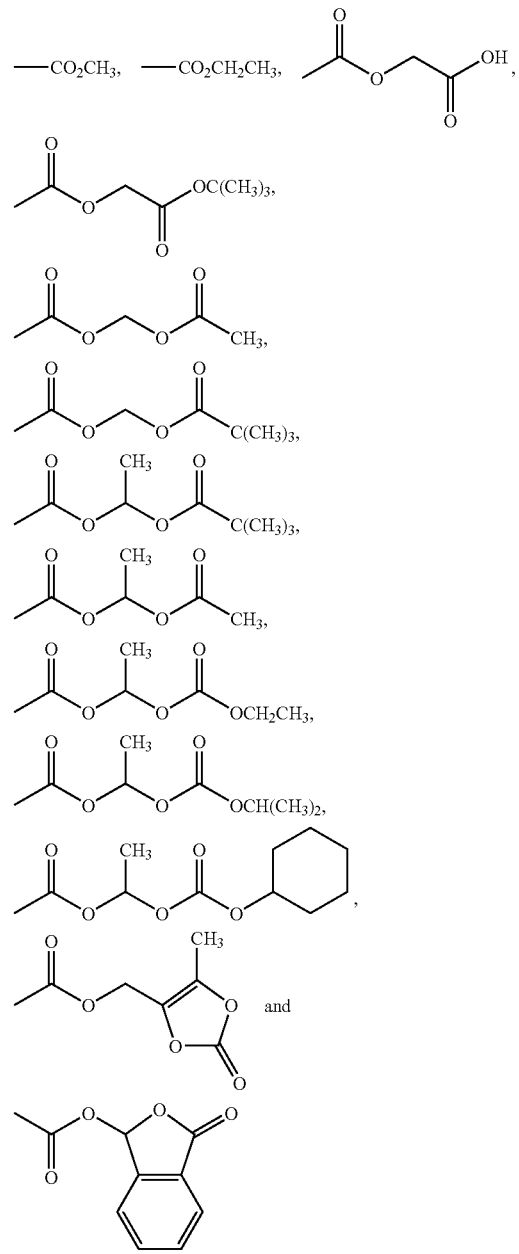

When the compound of the present invention is used as a pharmaceutical preparation, it is generally admixed with pharmaceutically acceptable carrier, excipient, diluent, extender, disintegrant, stabilizer, preservative, buffer, emulsifier, aromatic, coloring agent, sweetening agent, thickening agent, corrigent, dissolution aids and other additives, which are known per se and specifically exemplified by water, vegetable oil, alcohols such as ethanol, benzyl alcohol etc., polyethylene glycol, glycerol triacetate, gelatin, lactose, carbohydrate such as starch etc., magnesium stearate, talc, lanolin, vaseline and the like, and prepared into the form of tablet, pill, powder, granule, suppository, injection, eye drop, liquid, capsule, troche, aerosol, elixir, suspension, emulsion, syrup and the like by a conventional method, which can be administered systemically or topically, and orally or parenterally.

The dose of the compound of the present invention varies depending on the age, body weight, symptom, disease to be treated, administration method and the like, but it is generally administered in the range of 50 mg to 800 mg per dose for an adult once to several times a day.

The compound [I] of the present invention can be administered to mammals (human, mouse, rat, rabbit, dog, cat, bovine, pig, monkey etc.) as a PTP1B inhibitor, a drug for the prophylaxis or treatment of diabetes, a drug for the prophylaxis or treatment of diabetic complications (retinopathy, nephropathy, neuropathy, cardiac infarction and cerebral infarction based on arteriosclerosis, etc.), a drug for the prophylaxis or treatment of hyperlipidemia, a drug for the prophylaxis or treatment of obesity, neurodegenerative disease and the like or a drug for the prophylaxis or treatment of a disease mediated by PTP1B.

The compound [I] of the present invention can be administered to a mammal together with other therapeutic agents for diabetes for the purpose of prophylaxis or treatment of diabetes or diabetic complications. In the present invention, "therapeutic agents for diabetes" include therapeutic agents for diabetic complications. In addition, the compound [I] of the present invention can be administered to a mammal together with other therapeutic agents for hyperlipidemia for the purpose of prophylaxis or treatment of hyperlipidemia.

In the case of combined administration, the compound of the present invention can be administered simultaneously with a different therapeutic agent for diabetes or a different therapeutic drug for hyperlipidemia (hereinafter combination drug) or administered at certain time intervals. In the case of combined administration, a pharmaceutical composition containing the compound of the present invention and a combination drug can be administered. Alternatively, a pharmaceutical composition containing the compound of the present invention and a pharmaceutical composition containing a combination drug may be administered separately. The administration route of each pharmaceutical composition may be the same or different.

In the case of a combined administration, the compound of the present invention can be administered once to several times a day in the range of 50 mg to 800 mg per dose, or may be administered at a lower dose. A combination drug can be administered at a dose generally employed for the prophylaxis or treatment of diabetes or for the prophylaxis or treatment of hyperlipidemia, or may be administered at a lower dose.

As other therapeutic agents for diabetes to be used for the combined administration, insulin secretagogue, sulfonylurea, sulfonamide, biguanide, α glucosidase inhibitor, insulin preparation, insulin sensitizer and the like can be mentioned. For example, nateglide, glimepiride, glibenclamide, gliclazide, acetohexamide, tolbutamide, glyclopyramide, tolazamide, glybuzole, metformin hydrochloride, buformin hydrochloride, voglibose, acarbose, insulin, pioglitazone hydrochloride and the like can be used for combined administration with the compound of the present invention.

As other therapeutic drugs for hyperlipidemia to be used for the combined administration, statin drugs can be mentioned. For example, lovastatin, simvastatin, pravastatin, fluvastatin, atorvastatin, cerivastatin and the like can be used for combined administration with the compound of the present invention.

Now, one example of the production methods of the compounds used to practice the present invention is shown below. However, the production method of the compound of the present invention is not limited to the example.

Even in the absence of description in the production methods, a protecting group may be introduced into functional groups as necessary and deprotected at a suitable stage, the order of each production method and step is exchanged and the like to efficiently perform production.

The treatment after reaction in each step may be performed according to a method generally employed, and conventional methods such as isolation and purification, crystallization, recrystallization, silica gel chromatography, preparative HPLC and the like are appropriately selected, or used in combination.

Production Method 1

In this Production Method, compound [I] wherein W is a sulfur atom is produced.

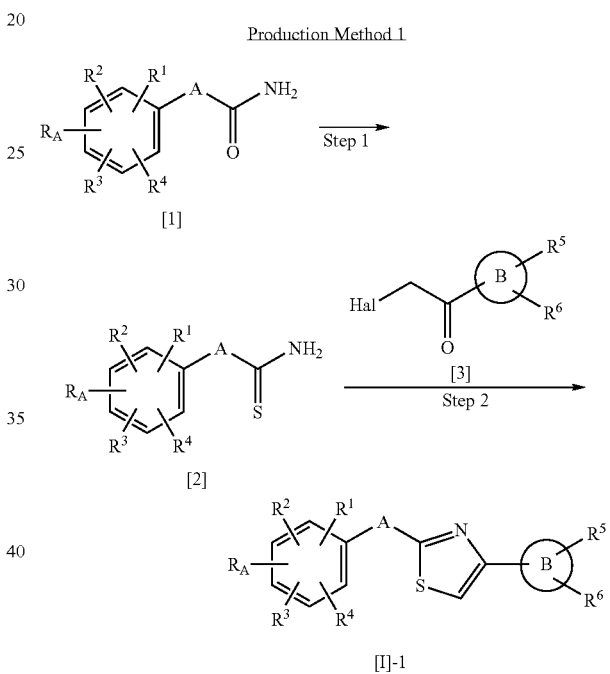

wherein $R_A$ is —COOR$^{7'}$ or —X$^1$-A$^1$-COOR$^{7'}$ (R$^{7'}$ is a lower alkyl group), Hal is a halogen atom such as a bromine atom, a chlorine atom and the like, and other symbols are as defined above.

Step 1

The compound [2] can be obtained by reacting compound [1] with a thiocarbonylation agent such as a Lawesson's reagent, phosphorus pentasulfide and the like in a solvent. As the solvent, tetrahydrofuran (THF), 1,2-dimethoxyethane (DME), toluene, xylene, chloroform, dichloromethane, dioxane and the like, or a mixed solvent thereof can be mentioned. The reaction temperature is preferably 50° C.–100° C.

Step 2

The compound [I]-1 can be obtained by reacting compound [2] with compound [3] in the presence or absence of a base in a solvent under heating. As the solvent, acetonitrile, alcohols (methanol, ethanol, isopropyl alcohol etc.), THF, DME, dioxane and the like, or a mixed solvent thereof can be mentioned. As the base, sodium hydrogen carbonate, potassium hydrogen carbonate and the like can be mentioned.

Production Method 2

In this Production Method, compound [I] wherein W is an oxygen atom is produced.

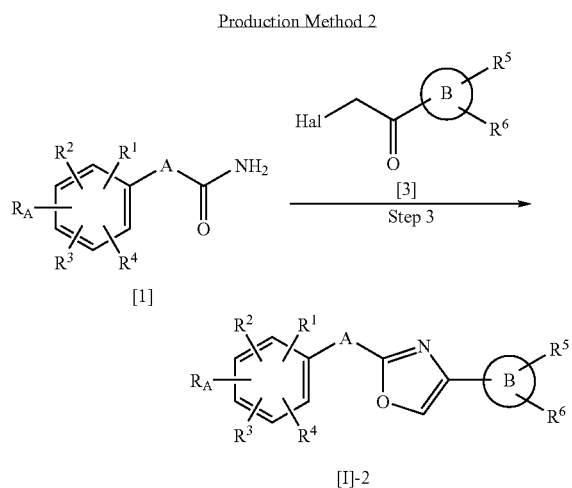

wherein each symbol is as defined above.

Step 3

The compound [I]-2 can be obtained by reacting compound [1] with compound [3] in a solvent under heating. As the solvent, acetonitrile, alcohols (methanol, ethanol, isopropyl alcohol etc.), xylene, toluene and the like, or a mixed solvent thereof can be mentioned.

Production Method 3

In this Production Method, compound [I] wherein W is a sulfur atom and A is —$(CH_2)_m$—$N(R^8)$— is produced.

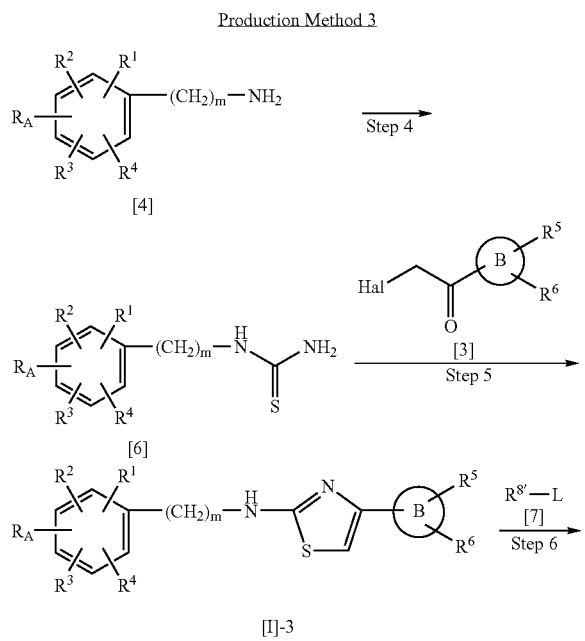

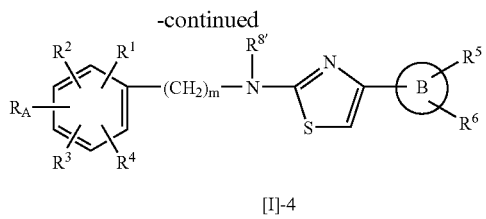

wherein $R^{8'}$, is —$SO_2R^{16}$ or a lower alkyl group, wherein said lower alkyl group is optionally substituted by a substituent selected from the group consisting of a lower alkoxy group, an aryloxy group, —$N(R^{11})(R^{12})$, a carboxy group, a lower cycloalkyl group and an optionally substituted aryl group, L is a leaving group such as an iodine atom, a bromine atom, a chlorine atom and the like, and other symbols are as defined above.

Step 4

The compound [6] can be obtained by reacting compound [4] with 1,1'-thiocarbonyldiimidazole, thiophosgene and the like in a solvent in the presence or absence of a base, then reacting with ammonia. As the solvent, chloroform, dichloromethane, dichloroethane, THF, DME, dioxane, toluene and the like, or a mixed solvent thereof can be mentioned. As the base, triethylamine, diisopropylethylamine, 1,8-diazabicyclo[5.4.0]undeca-7-ene (DBU), sodium hydride and the like can be mentioned. The reaction temperature is preferably −20° C.–50° C.

Step 5

The compound [I]-3 can be obtained by reacting compound [6] with compound [3] in a solvent under heating in the presence or absence of a base. As the solvent, acetonitrile, alcohols (methanol, ethanol, isopropyl alcohol etc.), THF, DME, dioxane and the like, or a mixed solvent thereof can be mentioned. As the base, sodium hydrogen carbonate, potassium hydrogen carbonate and the like can be mentioned.

Step 6

The compound [I]-4 can be obtained by reacting compound [I]-3 with compound [7] in a solvent in the presence of a base. As the solvent, dimethylformamide, dimethylacetamide, THF, DME, dioxane, hexamethylphosphoramide (HMPA), dimethyl sulfoxide (DMSO) and the like, or a mixed solvent thereof can be mentioned. As the base, sodium hydride, potassium carbonate, sodium carbonate and the like can be mentioned. The reaction temperature is preferably 0° C.–100° C.

Production Method 4

In this Production Method, compound [I] wherein $R^7$ is a hydrogen atom when R is —$COOR^7$ or —$X^1$-$A^1$-$COOR^7$, or a salt thereof is produced.

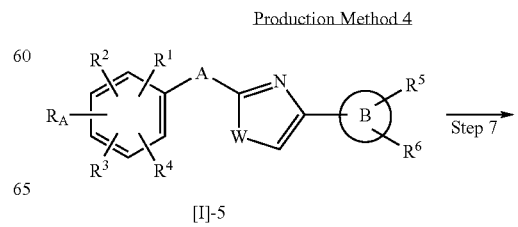

-continued

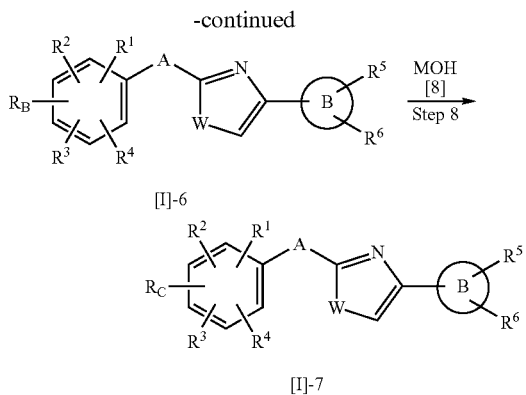

[I]-6

[I]-7 wherein $R_B$ is —COOH or —$X^1$-$A^1$-COOH, $R_C$ is —COOM or —$X^1$-$A^1$-COOM (M is an alkali metal), and other symbols are as defined above.

Step 7

The compound [I]-6 can be obtained by hydrolyzing compound [I]-5. Hydrolysis can be performed according to conventional methods. For example, a method comprises hydrolyzing in a solvent in the presence of an acid (including a Lewis acid) or a base can be mentioned. As the solvent, alcohols (methanol, ethanol, isopropyl alcohol etc.), tetrahydrofuran, dioxane, DME, N,N-dimethylformamide (DMF), DMSO, water and the like, or a mixed solvent thereof can be mentioned. As the acid, hydrochloric acid, trifluoroacetic acid, sulfuric acid and the like can be mentioned. As the base, alkali metal hydroxide (sodium hydroxide, potassium hydroxide etc.), potassium carbonate, sodium carbonate and the like can be mentioned. The reaction temperature is not particularly limited, and the reaction can be carried out under cooling to under heating.

Step 8

The compound [I]-7 can be obtained by reacting compound [I]-6 with alkali metal hydroxide [8], according to conventional methods. Alkali metal hydroxide includes sodium hydroxide, potassium hydroxide and the like. This Step can be conducted in a solvent. As the solvent, alcohols (methanol, ethanol etc.), tetrahydrofuran, dioxane, DME and the like, or a mixed solvent thereof can be mentioned. The reaction temperature is not particularly limited, and the reaction can be carried out under cooling to under heating.

Production Method 5

In this Production Method, compound [I] wherein R is a tetrazolyl group is produced.

Production Method 5

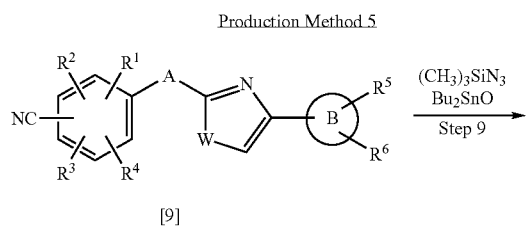

[9]

-continued

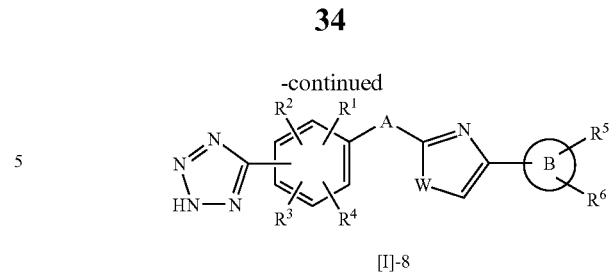

[I]-8 wherein each symbol is as defined above.

Step 9

The compound [I]-8 can be obtained by reacting compound [9] produced in the same manner as in the aforementioned Production Method 1–3 with trimethylsilylazide and dibutyltin oxide in a solvent. As the solvent, toluene, xylene, benzene and the like, or a mixed solvent thereof can be mentioned. The reaction temperature is preferably 50° C.–150° C.

Production Method 6

In this Production Method, compound [I] wherein $R^6$ is —N($R^{13}$)—$CH_2$-Z is produced.

Production Method 6

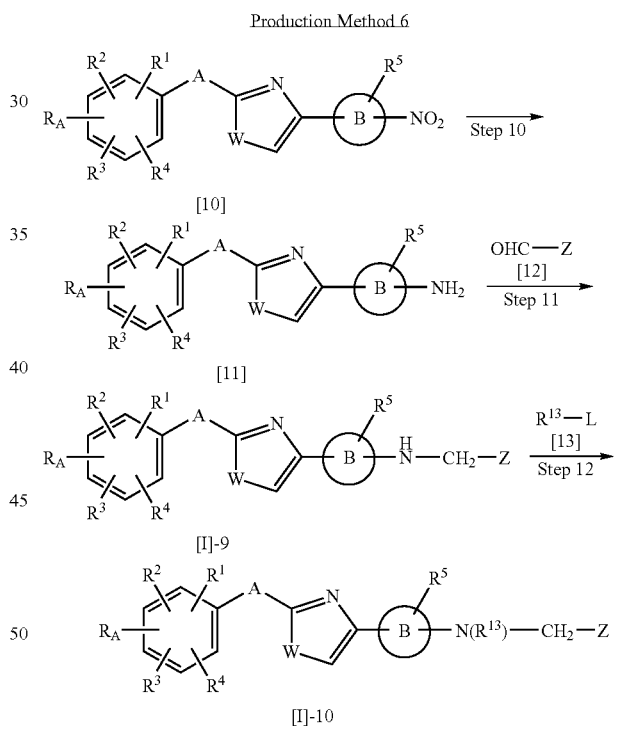

wherein each symbol is as defined above.

Step 10

The compound [11] can be obtained by reducing compound [10]. Reduction can be performed according to conventional methods. For example, compound [10] is subjected to catalytic reduction in a solvent in the presence of a catalyst under a hydrogen atmosphere. As the solvent, alcohols (methanol, ethanol, isopropyl alcohol etc.), tetrahydrofuran, acetic acid and the like can be mentioned. As the catalyst, palladium catalysts such as palladium-carbon etc. and the like can be mentioned.

Step 11

The compound [I]-9 can be obtained by reacting compound [11] with compound [12] in the presence of a reducing agent. As the reducing agent, sodium triacetoxyborohydride, sodium cyanoborohydride (NaBH₃CN) and the like can be mentioned. The reaction temperature is preferably 0° C.–40° C.

Step 12

The compound [I]-10 can be obtained by reacting compound [I]-9 with compound [13] in a solvent in the presence of a base. This reaction can be carried out in the same manner as in Step 6 of Production Method 3.

The Production Methods described in the present specification are examples of the production methods of the compounds of the present invention, and compounds other than those explained in the above can be also produced by combining conventional methods known in the field of organic synthetic chemistry.

EXAMPLES

The compound represented by the formula [I] and Production Methods of the present invention are explained in detail by referring to Production Examples and Examples, which are not to be construed as limitative.

Production Example 1

4-cyclohexylbenzaldehyde (1) 4-cyclohexylbenzyl alcohol

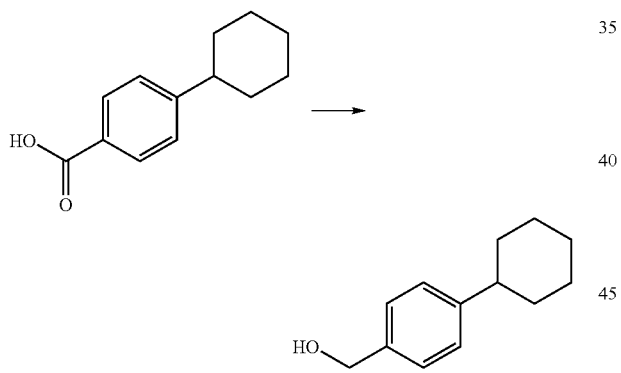

Under a nitrogen stream, tetrahydrofuran (1.2 L, 15.0 v/w) was added to 4-cyclohexylbenzoic acid (80.0 g, 0.382 mol) and then isobutyl chlorocarbonate (52.0 ml, 0.401 mol) was added. Triethylamine (56.0 ml, 0.401 mol) was added to the reaction mixture with stirring under ice-cooling and the mixture was stirred at the same temperature for 30 min. The resulting precipitate was collected by filtration. To a suspension of sodium borohydride (58.0 g, 1.53 mol) in tetrahydrofuran (160 ml, 2.0 v/w) prepared in a different reaction vessel was carefully added the above-mentioned filtrate with stirring under ice-cooling under a nitrogen stream. After stirring at room temperature for 1.5 hr, distilled water (160 ml, 2.0 v/w) was added with stirring under ice-cooling. After stirring under ice-cooling for 20 min, 2N-hydrochloric acid (825 ml, 4.3 eq) was added. After stirring at room temperature for 30 min, the mixture was extracted with ethyl acetate (400 ml) and the organic layer was washed successively with distilled water (100 ml), 2N-aqueous sodium hydroxide solution (100 ml), distilled water (100 ml) and saturated brine (100 ml), and dried over magnesium sulfate (70 g). After filtration and solvent evaporation, the residue was dried in vacuo to give the title compound (63.8 g, yield 87.8%) as a white solid.

¹H-NMR (300 MHz, DMSO-d₆) δ 1.23–1.41(5H, m), 1.67–1.78(5H, m), 2.47(1H, m), 4.43(2H, s), 5.04(1H, brs), 7.15(2H, d, J=8.0 Hz), 7.21(2H, d, J=8.0 Hz).

(2) 4-cyclohexylbenzaldehyde

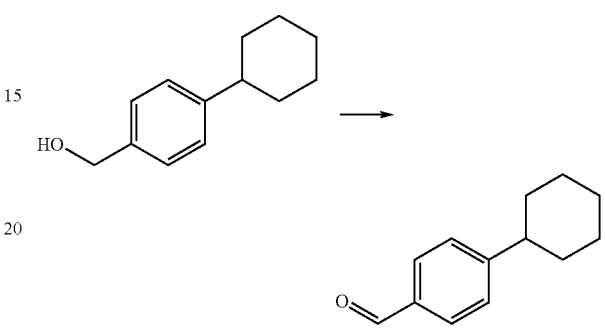

To a solution of 4-cyclohexylbenzyl alcohol (121.5 g, 0.639 mol) obtained in Production Example 1(1) in dimethyl sulfoxide (500 ml) was added triethylamine (249 ml, 1.79 mol). Pyridine-sulfur trioxide complex (163 g, 1.02 mol) was gradually added with stirring under ice-cooling, and the mixture was stirred at room temperature for 2 hr. Water (500 ml) was added dropwise to the reaction mixture with stirring under ice-cooling, and the mixture was extracted with a mixed solvent (1:1) of n-hexane and ethyl acetate, washed with saturated brine and dried over sodium sulfate. After filtration and solvent evaporation, the residue was dried in vacuo to give the title compound (112 g, yield 93.4%) as a colorless oil.

¹H-NMR (300 MHz, CDCl₃) δ 1.20–1.53(5H, m), 1.72–1.95(5H, m), 2.53–2.65(1H, m), 5.04(1H, brs), 7.37 (2H, d, J=8.2 Hz), 7.81(2H, d, J=8.2 Hz), 9.97(1H, s).

Example 1

4-(N-(4-(4-(N-(4-cyclohexylbenzyl)-N-methylamino)phenyl)-2-thiazolyl)-N-methylaminomethyl) benzoic acid (1) 1-(4-methoxycarbonylbenzyl)-2-thiourea

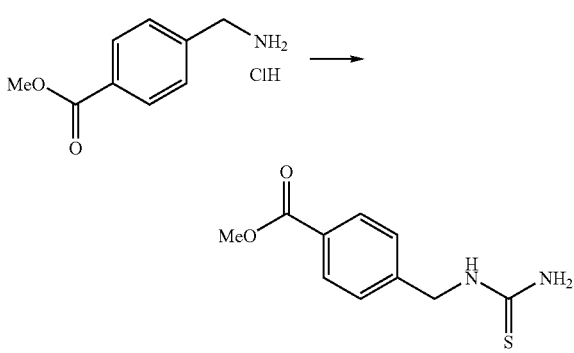

Under an argon atmosphere, to a suspension of methyl 4-aminomethylbenzoate hydrochloride (170.0 g, 0.843 mol)

in chloroform (850 ml, 5.0 v/w) were successively added 1,1'-thiocarbonyldiimidazole (purity 90%, 166.0 g, 0.843 mol) and triethylamine (123 ml, 0.885 mol). After stirring at room temperature for 3 hr, 28% aqueous ammonia (570 ml, 8.43 mol) and methanol (170 ml, 1.0 v/w) were added and the mixture was stirred overnight. n-Hexane (1700 ml, 10.0 v/w) and water (850 ml, 5.0 v/w) were successively added to the reaction mixture and the mixture was stirred at room temperature for 3 hrs. The precipitated crystals were collected by filtration, washed successively with n-hexane (500 ml) and water (500 ml) and dried in vacuo to give the title compound (172.5 g, yield 91.3%) as a colorless solid.

$^1$H-NMR (300 MHz, DMSO-$d_6$) δ 3.84(3H, s), 4.40(1H, brs), 4.72(2H, brs), 7.17(1H, brs), 7.41(2H, d, J=8.1 Hz), 7.93(2H, d, J=8.4 Hz), 8.07(1H, brs).

(2) methyl 4-((4-(4-nitrophenyl)-2-thiazolyl)aminomethyl)benzoate

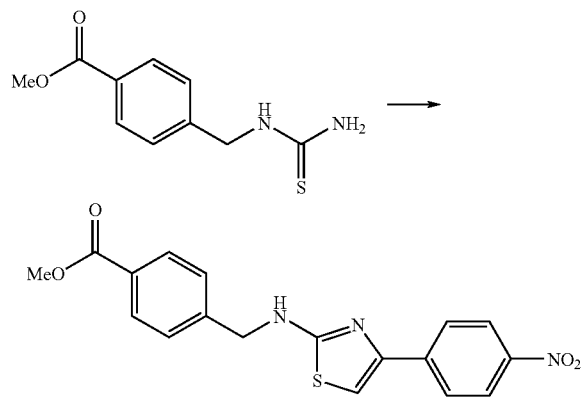

To a suspension of 1-(4-methoxycarbonylbenzyl)-2-thiourea (138.0 g, 0.554 mol) obtained in Example 1(1) in acetonitrile (1380 ml, 10.0 v/w) were successively added 2-bromo-4'-nitroacetophenone (124.1 g, 0.554 mol) and sodium bicarbonate (46.9 g, 0.559 mol), and the mixture was heated under reflux for 2 hr. After cooling to room temperature, water (1380 ml, 10.0 v/w) and n-hexane (690 ml, 5.0 v/w) were successively added and the mixture was stirred for 1 hr. The precipitated crystals were collected by filtration, washed successively with water (1000 ml) and n-hexane (500 ml) and dried in vacuo to give the title compound (183.9 g, yield 89.9%) as a yellow solid.

$^1$H-NMR (300 MHz, DMSO-$d_6$) δ 3.83(3H, s), 4.63(2H, d, J=5.9 Hz), 7.49(1H, s), 7.54(2H, d, J=8.1 Hz), 7.95(2H, d, J=8.1 Hz), 8.06(2H, d, J=9.3 Hz), 8.23(2H, d, J=6.0 Hz), 8.43(1H, t, J=5.9 Hz).

(3) methyl 4-(N-methyl-N-(4-(4-nitrophenyl)-2-thiazolyl)aminomethyl)benzoate

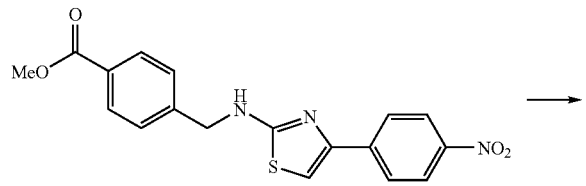

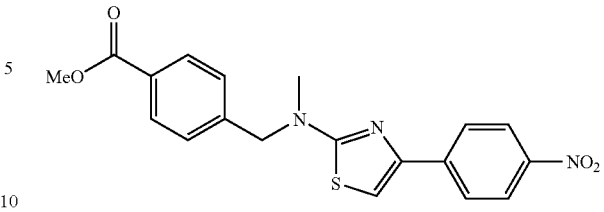

Under an argon atmosphere, to a suspension of sodium hydride (content 60%, 26.4 g, 0.661 mol) in N,N-dimethylformamide (530 ml, 2.5 v/w) were successively added dropwise a solution of methyl 4-((4-(4-nitrophenyl)-2-thiazolyl)aminomethyl)benzoate (212.4 g, 0.575 mol) obtained in Example 1(2) in N,N-dimethylformamide (743 ml, 3.5 v/w) and methyl iodide (41.2 ml, 0.661 mol) at 10° C. or below, and the mixture was stirred at room temperature for 2 hr. Sodium hydride (content 60%, 2.3 g, 0.057 mol) was added and the mixture was stirred at room temperature for 1 hr. The reaction mixture was added dropwise to water (2120 ml, 10.0 v/w) at 10° C. or below, and, after stirring at room temperature for 30 min., diisopropyl ether (848 ml, 4.0 v/w) was added and the mixture was stirred for 2 hr. The precipitated crystals were collected by filtration, washed successively with diisopropyl ether (424 ml) and water (424 ml) and dried in vacuo to give the title compound (201.9 g, yield 91.4%) as a yellow solid.

$^1$H-NMR (300 MHz, DMSO-$d_6$) δ 3.14(3H, s), 3.84(3H, s), 4.87(2H, s), 7.48(2H, d, J=8.3 Hz), 7.61(1H, s), 7.96(2H, d, J=8.3 Hz), 8.11(2H, d, J=9.0 Hz), 8.25(2H, d, J=9.0 Hz).

(4) methyl 4-(N-(4-(4-aminophenyl)-2-thiazolyl)-N-methylaminomethyl)benzoate

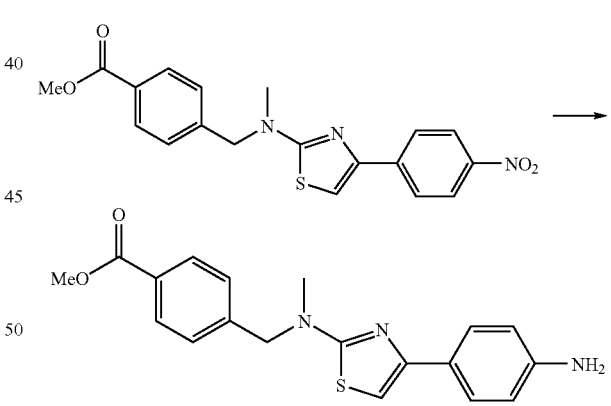

To a suspension of methyl 4-(N-methyl-N-(4-(4-nitrophenyl)-2-thiazolyl)aminomethyl)benzoate (200.0 g, 0.522 mol) obtained in Example 1(3) in a mixture of ethanol (800 ml, 4.0 v/w) and tetrahydrofuran (800 ml, 4.0 v/w) was added 10% palladium carbon (20.0 g) and the mixture was stirred overnight under a hydrogen atmosphere at 3 atm. The reaction mixture was filtered through celite and 10% palladium carbon (20.0 g) was added to the filtrate. The mixture was stirred under a hydrogen atmosphere at 3 atm for 3 hr. After celite filtration and solvent evaporation, toluene (800 ml) was added to the residue and the solvent was evaporated to give the title compound (182.5 g, yield 99.0%) as a yellow solid.

$^1$H-NMR (300 MHz, DMSO-d$_6$) δ 3.07(3H, s), 3.84(3H, s), 4.82(2H, s), 5.18(2H, br), 6.54(2H, d, J=8.6 Hz), 6.78 (1H, s), 7.45(2H, d, J=8.3 Hz), 7.52(2H, d, J=8.5 Hz), 7.95(2H, d, J=8.2 Hz).

(5) methyl 4-(N-(4-(4-(4-cyclohexylbenzylamino)phenyl)-2-thiazolyl)-N-methylaminomethyl)benzoate

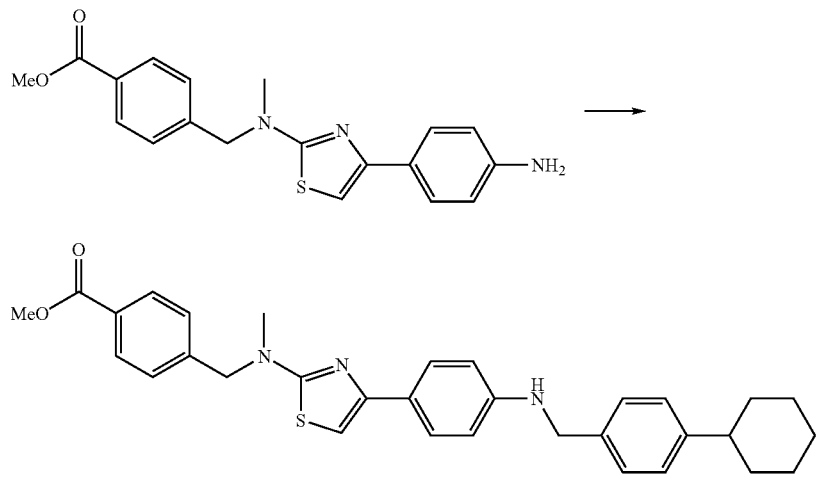

Under an argon stream, tetrahydrofuran (1000 ml, 5.7 v/w) was added to methyl 4-(N-(4-(4-aminophenyl)-2-thiazolyl)-N-methylaminomethyl)benzoate (174.0 g, 0.493 mol) obtained in Example 1(4) and dissolved therein. A solution of 4-cyclohexylbenzaldehyde (120.6 g, 0.641 mol) obtained in Production Example 1(2) in tetrahydrofuran (740 ml, 4.3 v/w) was added. Acetic acid (56.4 ml, 0.986 mol) was added and the mixture was stirred at room temperature for 1 hr. With stirring under ice-cooling, sodium triacetoxyborohydride (104.5 g, 0.493 mol) was added and the mixture was stirred at room temperature for 1.5 hr. After ice-cooling, acetic acid (28.2 ml, 0.493 mol) and sodium triacetoxyborohydride (52.2 g, 0.246 mol) were added and the mixture was stirred at room temperature for 1.5 hr. The reaction mixture was ice-cooled and carefully added to a saturated aqueous sodium hydrogen carbonate solution (2262 ml, 13.0 v/w). After stirring at room temperature for 1 hr, the mixture was extracted with ethyl acetate (522 ml), and the organic layer was washed successively with distilled water (174 ml) and saturated brine (522 ml) and dried over magnesium sulfate (50.0 g). The solvent was evaporated and the obtained orange solid was purified by silica gel column chromatography (developing solvent chloroform:ethyl acetate=99.5:0.5) to give the title compound (80.3 g, yield 31.0%) as a pale-yellow solid.

$^1$H-NMR (300 MHz, DMSO-d$_6$) δ 1.16–1.47(5H, m), 1.65–1.80(5H, m), 2.40–2.55(1H, m), 3.60(3H, s), 3.83(3H, s), 4.22(2H, d, J=5.5 Hz), 4.81(2H, s), 6.32(1H, t, J=5.5 Hz), 6.57(1H, d, J=8.7 Hz), 6.77(1H, s), 7.15(2H, d, J=8.1 Hz), 7.26(2H, d, J=8.1 Hz), 7.45(2H, d, J=8.3 Hz), 7.53(2H, d, J=8.6 Hz), 7.94(2H, d, J=8.3 Hz).

(6) methyl 4-(N-(4-(4-(N-(4-cyclohexylbenzyl)-N-methylamino)phenyl)-2-thiazolyl)-N-methylaminomethyl)benzoate

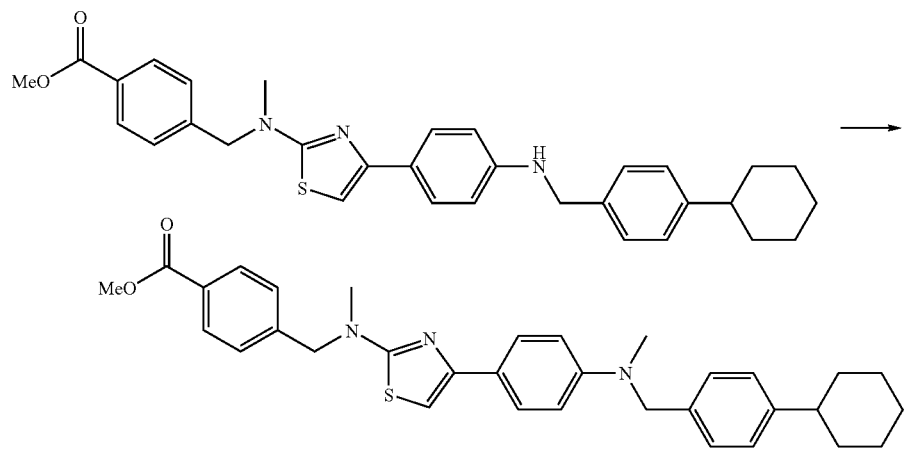

Under an argon stream, N,N-dimethylacetamide (351 ml, 5.0 v/w) was added to methyl 4-(N-(4-(4-(4-cyclohexylbenzylamino)phenyl)-2-thiazolyl)-N-methylaminomethyl)benzoate (70.3 g, 0.134 mol) obtained in Example 1(5) and potassium carbonate (73.9 g, 0.535 mol) was carefully added with stirring. After stirring the mixture at room temperature for 20 min., dimethyl sulfate (50.6 ml, 0.535 mol) was added. After stirring at 50° C. for 1 hr., potassium carbonate (18.4 g, 0.134 mol) and dimethyl sulfate (12.7 ml, 0.134 mol) were added and the mixture was stirred at 60° C. for 2 hr. After cooling to room temperature, n-hexane (422 ml, 6.0 v/w) was added, and the mixture was stirred for 1 hr. After ice-cooling, distilled water (562 ml, 8.0 v/w) was added. After stirring at room temperature for 1 hr., the resulting crystals were collected by filtration and washed with methanol (352 ml, 5.0 v/w) in a slurry form. Tetrahydrofuran (180 ml) was added to the obtained orange solid and insoluble materials were filtered off. The filtrate was concentrated to give the title compound (42.1 g, yield 58.3%) as a pale-yellow solid.

$^1$H-NMR (300 MHz, DMSO-$d_6$) δ 1.16–1.47(5H, m), 1.65–1.80(5H, m), 2.40–2.55(1H, m), 3.01(3H, s), 3.07(3H, s), 3.83(3H, s), 4.54(2H, s), 4.81(2H, s), 6.71(2H, d, J=8.9 Hz), 6.84(1H, s), 7.08–7.16(4H, m), 7.46(2H, d, J=8.3 Hz), 7.62(2H, d, J=8.8 Hz), 7.94(2H, d, J=8.3 Hz).

(7) 4-(N-(4-(4-(N-(4-cyclohexylbenzyl)-N-methylamino)phenyl)-2-thiazolyl)-N-methylaminomethyl)benzoic acid

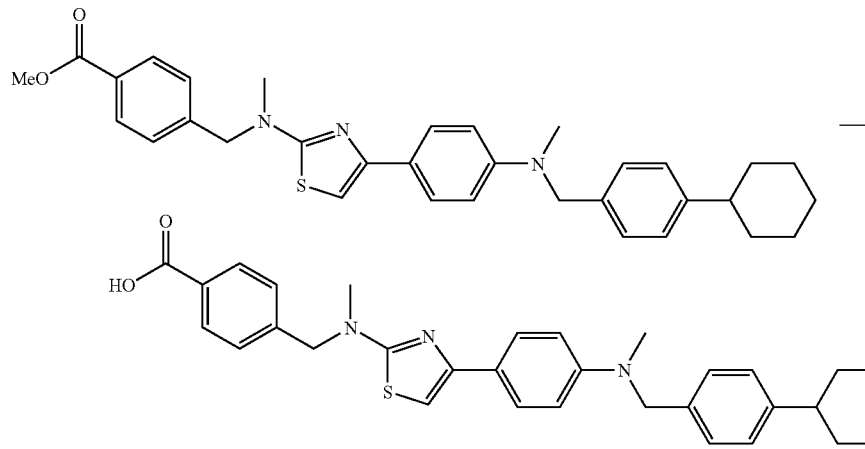

Under an argon stream, tetrahydrofuran (202 ml, 5.0 v/w) and methanol (102 ml, 3.0 v/w) were added to methyl 4-(N-(4-(4-(N-(4-cyclohexylbenzyl)-N-methylamino)phenyl)-2-thiazolyl)-N-methylaminomethyl)benzoate (40.7 g, 75.4 mmol) obtained in Example 1(6). With stirring at 50° C., a 1N-aqueous sodium hydroxide solution (151 ml, 151 mmol) was added. After stirring at 60° C. for 1 hr., distilled water (173 ml, 4.25 v/w) was added. With stirring, 2N-hydrochloric acid (75.4 ml, 151 mmol) was carefully added. After stirring for 1 hr., the resulting crystals were collected by filtration and washed successively with distilled water (407 ml) and ethanol (204 ml), and dried in vacuo to give a yellow solid (39.2 g).

Tetrahydrofuran (172 ml, 4.5 v/w) was added to the obtained yellow solid (38.2 g) and the mixture was stirred at 50° C. for 1 hr. After filtration, the residue was washed with tetrahydrofuran (19 ml, 0.5 v/w). Ethanol (134 ml, 3.5 v/w) and distilled water (134 ml, 3.5 v/w) were successively added to the filtrate with stirring at 50° C. and the mixture was stirred at 50° C. for 1 hr. and at room temperature for 1 hr. The resulting crystals were collected by filtration, washed with ethanol (306 ml) and dried in vacuo to give the title compound (36.5 g, yield 91.9%) as a pale-yellow solid.

$^1$H-NMR (300 MHz, DMSO-$d_6$) δ 1.16–1.47(5H, m), 1.65–1.80(5H, m), 2.40–2.55(1H, m), 3.01(3H, s), 3.07(3H, s), 4.54(2H, s), 4.81(2H, s), 6.71(2H, d, J=9.0 Hz), 6.83(1H, s), 7.08–7.16(4H, m), 7.43(2H, d, J=8.4 Hz), 7.63(2H, d, J=8.8 Hz), 7.92(2H, d, J=8.2 Hz), 12.85(1H, brs).

melting point: 180–181° C.

Example 2 potassium 4-(N-(4-(4-(4-cyclohexylbenzyloxy)phenyl)-2-thiazolyl)-N-methylaminomethyl)benzoate (1) 4-(4-cyclohexylbenzyloxy)acetophenone

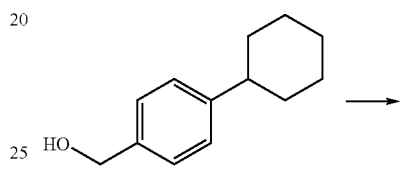

-continued

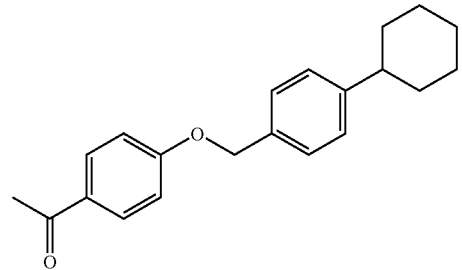

Toluene (225 ml) and 48% hydrobromic acid (150 ml) were added to 4-cyclohexylbenzyl alcohol (74.9 g, 0.394 mol) and the mixture was stirred at 50° C. for 14 hr. After partitioning, the organic layer was washed successively with water (100 ml), saturated aqueous sodium hydrogen carbonate (100 ml), water (100 ml) and saturated brine, and dried over magnesium sulfate. After filtration and solvent evaporation, the residue was dried in vacuo to give a pale-yellow oil. The obtained oil was dissolved in N,N-dimethylformamide (500 ml) and 4-hydroxyacetophenone (50.3 g, 0.369 mol) and potassium carbonate (153 g, 1.11 mol) were added. The mixture was stirred at 45° C. for 70 min. After ice-cooling, water (750 ml) was added dropwise and the mixture was stirred at room temperature for 30 min. The precipitated crystals were collected by filtration, washed with water, washed with n-hexane and dried to give the title compound (93.5 g, yield 86.6%).

$^1$H-NMR (400 MHz, DMSO-d$_6$) δ 1.15–1.52(5H, m), 1.58–1.87(5H, m), 2.47(1H, m), 2.51(3H, s), 5.15(2H, s), 7.10(2H, d, J=9.3 Hz), 7.24(2H, d, J=8.4 Hz), 7.36(2H, d, J=8.4 Hz), 7.92(2H, d, J=9.3 Hz).

(2) 2'-bromo-4-(4-cyclohexylbenzyloxy)acetophenone

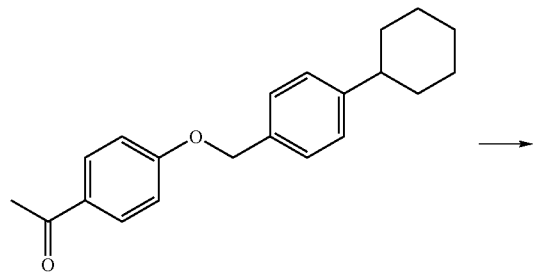

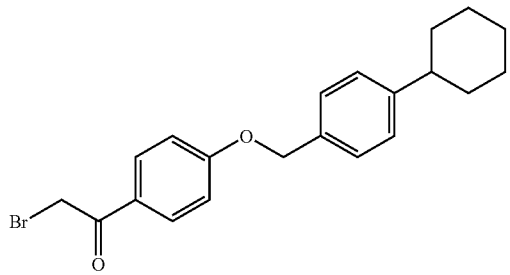

To a suspension of 4-(4-cyclohexylbenzyloxy)acetophenone (60.0 g, 0.195 mol) obtained in Example 2(1) in 1,2-dimethoxyethane (480 ml) was added dropwise a solution of bromine (10.5 ml, 0.205 mol) in 1,2-dimethoxyethane (120 ml) at room temperature. After stirring at room temperature for 90 min., water (600 ml) was added dropwise under ice-cooling, and the mixture was stirred at room temperature for 30 min. The precipitated crystals were collected by filtration, washed with water, washed with n-heptane and dried to give the title compound (68.2 g, yield 90.1%).

$^1$H-NMR (400 MHz, CDCl$_3$) δ 1.18–1.50(5H, m), 1.70–1.95(5H, m), 2.51(1H, m), 4.38(2H, s), 5.10(2H, s), 7.03(2H, d, J=8.9 Hz), 7.24(2H, d, J=8.4 Hz), 7.34(2H, d, J=8.4 Hz), 7.96(2H, d, J=8.9 Hz).

(3) methyl 4-(4-(4-(4-cyclohexylbenzyloxy)phenyl)-2-thiazolylaminomethyl)benzoate

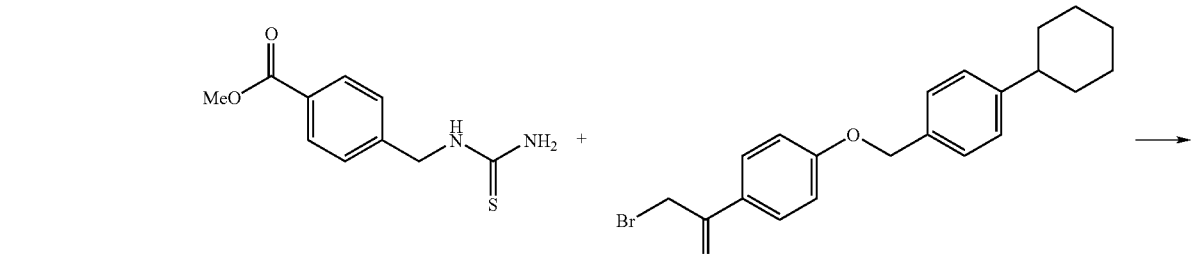

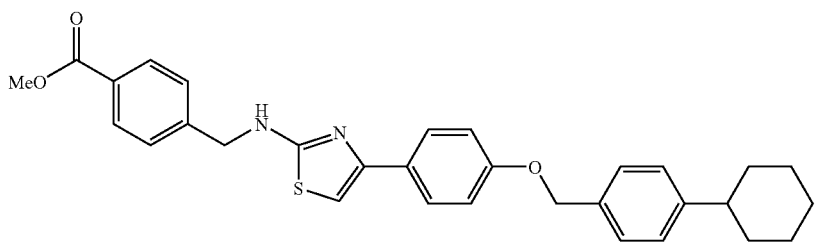

Acetonitrile (630 ml) was added to 1-(4-methoxycarbonylbenzyl)-2-thiourea (33.0 g, 0.147 mol) obtained in Example 1(1), 2'-bromo-4-(4-cyclohexylbenzyloxy)acetophenone (62.7 g, 0.162 mol) obtained in Example 2(2) and sodium bicarbonate (13.6 g, 0.162 mol), and the mixture was heated under reflux for 4 hr. After cooling to room temperature, water (630 ml) was added and the mixture was stirred at the same temperature for 1 hr. The precipitated crystals were collected by filtration, washed successively with 50% acetonitrile (130 ml), water (2 L) and diisopropyl ether (500 ml) and dried to give the title compound (76.4 g, quant.).

$^1$H-NMR (400 MHz, DMSO-$d_6$) δ 1.16–1.47(5H, m), 1.65–1.80(5H, m), 2.50(1H, m), 3.84(3H, s), 4.61(2H, brs), 5.06(2H, s), 6.91(1H, s), 7.00(2H, d, J=8.9 Hz), 7.23(2H, d, J=8.1 Hz), 7.35(2H, d, J=8.1 Hz), 7.53(2H, d, J=8.1 Hz), 7.70(2H, d, J=8.9 Hz), 7.94(2H, d, J=8.1 Hz), 8.28–8.52(1H, brs).

(4) methyl 4-(N-(4-(4-(4-cyclohexylbenzyloxy)phenyl)-2-thiazolyl)-N-methylaminomethyl)benzoate sulfate (15.0 ml, 0.159 mol) were successively added dropwise to a suspension of sodium hydride (content 60%, 6.09 g, 0.152 mol) in N,N-dimethylformamide (130 ml) at 10° C. or below and the mixture was stirred at room temperature for 1 hr. Diisopropyl ether (195 ml) and water (130 ml) were successively added dropwise at 10° C. or below, and the mixture was stirred at room temperature for 30 min. The precipitated crystals were collected by filtration, washed successively with diisopropyl ether (195 ml) and water (130 ml) and dried to give the title compound (56.0 g, 83.7%).

$^1$H-NMR (400 MHz, DMSO-$d_6$) δ 1.16–1.47(5H, m), 1.65–1.86(5H, m), 2.50(1H, m), 3.09(3H, s), 3.84(3H, s), 4.83(2H, s), 5.06(2H, s), 7.00(2H, d, J=8.9 Hz), 7.01(1H, s),

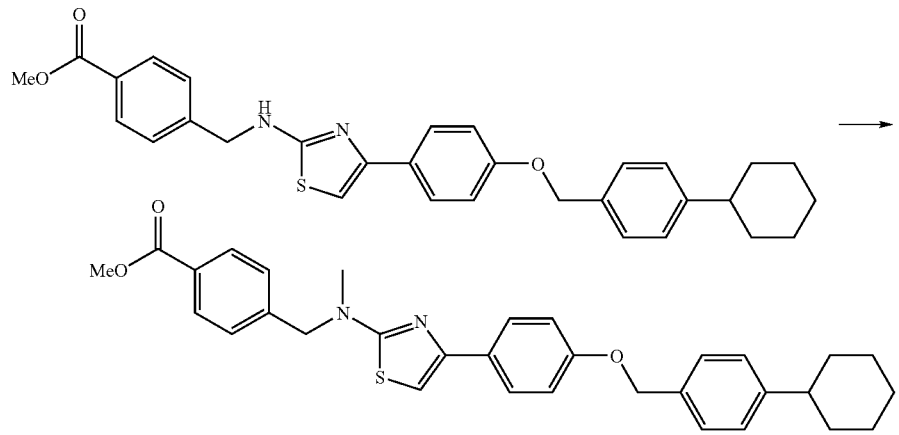

Under an argon atmosphere, a suspension of methyl 4-(4-(4-(4-cyclohexylbenzyloxy)phenyl)-2-thiazolylaminomethyl)benzoate (65.0 g, 0.127 mol) obtained in Example 2(3) in N,N-dimethylformamide (130 ml) and dimethyl 7.23(2H, d, J=8.1 Hz), 7.35(2H, d, J=8.1 Hz), 7.46(2H, d, J=8.1 Hz), 7.76(2H, d, J=8.9 Hz), 7.94(2H, d, J=8.1 Hz).

(5) 4-(N-(4-(4-(4-cyclohexylbenzyloxy)phenyl)-2-thiazolyl)-N-methylaminomethyl)benzoic acid

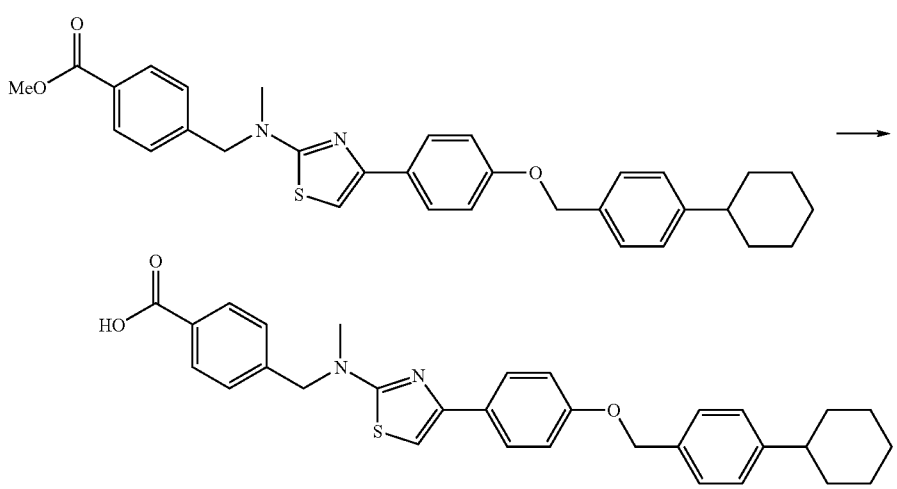

Tetrahydrofuran (250 ml), methanol (250 ml) and a 2N-aqueous sodium hydroxide solution (95.0 ml, 190 mmol) were added to methyl 4-(N-(4-(4-(4-cyclohexylbenzyloxy)phenyl)-2-thiazolyl)-N-methylaminomethyl)benzoate (50.0 g, 94.9 mmol) obtained in Example 2(4), and the mixture was heated under reflux for 40 min under an argon atmosphere. Water (310 ml) was added to the reaction mixture and the mixture was cooled to room temperature. 2N-Hydrochloric acid (95.0 ml, 190 mmol) was added dropwise and the mixture was stirred for 90 min. The resulting crystals were collected by filtration, washed with water (700 mL) and dried to give the title compound (48.5 g, yield 99.7%).

$^{1}$H-NMR (400 MHz, DMSO-d$_{6}$) δ 1.15–1.47(5H, m), 1.64–1.85(5H, m), 2.47(1H, m), 3.09(3H, s), 4.82(2H, s), 5.06(2H, s), 7.00(2H, d, J=9.2 Hz), 7.02(1H, s), 7.23(2H, d, J=8.4 Hz), 7.35(2H, d, J=8.4 Hz), 7.42(2H, d, J=8.1 Hz), 7.77(2H, d, J=9.2 Hz), 7.92(2H, d, J=8.1 Hz).

(6) potassium 4-(N-(4-(4-(4-cyclohexylbenzyloxy)phenyl)-2-thiazolyl)-N-methylaminomethyl)benzoate

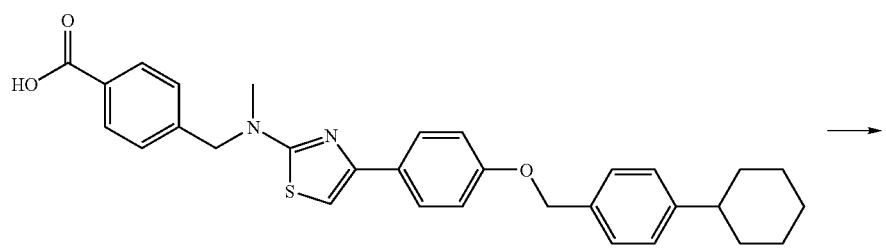

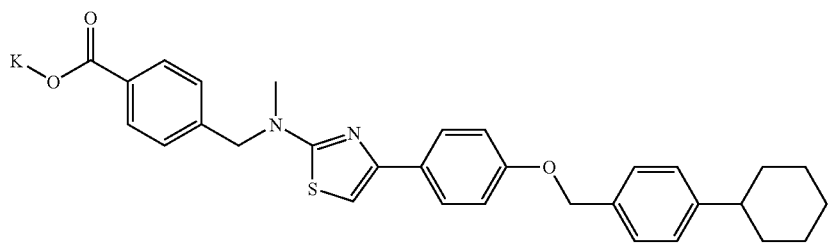

Under an argon atmosphere, to a suspension of 4-(N-(4-(4-(4-cyclohexylbenzyloxy)phenyl)-2-thiazolyl)-N-methylaminomethyl)benzoic acid (30.0 g, 58.5 mmol) obtained in Example 2(5) was added 1N aqueous potassium hydroxide solution (56.0 ml) at 50° C. and the mixture was heated under reflux for 40 min. After stirring at room temperature for 45 min., the crystals were collected by filtration, washed with a tetrahydrofuran-ethanol mixed solvent (3:1, 150 ml) and ethanol (210 ml), and dried to give the title compound (28.0 g, yield 90.9%).

$^{1}$H-NMR (400 MHz, DMSO-d$_{6}$) δ 1.17–1.47(5H, m), 1.65–1.84(5H, m), 2.50(1H, m), 3.04(3H, s), 4.71(2H, s), 5.07(2H, s), 6.99(1H, s), 7.00(2H, d, J=8.9 Hz), 7.19(2H, d, J=8.1 Hz), 7.23(2H, d, J=8.1 Hz), 7.36(2H, d, J=8.1 Hz), 7.77(2H, d, J=8.9 Hz), 7.79(2H, d, J=8.1 Hz).

melting point: 288–291° C. (dec.)

Example 3

4-(N-(4-(4-(4-cyclohexylbenzylamino)phenyl)-2-thiazolyl)-N-methylamino)benzoic acid (1) ethyl 4-((4-(4-nitrophenyl)-2-thiazolyl)amino)benzoate hydrobromide

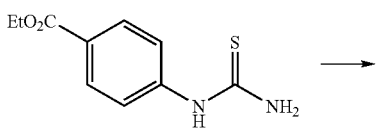

-continued

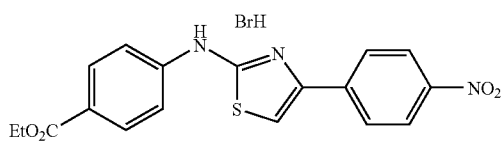

A solution of 2'-bromo-4-nitroacetophenone (87.1 g, 0.357 mol) and 1-(4-ethoxycarbonylphenyl)-2-thiourea (80.0 g, 0.357 mol) in acetonitrile (1.6 L) was heated under reflux for 1 hr under an argon atmosphere. After cooling to room temperature, the resulting crystals were collected by filtration and dried to give the title compound (153 g, yield 94.9%).

¹H-NMR (400 MHz, DMSO-d₆) δ 1.33(3H, t, J=7.1 Hz), 4.29(2H, q, J=7.1 Hz), 7.84(1H, s), 7.87(2H, d, J=9.1 Hz), 7.97(2H, d, J=8.6 Hz), 8.22(2H, d, J=8.6 Hz), 8.27(2H, d, J=9.2 Hz), 10.82(1H, s).

(2) ethyl 4-(N-methyl-N-(4-(4-nitrophenyl)-2-thiazolyl)amino)benzoate

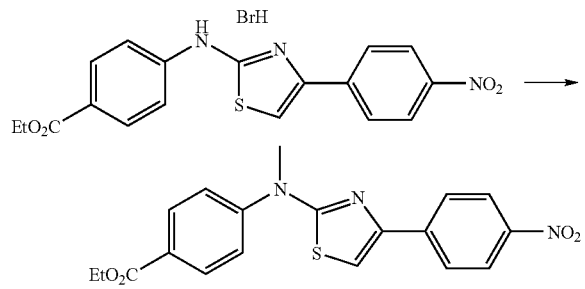

Under a nitrogen stream, N,N-dimethylformamide (1.05 L, 7.0 v/w) was added to ethyl 4-((4-(4-nitrophenyl)-2-thiazolyl)amino)benzoate hydrobromide (150 g, 0.333 mol) obtained in Example 3(1). With stirring under ice-cooling, potassium carbonate (138 g, 0.999 mol) was added carefully. After stirring at room temperature for 20 min., dimethyl sulfate (63.2 ml, 0.666 mol) was added. After stirring at 60° C. for 2 hr., distilled water (1.05 L, 7.0 v/w) was added with stirring under ice-cooling. After stirring under ice-cooling for 1 hr., the resulting crystal were collected by filtration, washed with distilled water (450 mL) and dried in vacuo to give the title compound (127 g, yield 99.3%) as an orange crystal.

¹H-NMR (400 MHz, DMSO-d₆) δ 1.34(3H, t, J=7.1 Hz), 3.62(3H, s), 4.33(2H, q, J=7.1 Hz), 7.74(2H, d, J=8.8 Hz), 7.78(1H, s), 8.03(2H, d, J=8.8 Hz), 8.14(2H, d, J=9.0 Hz), 8.28(2H, d, J=9.0 Hz).

(3) ethyl 4-(N-(4-(4-aminophenyl)-2-thiazolyl)-N-methylamino)benzoate

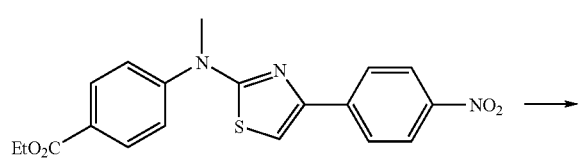

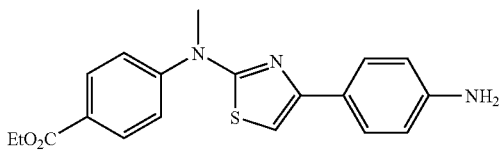

Under a nitrogen stream, N,N-dimethylformamide (1.20 L, 10.0 v/w) was added to ethyl 4-(N-methyl-N-(4-(4-nitrophenyl)-2-thiazolyl)amino)benzoate (123 g, 0.321 mol) obtained in Example 3(2). With stirring at room temperature, sodium hydrosulfite (80% purity, 210 g, 0.963 mol) was added. After stirring at room temperature for 10 min., distilled water (123 ml, 1.0 v/w) was added carefully. After stirring at 100° C. for 1.5 hr., triethylamine (223 ml, 1.61 mol) was added at 80° C., and the mixture was cooled to room temperature with water. After stirring at room temperature for 1 hr., distilled water (1.1 L, 9.0 v/w) was added. After stirring at room temperature for 30 min., the mixture was extracted twice with ethyl acetate (1.20 L) and the organic layer was washed successively with distilled water (400 ml) and saturated brine (400 ml), and dried over magnesium sulfate (60 g). The magnesium sulfate was filtered off, the solvent was evaporated, the residue was boiled with toluene and dried in vacuo to give the title compound (67.0 g, yield 63.0%) as a yellow to orange solid.

¹H-NMR (400 MHz, DMSO-d₆) δ 1.33(3H, t, J=7.0 Hz), 3.57(3H, s), 4.32(2H, q, J=7.0 Hz), 5.27(2H, brs), 6.59(2H, d, J=8.6 Hz), 7.02(1H, s), 7.56(2H, d, J=8.6 Hz), 7.71(2H, d, J=9.0 Hz), 7.99(2H, d, J=9.0 Hz).

(4) ethyl 4-(N-(4-(4-(4-cyclohexylbenzylamino)phenyl)-2-thiazolyl)-N-methylamino)benzoate

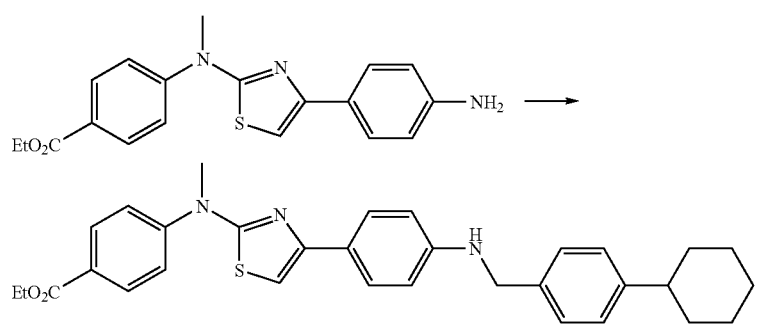

Under a nitrogen stream, tetrahydrofuran (306 ml, 6.0 v/w) was added to ethyl 4-(N-(4-(4-aminophenyl)-2-thiazolyl)-N-methylamino)benzoate (51.0 g, 0.144 mol) obtained in Example 3(3). With stirring at room temperature, a solution of 4-cyclohexylbenzaldehyde (30.0 g, 0.158 mol) obtained in Production Example 1(2) in tetrahydrofuran (153 ml, 3.0 v/w) was added. The mixture was washed with tetrahydrofuran (51 ml, 1.0 v/w) and stirred at room temperature for 30 min. With stirring under ice-cooling, sodium triacetoxyborohydride (46.0 g, 0.216 mol) and acetic acid (12.4 ml, 0.216 mol) were added, and the mixture was stirred at room temperature for 1.5 hr. With stirring under ice-cooling, saturated aqueous sodium hydrogen carbonate (510 ml, 10.0 v/w) was added carefully. After stirring at room temperature for 1 hr., the mixture was extracted with ethyl acetate (408 ml) and the organic layer was washed successively with distilled water (255 ml) and saturated brine (255 ml), and dried over magnesium sulfate (50 g). After filtration and solvent evaporation, isopropyl alcohol (510 ml, 10.0 v/w) was added to the obtained orange solid, and the mixture was stirred at 60° C. for 1 hr. After stirring under ice-cooling for 1 hr., the resulting crystal were collected by filtration, and washed with isopropyl alcohol (102 ml) and tert-butylmethyl ether (102 ml) and dried in vacuo to give the title compound (58.0 g, yield 77.0%) as a pale-yellow solid.

$^1$H-NMR (400 MHz, DMSO-$d_6$) δ 1.23–1.40(8H, m,), 1.67–1.78(5H, m), 2.46(1H, s), 3.56(3H, s), 4.24(2H, d, J=6.1 Hz), 4.31(2H, q, J=7.1 Hz), 6.35(1H, t, J=6.1 Hz), 6.60(2H, d, J=8.6 Hz), 7.01(1H, s), 7.16(2H, d, J=7.6 Hz), 7.27(6H, d, J=7.6 Hz), 7.57(2H, d, J=8.6 Hz), 7.70(2H, d, J=8.9 Hz), 7.98(2H, d, J=8.9 Hz).

(5) 4-(N-(4-(4-(4-cyclohexylbenzylamino)phenyl)-2-thiaz-olyl)-N-methylamino)benzoic acid

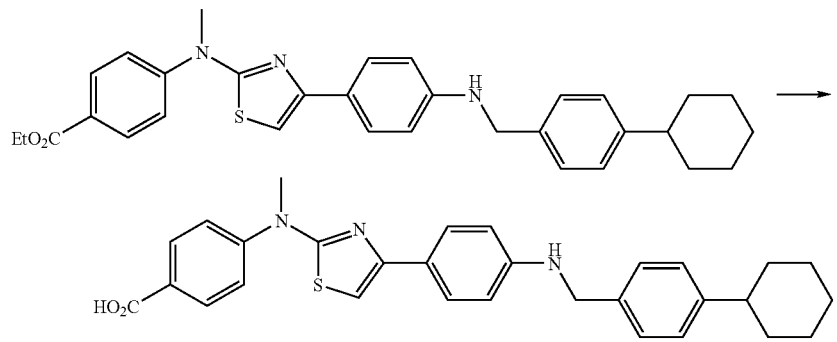

Under a nitrogen stream, tetrahydrofuran (312 ml, 6.0 v/w) and methanol (104 ml, 2.0 v/w) were added to ethyl 4-(N-(4-(4-(4-cyclohexylbenzylamino)phenyl)-2-thiazolyl)-N-methylamino)benzoate (52.0 g, 98.9 mmol) obtained in Example 3(4). With stirring under ice-cooling, 2N-aqueous sodium hydroxide solution (98.9 ml, 197.8 mmol) was added. After stirring at 60° C. for 2 hr., distilled water (104 ml, 2.0 v/w) was added. With stirring under ice-cooling, 2N-hydrochloric acid (98.9 ml, 197.8 mmol) was added carefully. After stirring under ice-cooling for 1 hr., the resulting crystal were collected by filtration, washed with distilled water (156 ml) and dried in vacuo to give a yellow solid (51.9 g). Tetrahydrofuran (750 ml, 15.0 v/w) was added to the obtained yellow solid (50.0 g) and the mixture was stirred at 60° C. for 1 hr. After allowing to cool to room temperature, the precipitate was collected by filtration and washed with tetrahydrofuran (100 ml, 2.0 v/w). With stirring at room temperature, ethanol (150 ml) and distilled water (150 ml) were successively added to the filtrate. After stirring under ice-cooling for 1 hr., the resulting crystals were collected by filtration, washed successively with distilled water (200 ml) and 50% aqueous ethanol (200 ml) and dried in vacuo to give a crude title compound (33.6 g) as a yellow solid. Ethanol (350 ml, 7.0 v/w) was added and the mixture was stirred at room temperature for 2 hr. The resulting crystals were collected by filtration, washed with ethanol (200 ml) and dried in vacuo to give the title compound (32.1 g, yield 64.2%) as a pale-yellow solid.

$^1$H-NMR (400 MHz, DMSO-$d_6$) δ 1.20–1.40(5H, m), 1.67–1.78(5H, m), 2.43(1H, m), 3.56(1H, s), 4.23(3H, d, J=5.1 Hz), 6.34(1H, brt, J=5.1 Hz), 6.60(2H, d, J=8.6 Hz), 6.98(1H, s), 7.16(2H, d, J=8.1 Hz), 7.27(2H, d, J=8.1 Hz), 7.57(2H, d, J=8.6 Hz), 7.67(2H, d, J=8.9 Hz), 7.97(2H, d, J=8.9 Hz).

melting point: 252–253° C. (dec.)

The following compounds were produced according to a method similar to the methods of Examples 1–3, and using a conventional method where necessary.

4-(4-(4-benzoylaminophenyl)-2-thiazolylamino)benzoic acid (Example 4), 4-(4-(4-(4-tert-butylbenzoylamino)phenyl)-2-thiazolylamino)benzoic acid (Example 5), 4-(4-(4-(4-cyclohexylbenzoylamino)phenyl)-2-thiazolylamino)benzoic acid (Example 6), 4-(N-(4-(4-benzoylaminophenyl)-2-thiazolyl)-N-ethylamino)benzoic acid (Example 7), 4-(N-(4-(4-(4-cyclohexylbenzoylamino)phenyl)-2-thiazolyl)-N-ethylamino)benzoic acid (Example 8), 4-(N-(4-(4-benzoylaminophenyl)-2-thiazolyl)-N-isopropylamino)benzoic acid (Example 9), 4-(N-(4-(4-(4-cyclohexylbenzoylamino)phenyl)-2-thiazolyl)-N-isopropylamino)benzoic acid (Example 10), 4-(N-(4-(4-(cyclohexanecarbonylamino)phenyl)-2-thiazolyl)-N-ethylamino)benzoic acid (Example 11), 4-(N-(4-(4-(cyclohexanecarbonylamino)phenyl)-2-thiazolyl)-N-isopropylamino)benzoic acid (Example 12), 4-(N-(4-(4-(cyclohexanecarbonylamino)phenyl)-2-thiazolyl)-N-isobutylamino)benzoic acid (Example 13), 4-(N-carboxymethyl-N-(4-(4-(cyclohexanecarbonylamino)phenyl)-2-thiazolyl)amino)benzoic acid (Example 14), 4-(N-(4-(4-benzoylaminophenyl)-2-thiazolyl)-N-isobutylamino)benzoic acid (Example 15), 4-(N-(4-(4-benzoylaminophenyl)-2-thiazolyl)-N-carboxymethylamino)benzoic acid (Example 16), 4-(N-(4-(4-(4-cyclohexylbenzoylamino)phenyl)-2-thiazolyl)-N-isobutylamino)benzoic acid (Example 17), 4-(N-carboxymethyl-N-(4-(4-(4-cyclohexylbenzoylamino)phenyl)-2-thiazolyl)amino)benzoic acid (Example 18), 4-(N-(4-(4-(4-cyclohexylbenzoylamino)phenyl)-2-thiazolyl)-N-methylamino)benzoic acid (Example 19), 4-(N-(4-(4-(4-tert-butylbenzoylamino)phenyl)-2-thiazolyl)-N-methylamino)benzoic acid (Example 20), 4-(4-(4-(4-cyclohexylbenzyloxy)phenyl)-2-thiazolylamino)benzoic acid (Example 21), 4-(N-(4-(4-(4-cyclohexylbenzyloxy)phenyl)-2-thiazolyl)-N-methylamino)benzoic acid (Example 22), 4-(N-(4-(4-(4-cyclohexylbenzyloxy)phenyl)-2-thiazolyl)-N-ethylamino)benzoic acid (Example 23),
4-(N-(4-(4-(4-cyclohexylbenzyloxy)phenyl)-2-thiazolyl)-N-isopropylamino)benzoic acid (Example 24),
4-(N-(4-(4-(4-cyclohexylbenzyloxy)phenyl)-2-thiazolyl)-N-cyclohexylmethylamino)benzoic acid (Example 25),
4-(N-(3-carboxypropyl)-N-(4-(4-(4-cyclohexylbenzyloxy)phenyl)-2-thiazolyl)amino)benzoic acid (Example 26),
3-(4-(4-(4-cyclohexylbenzoylamino)phenyl)-2-thiazolylamino)benzoic acid (Example 27),
3-(N-(4-(4-(4-cyclohexylbenzoylamino)phenyl)-2-thiazolyl)-N-isopropylamino)benzoic acid (Example 28),
4-(N-isopropyl-N-(4-(4-(4-morpholinobenzoylamino)phenyl)-2-thiazolyl)amino)benzoic acid hydrochloride (Example 29),
3-(N-isopropyl-N-(4-(4-(4-piperidinobenzoylamino)phenyl)-2-thiazolyl)amino)benzoic acid hydrochloride (Example 30),
3-(N-isopropyl-N-(4-(4-(4-morpholinobenzoylamino)phenyl)-2-thiazolyl)amino)benzoic acid hydrochloride (Example 31),
4-(N-isopropyl-N-(4-(4-(4-piperidinobenzoylamino)phenyl)-2-thiazolyl)amino)benzoic acid hydrochloride (Example 32),
4-(N-isopropyl-N-(4-(4-(4-(4-methylpiperidino)benzoylamino)phenyl)-2-thiazolyl)amino)benzoic acid hydrochloride (Example 33),
sodium 4-(N-(4-(4-(4-cyclohexylbenzyloxy)phenyl)-2-thiazolyl)-N-isopropylamino)benzoate (Example 34),
4-(N-(4-(4-(3,5-dimethylpiperidino)benzoylamino)phenyl)-2-thiazolyl)-N-isopropylamino)benzoic acid hydrochloride (Example 35),
cis-4-(N-(4-(4-(4-(2,6-dimethylmorpholino)benzoylamino)phenyl)-2-thiazolyl)-N-isopropylamino)benzoic acid hydrochloride (Example 36),
sodium 4-(N-isopropyl-N-(4-(4-(4-(4-methyl-1-piperazinyl)benzoylamino)phenyl)-2-thiazolyl)amino)benzoate (Example 37),
2-chloro-4-(N-(4-(4-(4-cyclohexylbenzoylamino)phenyl)-2-thiazolyl)-N-isopropylamino)benzoic acid (Example 38),
2-chloro-4-(N-isopropyl-N-(4-(4-(4-piperidinobenzoylamino)phenyl)-2-thiazolyl)amino)benzoic acid hydrochloride (Example 39),
2-chloro-4-(N-isopropyl-N-(4-(4-(4-morpholinobenzoylamino)phenyl)-2-thiazolyl)amino)benzoic acid hydrochloride (Example 40),
2-chloro-4-(N-isopropyl-N-(4-(4-(4-(4-methyl-1-piperazinyl)benzoylamino)phenyl)-2-thiazolyl)amino)benzoic acid (Example 41),
4-(1-(4-(4-(4-cyclohexylbenzyloxy)phenyl)-2-thiazolyl)-1-methylethyl)benzoic acid (Example 42),
4-(1-(4-(4-(4-cyclohexylbenzoylamino)phenyl)-2-thiazolyl)-1-methylethyl)benzoic acid (Example 43),
4-(1-methyl-1-(4-(4-(4-morpholinobenzoylamino)phenyl)-2-thiazolyl)ethyl)benzoic acid (Example 44),
4-(1-methyl-1-(4-(4-(4-piperidinobenzoylamino)phenyl)-2-thiazolyl)ethyl)benzoic acid (Example 45),
4-(N-(4-(4-(4-cyclohexylbutyrylamino)phenyl)-2-thiazolyl)-N-isopropylamino)benzoic acid (Example 46),
4-(4-(4-(4-tert-butylbenzyloxy)phenyl)-2-thiazolylmethyl)benzoic acid (Example 47),
4-(4-(4-(4-cyclohexylbenzyloxy)phenyl)-2-thiazolylmethyl)benzoic acid (Example 48),
4-(4-(4-(4-carboxybenzyloxy)phenyl)-2-thiazolylmethyl)benzoic acid (Example 49), (4-(N-(4-(4-(cyclohexanecarbonylamino)phenyl)-2-thiazolyl)-N-isopropylamino)phenoxy)acetic acid (Example 50),
(4-(N-(4-(4-(4-cyclohexylbenzoylamino)phenyl)-2-thiazolyl)-N-isopropylamino)phenoxy)acetic acid (Example 51),
4-(N-(4-(4-(4-cyclohexylbenzoylamino)phenyl)-2-thiazolyl)-N-isopropylamino)-2,3,5,6-tetrafluorobenzoic acid (Example 52),
(4-(N-isopropyl-N-(4-(4-(4-piperidinobenzoylamino)phenyl)-2-thiazolyl)amino)phenoxy)acetic acid (Example 53),
(4-(N-isopropyl-N-(4-(4-(4-morpholinobenzoylamino)phenyl)-2-thiazolyl)amino)phenoxy)acetic acid (Example 54),
(4-(N-(4-(4-(3,5-bis(trifluoromethyl)benzoylamino)phenyl)-2-thiazolyl)-N-isopropylamino)phenoxy)acetic acid (Example 55),
(4-(N-(4-(4-(3,5-dichlorobenzoylamino)phenyl)-2-thiazolyl)-N-isopropylamino)phenoxy)acetic acid (Example 56),
(4-(N-isopropyl-N-(4-(4-(2-piperidino-5-pyridinecarbonylamino)phenyl)-2-thiazolyl)amino)phenoxy)acetic acid (Example 57),
4-(N-(4-(4-(4-cyclohexylbenzoylamino)phenyl)-2-thiazolyl)-N-cyclohexylmethylamino)benzoic acid (Example 58),
4-(N-cyclohexylmethyl-N-(4-(4-(4-trifluoromethylbenzoylamino)phenyl)-2-thiazolyl)amino)benzoic acid (Example 59),
4-(N-(4-(4-(N-(4-cyclohexylbenzoyl)-N-methylamino)phenyl)-2-thiazolyl)-N-isopropylamino)benzoic acid (Example 60),
4-((N-(4-(4-(4-cyclohexylbenzoylamino)phenyl)-2-thiazolyl)-N-isopropylamino)methyl)benzoic acid (Example 61),
4-((N-isopropyl-N-(4-(4-(4-piperidinobenzoylamino)phenyl)-2-thiazolyl)amino)methyl)benzoic acid (Example 62),
4-((N-isopropyl-N-(4-(4-(4-morpholinobenzoylamino)phenyl)-2-thiazolyl)amino)methyl)benzoic acid (Example 63),
4-((N-(4-(4-(4-biphenylcarbonylamino)phenyl)-2-thiazolyl)-N-isopropylamino)methyl)benzoic acid (Example 64),
4-((N-(4-(4-(4-cyclohexylbenzyloxy)phenyl)-2-thiazolyl)-N-isopropylamino)methyl)benzoic acid (Example 65),
4-(2-(4-(4-(4-cyclohexylbenzoylamino)phenyl)-2-thiazolyl)ethyl)benzoic acid (Example 66),
4-(N-(4-(4-(4-cyclohexylbenzylamino)phenyl)-2-thiazolyl)-N-isopropylamino)benzoic acid (Example 67),
4-(4-(4-(4-cyclohexylbenzoylamino)phenyl)-2-thiazolylmethyl)benzoic acid (Example 68),
4-(4-(4-(4-isopropoxybenzoylamino)phenyl)-2-thiazolylmethyl)benzoic acid (Example 69),
4-(4-(4-(4-(1-pyrrolyl)benzoylamino)phenyl)-2-thiazolylmethyl)benzoic acid (Example 70),
4-(4-(4-(4-cyclohexylbenzyloxy)phenyl)-2-thiazolecarbonyl)benzoic acid (Example 71),
4-(4-(4-(4-cyclohexylbenzyloxy)phenyl)-2-thiazolylamino)-3-(2-cyclohexylethoxy)benzoic acid (Example 72),
3-benzyloxy-4-(4-(4-(4-cyclohexylbenzyloxy)phenyl)-2-thiazolylamino)benzoic acid (Example 73),
3-(4-carboxybenzyloxy)-4-(4-(4-(4-cyclohexylbenzyloxy)phenyl)-2-thiazolylamino)benzoic acid (Example 74), 4-cyclohexyl-N-(4-(2-(N-isopropyl-N-(4-(1H-tetrazol-5-yl)phenyl)amino)-4-thiazolyl)phenyl)benzamide (Example 75), 3-(2-(4-(4-cyclohexylbenzoylamino)phenyl)-2-thiazolyl)ethyl)benzoic acid (Example 76), 4-((N-(4-(4-(3,4-dichlorobenzyloxy)phenyl)-2-thiazolyl)-N-isopropylamino)methyl)benzoic acid (Example 77), N-(4-(4-(4-cyclohexylbenzyloxy)phenyl)-2-thiazolyl)-N-isopropyl-(4-(1H-tetrazol-5-yl)phenyl)amine (Example 78), N-(4-(4-(4-cyclohexylbenzyloxy)phenyl)-2-thiazolyl)-N-isopropyl-(4-(1H-tetrazol-5-yl)benzyl)amine (Example 79), N-(4-(4-(4-cyclohexylbenzyloxy)phenyl)-2-thiazolyl)-N-isopropyl-(3-(1H-tetrazol-5-yl)benzyl)amine (Example 80), 4-((4-(4-(4-cyclohexylbenzyloxy)phenyl)-2-thiazolylamino)methyl)benzoic acid (Example 81), 4-((N-(4-(4-(4-cyclohexylbenzyloxy)phenyl)-2-thiazolyl)-N-methylamino)methyl)benzoic acid (Example 82), 4-((N-(4-(4-(4-(4-fluorophenyl)-2-methyl-5-thiazolylmethoxy)phenyl)-2-thiazolyl)-N-isopropylamino)methyl)benzoic acid (Example 83), 4-((N-(4-(4-(4'-chloro-4-methoxybiphenyl-2-ylmethoxy)phenyl)-2-thiazolyl)-N-isopropylamino)methyl)benzoic acid (Example 84), 4-((N-isopropyl-N-(4-(4-(4-methyl-2-(4-trifluoromethylphenyl)-5-thiazolylmethoxy)phenyl)-2-thiazolyl)amino)methyl)benzoic acid (Example 85), N-(4-(4-(4-cyclohexylbenzyloxy)phenyl)-2-thiazolyl)-N-isopropyl-(2-(1H-tetrazol-5-yl)benzyl)amine (Example 86), 3-((N-(4-(4-(4-cyclohexylbenzyloxy)phenyl)-2-thiazolyl)-N-isopropylamino)methyl)benzoic acid (Example 87), 2-((N-(4-(4-(4-cyclohexylbenzyloxy)phenyl)-2-thiazolyl)-N-isopropylamino)methyl)benzoic acid (Example 88), 4-(N-(4-(4-(3,4-dichlorobenzyloxy)phenyl)-2-thiazolyl)-N-methylamino)benzoic acid (Example 89), 4-(1-(4-(4-(3,4-dichlorobenzyloxy)phenyl)-2-thiazolyl)-1-methylethyl)benzoic acid (Example 90), 4-(1-(4-(4-(4-cyclohexylbenzyloxy)phenyl)-2-thiazolyl)cyclopentyl)benzoic acid (Example 91), 4-(1-(4-(4-(4-biphenylylmethoxy)phenyl)-2-thiazolyl)-1-methylethyl)benzoic acid (Example 92), 4-(1-(4-(4-(3,4-dichlorobenzyloxy)phenyl)-2-thiazolyl)cyclohexyl)benzoic acid (Example 93), 4-(4-(4-(3,4-dichlorobenzyloxy)phenyl)-2-thiazolylamino)benzoic acid (Example 94), 4-(4-(4-(4-biphenylylmethoxy)phenyl)-2-thiazolylamino)benzoic acid (Example 95), 4-(N-(4-(4-(3,4-dichlorobenzyloxy)phenyl)-2-thiazolyl)-N-isopropylamino)benzoic acid (Example 96), 4-(N-(4-(4-(3,4-dichlorobenzyloxy)phenyl)-2-thiazolyl)-N-(2-dimethylaminoethyl)amino)benzoic acid (Example 97), 4-(N-(4-(4-(3,4-dichlorobenzyloxy)phenyl)-2-thiazolyl)-N-(2-piperidinoethyl)amino)benzoic acid (Example 98), 4-(N-(4-(4-(3,4-dichlorobenzyloxy)phenyl)-2-thiazolyl)-N-(2-methoxyethyl)amino)benzoic acid (Example 99), 4-(1-(4-(4-(4-cyclohexylbenzyloxy)phenyl)-2-thiazolyl)cyclohexyl)benzoic acid (Example 100), 4-(4-(4-(4-cyclohexylbenzyloxy)phenyl)-2-thiazolyl)tetrahydropyran-4-yl)benzoic acid (Example 101), sodium 4-(N-(4-(4-(N-(4-cyclohexylbenzyl)-N-methylamino)phenyl)-2-thiazolyl)-N-methylaminomethyl)benzoate (Example 102), 4-((N-isopropyl-N-(4-(4-(4-trifluoromethylbenzyloxy)phenyl)-2-thiazolyl)amino)methyl)benzoic acid (Example 103), 4-((N-(4-(4-(4-tert-butylbenzenesulfonylamino)phenyl)-2-thiazolyl)-N-isopropylamino)methyl)benzoic acid (Example 104), 4-((N-(4-(4-(3,4-dichlorobenzenesulfonylamino)phenyl)-2-thiazolyl)-N-isopropylamino)methyl)benzoic acid (Example 105), 4-((N-isopropyl-N-(4-(4-(4-trifluoromethylbenzenesulfonylamino)phenyl)-2-thiazolyl)amino)methyl)benzoic acid (Example 106), 4-((N-(4-(4-(4-cyclohexylbenzenesulfonylamino)phenyl)-2-thiazolyl)-N-isopropylamino)methyl)benzoic acid (Example 107), 4-((N-(4-(4-(4-cyclohexylbenzylsulfanyl)phenyl)-2-thiazolyl)-N-isopropylamino)methyl)benzoic acid (Example 108), 4-((N-(4-(4-dibenzylaminophenyl)-2-thiazolyl)-N-isopropylamino)methyl)benzoic acid (Example 109), 4-((N-(4-(4-(N-(4-cyclohexylbenzenesulfonyl)-N-methylamino)phenyl)-2-thiazolyl)-N-isopropylamino)methyl)benzoic acid (Example 110), 4-((N-(4-(4-(4-cyclohexylbenzyloxy)phenyl)-2-thiazolyl)-N-propylamino)methyl)benzoic acid (Example 111), 4-((N-(4-(4-(4-cyclohexylphenylmethanesulfonyl)phenyl)-2-thiazolyl)-N-isopropylamino)methyl)benzoic acid (Example 112), 4-((N-benzyl-N-(4-(4-(4-cyclohexylbenzyloxy)phenyl)-2-thiazolyl)amino)methyl)benzoic acid (Example 113), 4-((N-(4-(4-(N-benzyl-N-(4-cyclohexylbenzyl)amino)phenyl)-2-thiazolyl)-N-methylamino)methyl)benzoic acid (Example 114), 4-((N-(4-(4-(4-cyclohexylbenzylamino)phenyl)-2-thiazolyl)-N-methylamino)methyl)benzoic acid (Example 115), 4-((N-cyclohexylmethyl-N-(4-(4-(3,4-dichlorobenzylamino)phenyl)-2-thiazolyl)amino)methyl)benzoic acid (Example 116), 4-((N-(4-(4-(bis(3,4-dichlorobenzyl)amino)phenyl)-2-thiazolyl)-N-cyclohexylmethylamino)methyl)benzoic acid (Example 117), 4-((N-cyclohexylmethyl-N-(4-(4-(N-(3,4-dichlorobenzyl)-N-methylamino)phenyl)-2-thiazolyl)amino)methyl)benzoic acid (Example 118), 4-((N-(4-(4-(N-allyl-N-(4-cyclohexylbenzyl)amino)phenyl)-2-thiazolyl)-N-methylamino)methyl)benzoic acid (Example 119), sodium 4-((N-(4-(4-(4-cyclohexylbenzyloxy)phenyl)-2-thiazolyl)-N-methylamino)methyl)benzoate (Example 120), 4-((N-(4-(4-(4-cyclohexylbenzyloxy)phenyl)-2-thiazolyl)-N-methylamino)methyl)benzoic acid N-methyl-D-glucamine salt (Example 121), 4-((N-(4-(4-(4-cyclohexylbenzyloxy)phenyl)-2-thiazolyl)-N-methylamino)methyl)benzoic acid tris(hydroxymethyl)aminomethane salt (Example 122), 4-((N-(4-(4-(N-benzyl-N-cyclohexylmethylamino)phenyl)-2-thiazolyl)-N-methylamino)methyl)benzoic acid (Example 123), 4-((N-(4-(4-(N-cyclohexylmethyl-N-(4-trifluoromethylbenzyl)amino)phenyl)-2-thiazolyl)-N-methylamino)methyl)benzoic acid (Example 124), sodium 4-(4-(4-(4-cyclohexylbenzyloxy)phenyl)-2-thiazolecarbonyl)benzoate (Example 125), potassium 4-(4-(4-(4-cyclohexylbenzyloxy)phenyl)-2-thiazolecarbonyl)benzoate (Example 126), 4-((N-isopropyl-N-(4-(4-(3-piperidinobenzyloxy)phenyl)-2-thiazolyl)amino)methyl)benzoic acid dihydrochloride (Example 127),
4-(N-(4-(4-(3,4-dichlorobenzylamino)phenyl)-2-thiazolyl)-N-methylamino)benzoic acid (Example 128),
4-(N-cyclohexylmethyl-N-(4-(4-(3,4-dichlorobenzylamino)phenyl)-2-thiazolyl)amino)benzoic acid (Example 129),
4-(N-cyclohexylmethyl-N-(4-(4-(4-isopropylbenzylamino)phenyl)-2-thiazolyl)amino)benzoic acid (Example 130),
4-(N-cyclohexylmethyl-N-(4-(4-(4-isobutylbenzylamino)phenyl)-2-thiazolyl)amino)benzoic acid (Example 131),
4-(N-(4-(4-(N-(4-cyclohexylbenzyl)-N-methylamino)phenyl)-2-thiazolyl)-N-methylamino)benzoic acid (Example 132),
4-(N-methyl-N-(4-(4-(4-trifluoromethylbenzylamino)phenyl)-2-thiazolyl)amino)benzoic acid (Example 133),
4-(N-cyclohexylmethyl-N-(4-(4-(4-trifluoromethylbenzylamino)phenyl)-2-thiazolyl)amino)benzoic acid (Example 134),
4-((N-(4-(4-(N-cyclohexylmethyl-N-(4-trifluoromethylbenzyl)amino)phenyl)-2-thiazolyl)-N-isopropylamino)methyl)benzoic acid (Example 135),
4-((N-isopropyl-N-(4-(4-(N-(tetrahydropyran-4-ylmethyl)-N-(4-trifluoromethylbenzyl)amino)phenyl)-2-thiazolyl)amino)methyl)benzoic acid (Example 136),
4-(N-methyl-N-(4-(4-(N-methyl-N-(4-trifluoromethylbenzyl)amino)phenyl)-2-thiazolyl)amino)benzoic acid (Example 137),
4-(4-(3-(4-cyclohexylbenzyloxy)phenyl)-2-thiazolylamino)benzoic acid (Example 138),
4-(N-(4-(3-(4-cyclohexylbenzyloxy)phenyl)-2-thiazolyl)-N-methylamino)benzoic acid (Example 139),
4-(N-(4-(3-(4-cyclohexylbenzyloxy)phenyl)-2-thiazolyl)-N-ethylamino)benzoic acid (Example 140),
4-(N-(4-(3-(4-cyclohexylbenzyloxy)phenyl)-2-thiazolyl)-N-isopropylamino)benzoic acid (Example 141),
4-(N-(4-(3-(4-cyclohexylbenzyloxy)phenyl)-2-thiazolyl)-N-cyclohexylmethylamino)benzoic acid (Example 142),
4-((N-(4-(3-(4-cyclohexylbenzyloxy)phenyl)-2-thiazolyl)-N-methylamino)methyl)benzoic acid (Example 143),
4-((N-(4-(3-(4-cyclohexylbenzyloxy)phenyl)-2-thiazolyl)-N-isopropylamino)methyl)benzoic acid (Example 144),
4-((N-(4-(3-(4-cyclohexylbenzyloxy)phenyl)-2-thiazolyl)-N-cyclohexylmethylamino)methyl)benzoic acid (Example 145),
4-((N-(4-(3-(4-cyclohexylbenzoylamino)phenyl)-2-thiazolyl)-N-isopropylamino)methyl)benzoic acid (Example 146),
4-((N-(4-(3-(4-cyclohexylbenzenesulfonylamino)phenyl)-2-thiazolyl)-N-isopropylamino)methyl)benzoic acid (Example 147),
4-(4-(2-benzyloxy-5-chlorophenyl)-2-thiazolylamino)benzoic acid (Example 148),
4-(1-(4-(2-benzyloxy-5-chlorophenyl)-2-thiazolyl)-1-methylethyl)benzoic acid (Example 149),
4-(4-(2-benzyloxy-5-chlorophenyl)-2-thiazolylamino)-3-(2-cyclohexylethoxy)benzoic acid (Example 150),
4-(N-(4-(2-benzyloxy-5-chlorophenyl)-2-thiazolyl)-N-methylamino)benzoic acid (Example 151),
4-(N-(4-(2-benzyloxy-5-chlorophenyl)-2-thiazolyl)-N-(2-cyclohexylethyl)amino)benzoic acid (Example 152),
4-(N-(4-(2-benzyloxy-5-chlorophenyl)-2-thiazolyl)-N-(2-phenoxyethyl)amino)benzoic acid (Example 153),
4-(4-(2-benzyloxy-5-methoxyphenyl)-2-thiazolylamino)benzoic acid (Example 154),
4-(4-(5-methoxy-2-(4-trifluoromethylbenzyloxy)phenyl)-2-thiazolylamino)benzoic acid (Example 155),
3-benzyloxy-4-(4-(2-benzyloxy-5-methoxyphenyl)-2-thiazolylamino)benzoic acid (Example 156),
4-(4-(2-(4-cyclohexylbenzyloxy)-5-methoxyphenyl)-2-thiazolylamino)benzoic acid (Example 157),
5-(4-(2-benzyloxy-5-chlorophenyl)-2-thiazolylmethyl)-2-hydroxybenzoic acid (Example 158),
4-(N-(4-(2-benzyloxy-5-chlorophenyl)-2-thiazolyl)-N-(4-trifluoromethylbenzyl)amino)benzoic acid (Example 159),
4-(N-(4-(2-benzyloxy-5-chlorophenyl)-2-thiazolyl)-N-cyclohexylmethylamino)benzoic acid (Example 160),
4-((N-(4-(2-benzyloxy-5-chlorophenyl)-2-thiazolyl)-N-isopropylamino)methyl)benzoic acid (Example 161),
4-((4-(2-benzyloxy-5-chlorophenyl)-2-thiazolylamino)methyl)benzoic acid (Example 162),
4-((N-(4-(2-benzyloxy-5-chlorophenyl)-2-thiazolyl)-N-methylamino)methyl)benzoic acid (Example 163),
4-((N-(4-(2-benzyloxy-5-chlorophenyl)-2-thiazolyl)-N-(2-cyclohexylethyl)amino)methyl)benzoic acid (Example 164),
4-((N-(4-(5-chloro-2-(4-trifluoromethylbenzyloxy)phenyl)-2-thiazolyl)-N-(2-cyclohexylethyl)amino)methyl)benzoic acid (Example 165),
4-((N-(2-cyclohexylethyl)-N-(4-(5-methoxy-2-(4-trifluoromethylbenzyloxy)phenyl)-2-thiazolyl)amino)methyl)benzoic acid (Example 166),
4-(N-(4-(2-benzyloxy-5-chlorophenyl)-2-thiazolyl)-N-(3,4-dichlorobenzyl)amino)benzoic acid (Example 167),
4-(N-(4-(2-benzyloxy-5-chlorophenyl)-2-thiazolyl)-N-(3-methylbutyl)amino)benzoic acid (Example 168),
4-(N-(4-(2-benzyloxy-5-methoxyphenyl)-2-thiazolyl)-N-(2-cyclohexylethyl)amino)benzoic acid (Example 169),
4-(N-(2-cyclohexylethyl)-N-(4-(5-methoxy-2-(4-trifluoromethylbenzyloxy)phenyl)-2-thiazolyl)amino)benzoic acid (Example 170),
3-(2-cyclohexylethoxy)-4-(4-(5-methoxy-2-(4-trifluoromethylbenzyloxy)phenyl)-2-thiazolylamino)benzoic acid (Example 171),
3-(N-(4-(2-benzyloxy-5-chlorophenyl)-2-thiazolyl)-N-(2-cyclohexylethyl)amino)benzoic acid (Example 172),
4-(4-(5-chloro-2-(4-isopropylbenzyloxy)phenyl)-2-thiazolylamino)benzoic acid (Example 173),
4-(N-(4-(2-benzyloxy-5-fluorophenyl)-2-thiazolyl)-N-(2-cyclohexylethyl)amino)benzoic acid (Example 174),
4-(N-(4-(2-benzyloxy-5-methylphenyl)-2-thiazolyl)-N-(2-cyclohexylethyl)amino)benzoic acid (Example 175),
4-(N-(4-(5-chloro-2-(4-isopropylbenzyloxy)phenyl)-2-thiazolyl)-N-(2-cyclohexylethyl)amino)benzoic acid (Example 176),
4-(N-(4-(5-chloro-2-(4-trifluoromethylbenzyloxy)phenyl)-2-thiazolyl)-N-(2-cyclohexylethyl)amino)benzoic acid (Example 177),
4-(N-(4-(5-chloro-2-(3,4-dichlorobenzyloxy)phenyl)-2-thiazolyl)-N-(2-cyclohexylethyl)amino)benzoic acid (Example 178),
4-(4-(5-chloro-2-(4-trifluoromethylbenzyloxy)phenyl)-2-thiazolylamino)-3-(2-cyclohexylethoxy)benzoic acid (Example 179),
3-benzyloxy-4-(4-(5-methoxy-2-(4-trifluoromethylbenzyloxy)phenyl)-2-thiazolylamino)benzoic acid (Example 180),
3-(N-(4-(2-benzyloxy-5-chlorophenyl)-2-thiazolyl)-N-cyclohexylmethylamino)benzoic acid (Example 181),
4-(N-butyl-N-(4-(5-chloro-2-(4-trifluoromethylbenzyloxy)phenyl)-2-thiazolyl)amino)benzoic acid (Example 182), 4-(N-(4-(6-(3,4-dichlorobenzyloxy)-2-benzooxazolyl)-2-thiazolyl)-N-isopropylamino)benzoic acid (Example 183), 4-(N-(2-cyclohexylethyl)-N-(4-(6-(3,4-dichlorobenzyloxy)-2-benzooxazolyl)-2-thiazolyl)amino)benzoic acid (Example 184), 4-(N-(2-cyclohexylethyl)-N-(4-(5-(3,4-dichlorobenzyloxy)-2-benzoimidazolyl)-2-thiazolyl)amino)benzoic acid hydrochloride (Example 185), 4-(4-(5-(3,4-dichlorobenzyloxy)-2-benzoimidazolyl)-2-thiazolylamino)benzoic acid hydrochloride (Example 186), 4-(N-cyclohexylmethyl-N-(4-(6-(3,4-dichlorobenzyloxy)-2-benzooxazolyl)-2-thiazolyl)amino)benzoic acid (Example 187), 4-(N-(4-(6-(4-tert-butylbenzyloxy)-2-benzooxazolyl)-2-thiazolyl)-N-cyclohexylmethylamino)benzoic acid (Example 188), 4-(N-(4-(6-(2,4-bis(trifluoromethyl)benzyloxy)-2-benzooxazolyl)-2-thiazolyl)-N-cyclohexylmethylamino)benzoic acid (Example 189), 4-(N-cyclohexylmethyl-N-(4-(6-(3,4-difluorobenzyloxy)-2-benzooxazolyl)-2-thiazolyl)amino)benzoic acid (Example 190), 4-(N-cyclohexylmethyl-N-(4-(6-(3,5-dimethoxybenzyloxy)-2-benzooxazolyl)-2-thiazolyl)amino)benzoic acid (Example 191), 4-((N-(4-(4-cyclopentyloxyphenyl)-2-thiazolyl)-N-isopropylamino)methyl)benzoic acid (Example 192), 4-((N-(4-(4-dicyclohexylmethoxyphenyl)-2-thiazolyl)-N-isopropylamino)methyl)benzoic acid hydrochloride (Example 193), cis-4-((N-(4-(4-(N-(4-(4-hydroxycyclohexyl)benzyl)-N-methylamino)phenyl)-2-thiazolyl)-N-methylamino)methyl)benzoic acid (Example 194), 4-((N-methyl-N-(4-(4-(N-methyl-N-(4-(4-oxocyclohexyl)benzyl)amino)phenyl)-2-thiazolyl)amino)methyl)benzoic acid (Example 195), trans-4-((N-(4-(4-(N-(4-(4-hydroxycyclohexyl)benzyl)-N-methylamino)phenyl)-2-thiazolyl)-N-methylamino)methyl)benzoic acid (Example 196), 4-((N-(4-(3-(4-cyclohexylbenzylamino)phenyl)-2-thiazolyl)-N-methylamino)methyl)benzoic acid (Example 197), 4-((N-(4-(4-(N-(4-cyclohexylbenzyl)-N-(2-methoxyacetyl)amino)phenyl)-2-thiazolyl)-N-methylamino)methyl)benzoic acid (Example 198), 4-((N-(4-(4-(N-(4-cyclohexylbenzyl)-N-(2-hydroxyacetyl)amino)phenyl)-2-thiazolyl)-N-methylamino)methyl)benzoic acid (Example 199), sodium 4-((N-(4-(3-(N-(4-cyclohexylbenzyl)-N-methylamino)phenyl)-2-thiazolyl)-N-methylamino)methyl)benzoate (Example 200), 4-((N-(4-(3-(N-acetyl-N-(4-cyclohexylbenzyl)amino)phenyl)-2-thiazolyl)-N-methylamino)methyl)benzoic acid (Example 201), 4-((N-(4-(4-(N-(4-cyclohexylbenzyl)-N-methanesulfonylamino)phenyl)-2-thiazolyl)-N-methylamino)methyl)benzoic acid (Example 202), 4-((N-(4-(4-(N-(4-cyclohexylbenzyl)-N-(2-hydroxyethyl)amino)phenyl)-2-thiazolyl)-N-methylamino)methyl)benzoic acid (Example 203), 3-((N-(4-(4-(N-(4-cyclohexylbenzyl)-N-methylamino)phenyl)-2-thiazolyl)-N-methylamino)methyl)benzoic acid (Example 204), cis-4-((N-(4-(4-(N-(4-(3-hydroxycyclohexyl)benzyl)-N-methylamino)phenyl)-2-thiazolyl)-N-methylamino)methyl)benzoic acid (Example 205), trans-4-((N-(4-(4-(N-(4-(3-hydroxycyclohexyl)benzyl)-N-methylamino)phenyl)-2-thiazolyl)-N-methylamino)methyl)benzoic acid (Example 206), 4-((N-methyl-N-(4-(4-(N-methyl-N-(4-(3-oxocyclohexyl)benzyl)amino)phenyl)-2-thiazolyl)amino)methyl)benzoic acid (Example 207), 4-((N-(4-(4-(N-(4-(4,4-dichlorocyclohexyl)benzyl)-N-methylamino)phenyl)-2-thiazolyl)-N-methylamino)methyl)benzoic acid (Example 208), 4-((N-(4-(4-(N-(4-(4,4-difluorocyclohexyl)benzyl)-N-methylamino)phenyl)-2-thiazolyl)-N-methylamino)methyl)benzoic acid (Example 209), 4-((N-methyl-N-(4-(4-(N-methyl-N-(4-(tetrahydropyran-4-yl)benzyl)amino)phenyl)-2-thiazolyl)amino)methyl)benzoic acid (Example 210), 4-((N-(4-(4-(N-(4-(1-acetylpiperidin-4-yl)benzyl)-N-methylamino)phenyl)-2-thiazolyl)-N-methylamino)methyl)benzoic acid (Example 211), 4-((N-(4-(4-(N-(4-cyclopentylbenzyl)-N-methylamino)phenyl)-2-thiazolyl)-N-methylamino)methyl)benzoic acid (Example 212), trans-4-((N-methyl-N-(4-(4-(N-methyl-N-(4-phenylcyclohexylmethyl)amino)phenyl)-2-thiazolyl)amino)methyl)benzoic acid (Example 213), cis-4-((N-methyl-N-(4-(4-(N-methyl-N-(4-phenylcyclohexylmethyl)amino)phenyl)-2-thiazolyl)amino)methyl)benzoic acid (Example 214), 4-((N-(4-(4-(N-(4-(4,4-dimethylcyclohexyl)benzyl)-N-methylamino)phenyl)-2-thiazolyl)-N-methylamino)methyl)benzoic acid (Example 215), sodium 4-((N-(4-(4-(N-(4-(4,4-dimethylcyclohexyl)benzyl)-N-methylamino)phenyl)-2-thiazolyl)-N-methylamino)methyl)benzoate (Example 216), 4-((N-cyclohexylmethyl-N-(4-(6-(3,4-dichlorobenzyloxy)-2-benzooxazolyl)-2-thiazolyl)amino)methyl)benzoic acid (Example 217), 4-((N-methyl-N-(4-(4-(N-methyl-N-(4-(4-methylcyclohexyl)benzyl)amino)phenyl)-2-thiazolyl)amino)methyl)benzoic acid (Example 218), 4-((N-(4-(4-(N-(2-cyclohexylbenzyl)-N-methylamino)phenyl)-2-thiazolyl)-N-methylamino)methyl)benzoic acid (Example 219), 4-((N-(4-(6-benzyloxy-2-benzooxazolyl)-2-thiazolyl)-N-cyclohexylmethylamino)methyl)benzoic acid (Example 220), 4-((N-cyclohexylmethyl-N-(4-(6-phenethyloxy-2-benzooxazolyl)-2-thiazolyl)amino)methyl)benzoic acid (Example 221), 4-((N-methyl-N-(4-(4-(N-methyl-N-(4-phenylbutyl)amino)phenyl)-2-thiazolyl)amino)methyl)benzoic acid (Example 222), 4-((N-(4-(4-(N-(2-(2-indanyl)ethyl)-N-methylamino)phenyl)-2-thiazolyl)-N-methylamino)methyl)benzoic acid (Example 223), 4-((N-(4-(4-(N-(2-(3,4-dichlorophenyl)ethyl)-N-methylamino)phenyl)-2-thiazolyl)-N-methylamino)methyl)benzoic acid (Example 224), 4-((N-methyl-N-(4-(4-(N-methyl-N-(3-phenylpropyl)amino)phenyl)-2-thiazolyl)amino)methyl)benzoic acid (Example 225), 4-((N-(4-(6-(N-(4-cyclohexylbenzyl)-N-methylamino)-3-pyridyl)-2-thiazolyl)-N-methylamino)methyl)benzoic acid (Example 226), 4-((N-(2'-(N-(4-cyclohexylbenzyl)-N-methylamino)-4'-methyl-4,5'-bithiazolyl-2-yl)-N-methylamino)methyl)benzoic acid (Example 227), 4-((N-(4-(2-chloro-6-(N-(4-cyclohexylbenzyl)-N-methylamino)-4-pyridyl)-2-thiazolyl)-N-methylamino)methyl) benzoic acid (Example 228), 4-((N-(4-(4-(N-(4-(2,2-dimethylpropyl)benzyl)-N-methylamino)phenyl)-2-thiazolyl)-N-methylamino)methyl) benzoic acid (Example 229), 4-((N-methyl-N-(4-(4-(N-methyl-N-(4-(1-propylbutyl)benzyl)amino)phenyl)-2-thiazolyl)amino)methyl)benzoic acid (Example 230), 4-((N-(4-(2-(4-cyclohexylphenyl)-1H-benzoimidazol-5-yl)-2-thiazolyl)-N-methylamino)methyl)benzoic acid (Example 231), 4-((N-(4-(5-chloro-6-(N-(4-cyclohexylbenzyl)-N-methylamino)-3-pyridyl)-2-thiazolyl)-N-methylamino)methyl) benzoic acid (Example 232), 4-((N-(4-(4-(N-(4-tert-butylbenzyl)-N-methylamino)phenyl)-2-thiazolyl)-N-methylamino)methyl)benzoic acid (Example 233), 4-((N-methyl-N-(4-(4-(N-methyl-N-(4-trifluoromethylbenzyl)amino)phenyl)-2-thiazolyl)amino)methyl)benzoic acid (Example 234), 4-((N-(4-(4-(N-(2-(4-tert-butylphenyl)ethyl)-N-methylamino)phenyl)-2-thiazolyl)-N-methylamino)methyl) benzoic acid (Example 235), 4-((N-methyl-N-(4-(4-(N-methyl-N-(2-(4-trifluoromethylphenyl)ethyl)amino)phenyl)-2-thiazolyl)amino)methyl) benzoic acid (Example 236), 4-((N-(4-(4-(N-(2-(4-dimethylaminophenyl)ethyl)-N-methylamino)phenyl)-2-thiazolyl)-N-methylamino)methyl) benzoic acid (Example 237), 4-((N-methyl-N-(4-(4-(N-methyl-N-(2-(4-morpholinophenyl)ethyl)amino)phenyl)-2-thiazolyl)amino)methyl)benzoic acid (Example 238), 4-((N-methyl-N-(4-(4-(4-phenyl-1-piperazinylmethyl)phenyl)-2-thiazolyl)amino)methyl)benzoic acid (Example 239), 4-((N-(4-(4-(4-benzyl-1-piperazinylmethyl)phenyl)-2-thiazolyl)-N-methylamino)methyl)benzoic acid (Example 240), 4-((N-(4-(4-(N-(4-(1-ethylpropyl)benzyl)-N-methylamino) phenyl)-2-thiazolyl)-N-methylamino)methyl)benzoic acid (Example 241), 4-((N-(4-(3-chloro-4-(N-(4-cyclohexylbenzyl)-N-methylamino)phenyl)-2-thiazolyl)-N-methylamino)methyl) benzoic acid (Example 242), benzyl 4-(4-(2-(N-(4-carboxybenzyl)-N-methylamino)-4-thiazolyl)benzyl)-piperazine-1-carboxylate (Example 243), 4-((N-(4-(4-(N-(4-tert-butylbenzyl)-N-methylamino)-3-chlorophenyl)-2-thiazolyl)-N-methylamino)methyl)benzoic acid (Example 244), 4-((N-(4-(4-(N-(4-isobutylsulfanylbenzyl)-N-methylamino) phenyl)-2-thiazolyl)-N-methylamino)methyl)benzoic acid (Example 245), 4-((N-(4-(4-(N-(4-cyclohexylbenzyl)-N-methylamino)phenyl)-2-thiazolyl)-N-methylamino)methyl)benzoic acid lysine salt (Example 246), 4-((4-(4-(N-(4-cyclohexylbenzyl)-N-methylamino)phenyl)-2-thiazolylamino)methyl)benzoic acid (Example 247), 3-oxo-1,3-dihydroisobenzofuran-1-yl 4-((N-(4-(4-(4-cyclohexylbenzyloxy)phenyl)-2-thiazolyl)-N-methylamino) methyl)benzoate (Example 248), ethyl 4-((N-(4-(4-(4-cyclohexylbenzyloxy)phenyl)-2-thiazolyl)-N-methylamino)methyl)benzoate (Example 249), 1-acetoxyethyl 4-((N-(4-(4-(4-cyclohexylbenzyloxy)phenyl)-2-thiazolyl)-N-methylamino)methyl)benzoate (Example 250), 4-((N-(4-(4-(4-cyclohexylbenzyloxy)phenyl)-2-thiazolyl)-N-methylamino)methyl)benzoic acid methanesulfonate (Example 251), 4-((N-(4-(4-(4-cyclohexylbenzyloxy)phenyl)-2-thiazolyl)-N-methylamino)methyl)benzoic acid hydrochloride (Example 252), potassium 4-((N-(4-(4-(N-(4-cyclohexylbenzyl)-N-methylamino)phenyl)-2-thiazolyl)-N-methylamino)methyl) benzoate (Example 253), 4-((N-(4-(4-(N-(4-cyclohexylbenzyl)-N-methylamino)phenyl)-2-thiazolyl)-N-methylamino)methyl)benzoic acid hydrochloride (Example 254), 4-((N-(4-(4-(N-(4-cyclohexylbenzyl)-N-methylamino)phenyl)-2-thiazolyl)-N-methylamino)methyl)benzoic acid methanesulfonate (Example 255), 4-((N-(4-(4-(N-(4-cyclohexylbenzyl)-N-methylamino)phenyl)-2-thiazolyl)-N-methylamino)methyl)benzoic acid tris(hydroxymethyl)aminomethane salt (Example 256), 4-((N-(4-(4-(N-(4-cyclohexylbenzyl)-N-methylamino)phenyl)-2-thiazolyl)-N-methylamino)methyl)benzoic acid sulfate (Example 257), 4-(N-(4-(4-(4-cyclohexylbenzylamino)phenyl)-2-thiazolyl)-N-methylamino)benzoic acid hydrochloride (Example 258), 4-(N-(4-(4-(4-cyclohexylbenzylamino)phenyl)-2-thiazolyl)-N-methylamino)benzoic acid methanesulfonate (Example 259), 4-(N-(4-(4-(4-cyclohexylbenzylamino)phenyl)-2-thiazolyl)-N-methylamino)benzoic acid tris(hydroxymethyl)aminomethane salt (Example 260), 4-(N-(4-(4-(4-cyclohexylbenzylamino)phenyl)-2-thiazolyl)-N-methylamino)benzoic acid N-methyl-D-glucamine salt (Example 261), 4-(N-(4-(4-(4-cyclohexylbenzylamino)phenyl)-2-thiazolyl)-N-methylamino)benzoic acid sulfate (Example 262), sodium 4-(N-(4-(4-(4-cyclohexylbenzylamino)phenyl)-2-thiazolyl)-N-methylamino)benzoate (Example 263), 4-((N-(4-(4-(4-cyclohexylbenzyloxy)phenyl)-2-thiazolyl)-N-methylamino)methyl)benzoic acid 1/2 sulfate (Example 264), 4-((N-(4-(4-(4-cyclohexylbenzyloxy)phenyl)-2-thiazolyl)-N-methylamino)methyl)benzoic acid histidine salt (Example 265), 4-((N-(4-(4-(4-cyclohexylbenzyloxy)phenyl)-2-thiazolyl)-N-methylamino)methyl)benzoic acid lysine salt (Example 266), tert-butoxycarbonylmethyl 4-((N-(4-(4-(4-cyclohexylbenzyloxy)phenyl)-2-thiazolyl)-N-methylamino)methyl)benzoate (Example 267), 2,2-dimethylpropionyloxymethyl 4-((N-(4-(4-(4-cyclohexylbenzyloxy)phenyl)-2-thiazolyl)-N-methylamino)methyl) benzoate (Example 268), 1-ethoxycarbonyloxyethyl 4-((N-(4-(4-(4-cyclohexylbenzyloxy)phenyl)-2-thiazolyl)-N-methylamino)methyl)benzoate (Example 269), acetoxymethyl 4-((N-(4-(4-(4-cyclohexylbenzyloxy)phenyl)-2-thiazolyl)-N-methylamino)methyl)benzoate (Example 270), 1-isopropoxycarbonyloxyethyl 4-((N-(4-(4-(4-cyclohexylbenzyloxy)phenyl)-2-thiazolyl)-N-methylamino)methyl) benzoate (Example 271), 1-cyclohexyloxycarbonyloxyethyl 4-((N-(4-(4-(4-cyclohexylbenzyloxy)phenyl)-2-thiazolyl)-N-methylamino)methyl)benzoate (Example 272),
5-methyl-2-oxo-1,3-dioxl-4-ylmethyl 4-((N-(4-(4-(4-cyclohexylbenzyloxy)phenyl)-2-thiazolyl)-N-methylamino)methyl)benzoate (Example 273),
4-(N-(4-(4-(4-cyclohexylbenzylamino)phenyl)-2-thiazolyl)-N-methylamino)benzoic acid lysine salt (Example 274).

The structural formulas and property values of the compound of each Example are shown in Tables 1 to 67.

TABLE 1

| Ex. | Structural formula | m.p. (° C.) |
|---|---|---|
| 1 | | 180–181 |
| 2 | | 288–291 (dec.) |
| 3 | | 252–253 |
| 4 | | 250 (dec.) |
| 5 | | 250 (dec.) |
| 6 | | 250 (dec.) |

TABLE 2

| Ex. | Structural formula | m.p. (° C.) |
|---|---|---|
| 7 | | 250 (dec.) |
| 8 | | 250 (dec.) |
| 9 | | 234–236 |

TABLE 3
| Ex. | Structural formula | m.p. (° C.) |
|---|---|---|
| 10 | 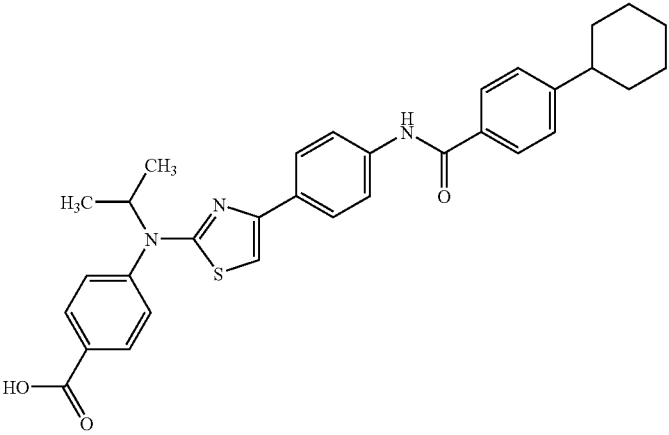 | 230 (dec.) |
| 11 | 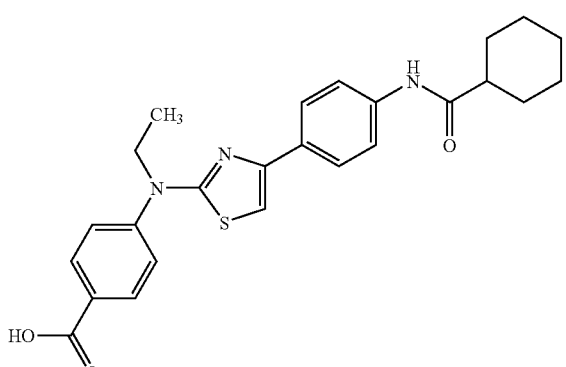 | 250 (dec.) |
| 12 | 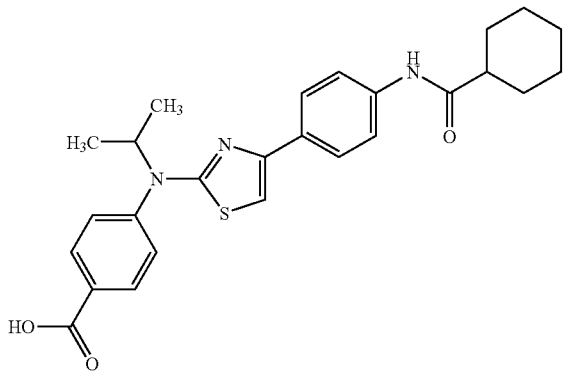 | 230 (dec.) |

TABLE 4

| Ex. | Structural formula | m.p. (° C.) |
| --- | --- | --- |
| 13 | | 231–232 |
| 14 | | 210 (dec.) |
| 15 | | 234–235 |

TABLE 5

| Ex. | Structural formula | m.p. (° C.) |
|-----|-------------------|-------------|
| 16 | | 210 (dec.) |
| 17 | | 230 (dec.) |
| 18 | | 230 (dec.) |
| 19 | | 250 (dec.) |

TABLE 6
| Ex. | Structural formula | m.p. (° C.) |
|---|---|---|
| 20 | 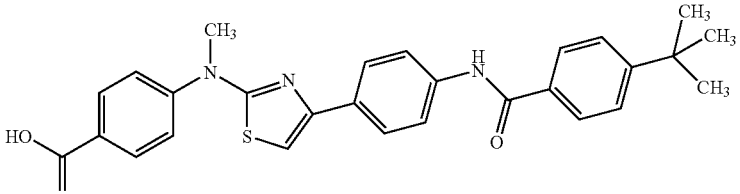 | 250 (dec.) |
| 21 | 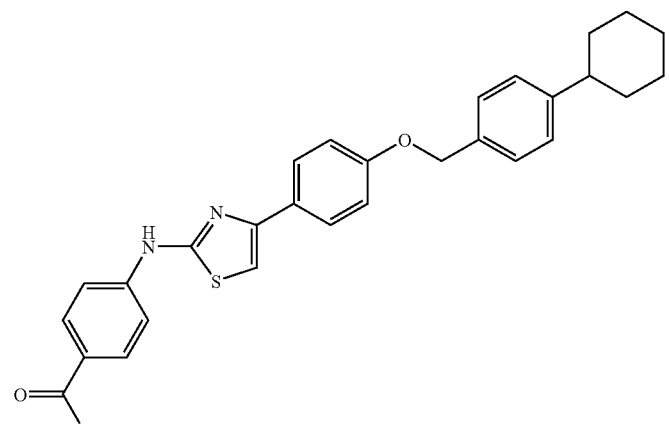 | 250 (dec.) |
| 22 | 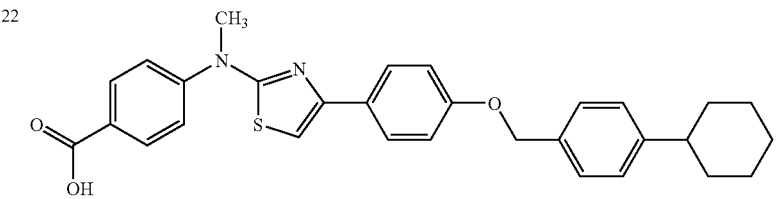 | 250 (dec.) |
| 23 | 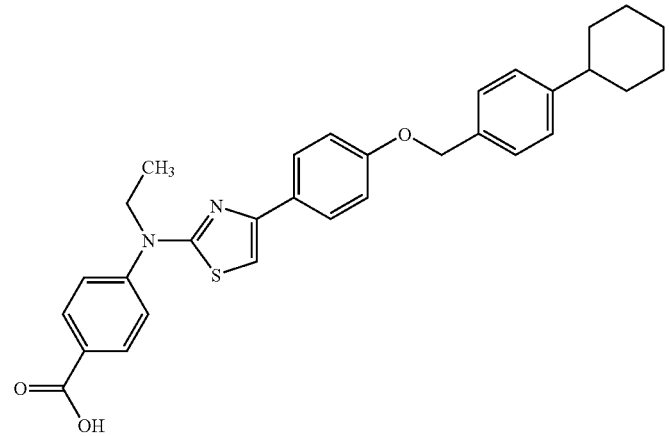 | 239–247 |

TABLE 7

| Ex. | Structural formula | m.p. (° C.) |
|---|---|---|
| 24 | | 238–240 |
| 25 | | 230 (dec.) |

TABLE 8

| Ex. | Structural formula | m.p. (° C.) |
|---|---|---|
| 26 | | 230 (dec.) |

TABLE 8-continued

| Ex. | Structural formula | m.p. (° C.) |
|---|---|---|
| 27 | | 230 (dec.) |
| 28 | | 230 (dec.) |

TABLE 9

| Ex. | Structural formula | m.p. (° C.) |
|---|---|---|
| 29 | | 230 (dec.) |

TABLE 9-continued

| Ex. | Structural formula | m.p. (° C.) |
|---|---|---|
| 30 | | 220 (dec.) |
| 31 | | 230 (dec.) |

TABLE 10

| Ex. | Structural formula | m.p. (° C.) |
|---|---|---|
| 32 | | 230 (dec.) |

TABLE 10-continued
| Ex. | Structural formula | m.p. (° C.) |
|---|---|---|
| 33 | 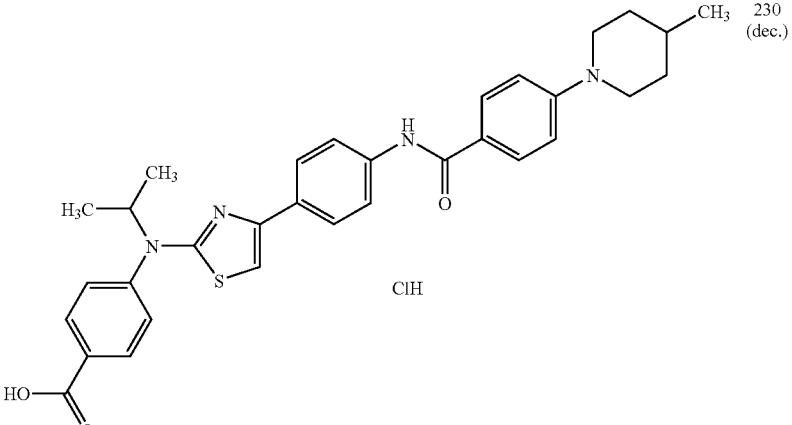 ClH | 230 (dec.) |
| 34 | 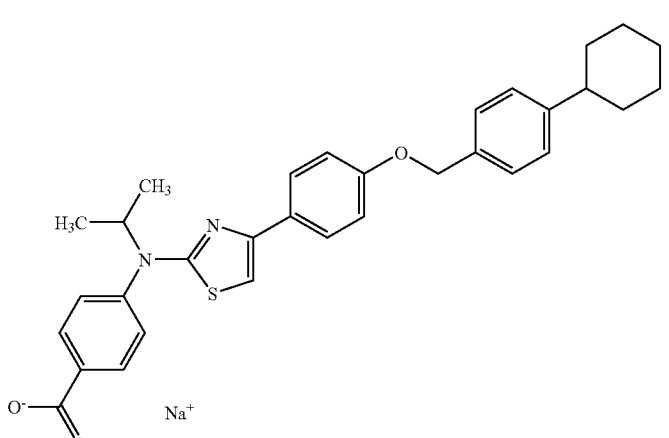 Na⁺ | 230 (dec.) |
TABLE 11
| Ex. | Structural formula | m.p. (° C.) |
|---|---|---|
| 35 | 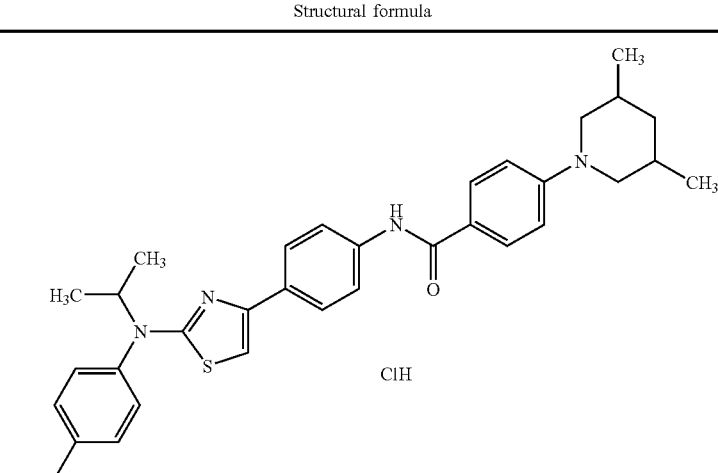 ClH | 152–160 |

TABLE 11-continued
| Ex. | Structural formula | m.p. (° C.) |
|---|---|---|
| 36 | 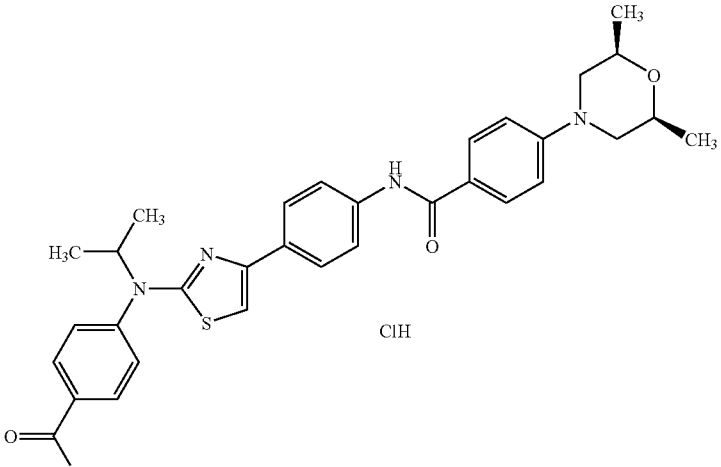 | 230 (dec.) |
TABLE 12
| Ex. | Structural formula | m.p. (° C.) |
|---|---|---|
| 37 | 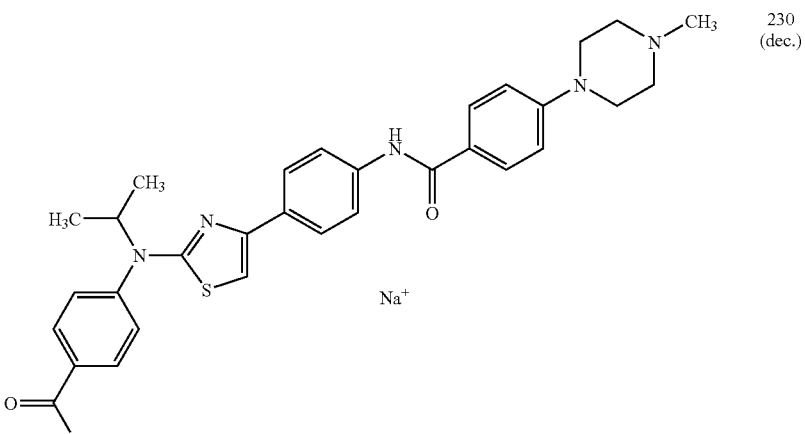 | 230 (dec.) |
| 38 | 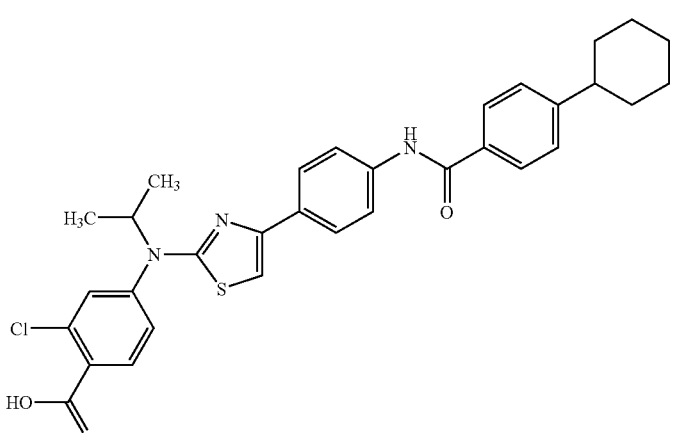 | 220 (dec.) |

TABLE 12-continued
| Ex. | Structural formula | m.p. (° C.) |
|---|---|---|
| 39 | 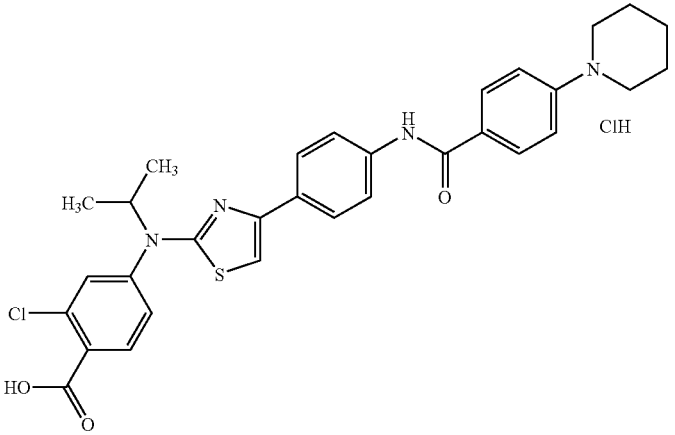 | 220 (dec.) |
TABLE 13
| Ex. | Structural formula | m.p. (° C.) |
|---|---|---|
| 40 | 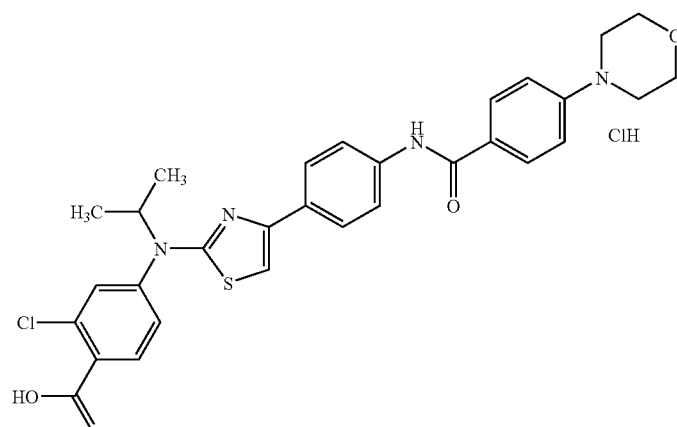 | 220 (dec.) |
| 41 | 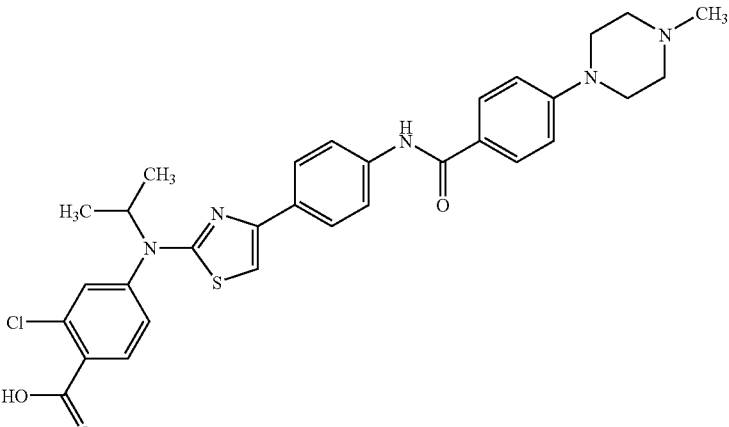 | 220 (dec.) |

TABLE 13-continued
| Ex. | Structural formula | m.p. (° C.) |
|---|---|---|
| 42 | 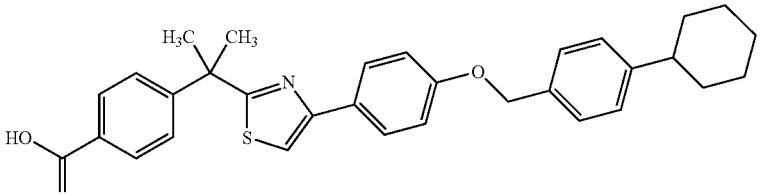 | 219–221 |
| 43 | 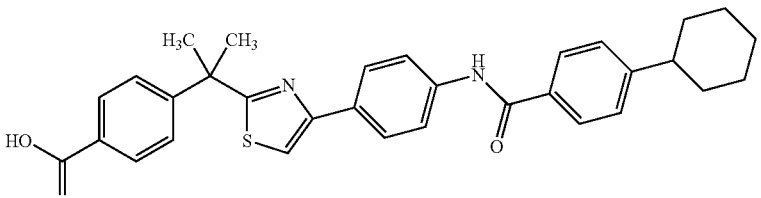 | 262–264 |
TABLE 14
| Ex. | Structural formula | m.p. (° C.) |
|---|---|---|
| 44 | 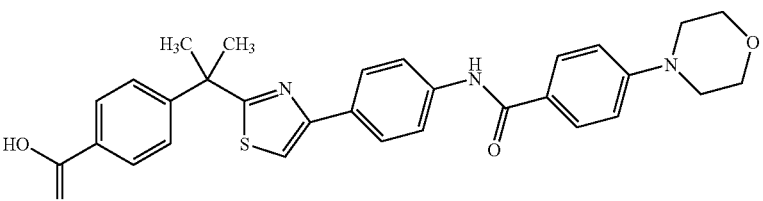 | 290 (dec.) |
| 45 | 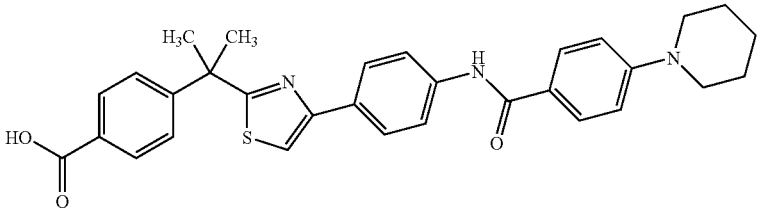 | 268–271 |
| 46 | 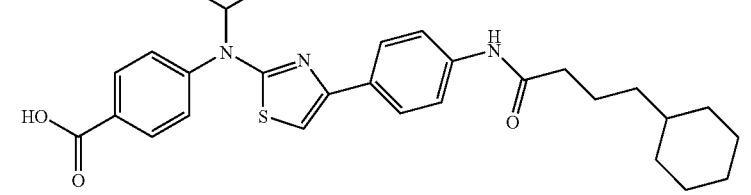 | 230 (dec.) |
| 47 | 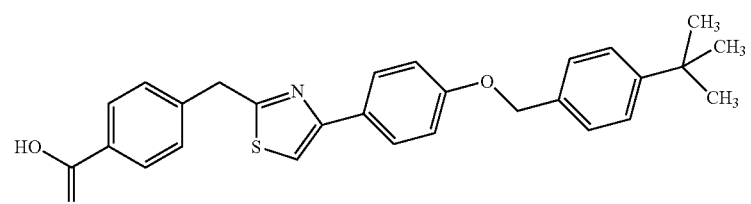 | 223–228 |

TABLE 14-continued

| Ex. | Structural formula | m.p. (° C.) |
|---|---|---|
| 48 | | 235–238 |
| 49 | | 270 (dec.) |

TABLE 15

| Ex. | Structural formula | m.p. (° C.) |
|---|---|---|
| 50 | | 225 (dec.) |
| 51 | | 240 (dec.) |
| 52 | | 153–157 |
| 53 | | 220 (dec.) |

TABLE 15-continued
| Ex. | Structural formula | m.p. (° C.) |
|---|---|---|
| 54 | 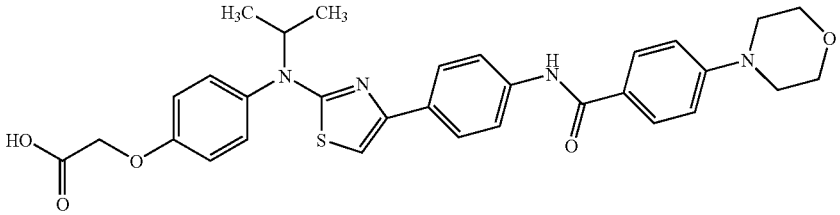 | 250 (dec.) |
TABLE 16
| Ex. | Structural formula | m.p. (° C.) |
|---|---|---|
| 55 | 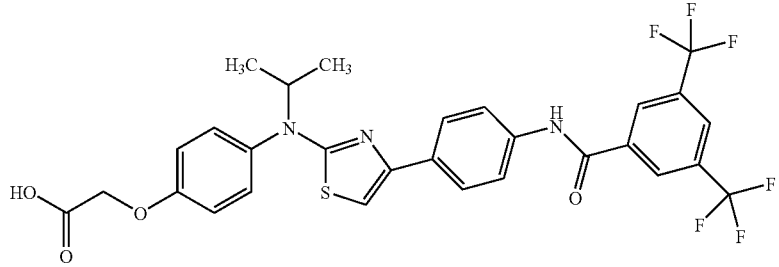 | amorphous |
| 56 | 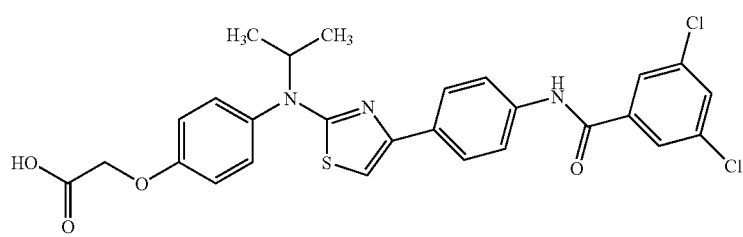 | 192–194 |
| 57 | 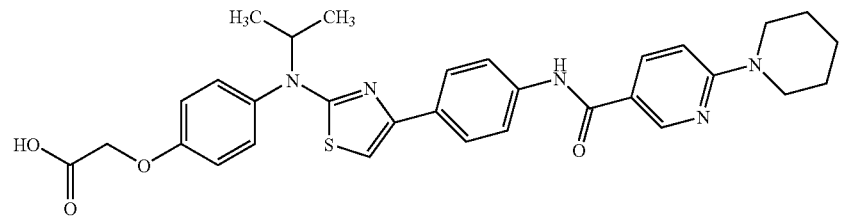 | 237–240 |
| 58 | 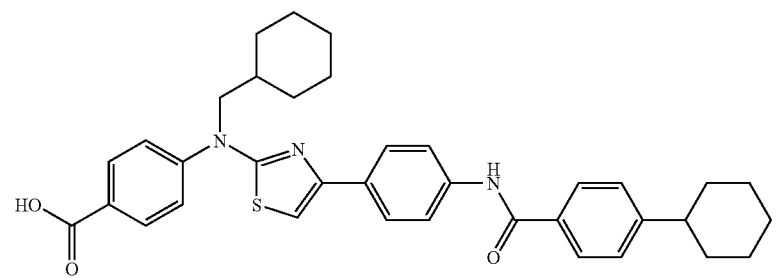 | amorphous |

TABLE 16-continued

| Ex. | Structural formula | m.p. (° C.) |
| --- | --- | --- |
| 59 | | amorphous |

TABLE 17

| Ex. | Structural formula | m.p. (° C.) |
| --- | --- | --- |
| 60 | | amorphous |
| 61 | | 250 (dec.) |
| 62 | | 234 (dec.) |
| 63 | | 250 (dec.) |
| 64 | | 250 (dec.) |

TABLE 18
| Ex. | Structural formula | m.p. (° C.) |
|---|---|---|
| 65 | 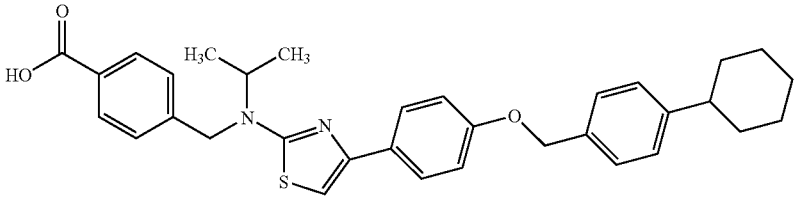 | 233–234 |
| 66 | 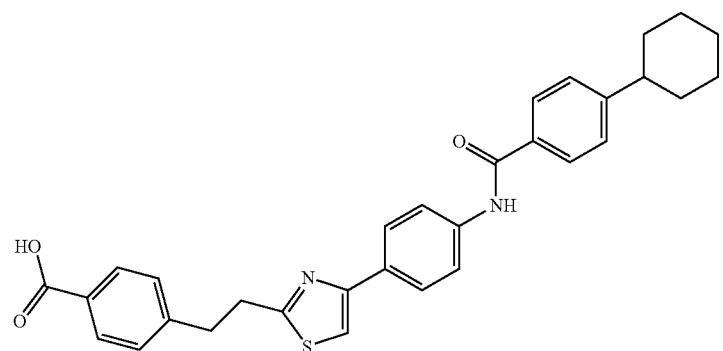 | amorphous |
| 67 | 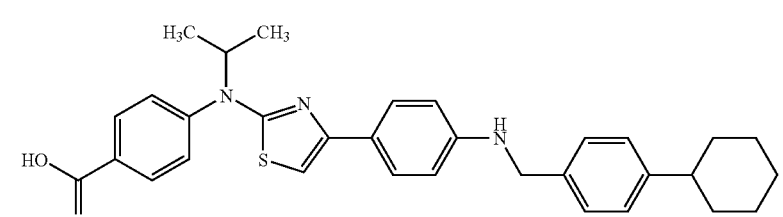 | amorphous |
| 68 | 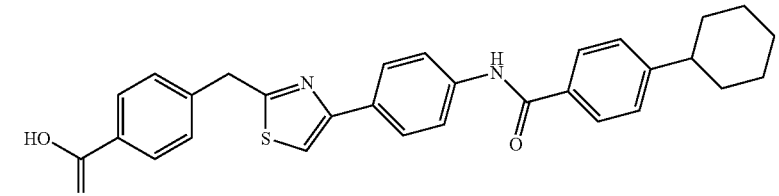 | 230 (dec.) |
| 69 | 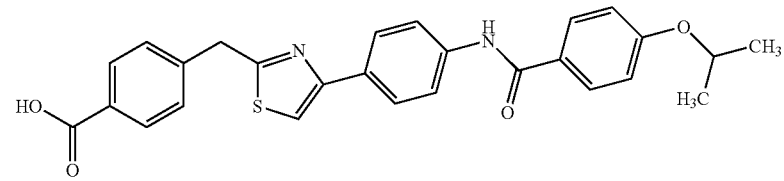 | 230 (dec.) |
| 70 | 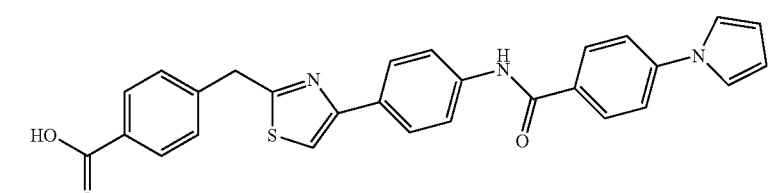 | 220 (dec.) |

TABLE 19

| Ex. | Structural formula | m.p. (° C.) |
| --- | --- | --- |
| 71 | | 259–261 |
| 72 | | 230 (dec.) |
| 73 | | 230 (dec.) |
| 74 | | 230 (dec.) |
| 75 | | amorphous |

TABLE 20

| Ex. | Structural formula | m.p. (° C.) |
|---|---|---|
| 76 | | amorphous |
| 77 | | 180–181 |
| 78 | | 215–216 |
| 79 | | 238–239 |
| 80 | | 221–222 |
| 81 | | amorphous |

TABLE 21

| Ex. | Structural formula | m.p. (° C.) |
|---|---|---|
| 82 | | amorphous |
| 83 | | amorphous |
| 84 | | amorphous |
| 85 | | amorphous |

TABLE 22

| Ex. | Structural formula | m.p. (° C.) |
|---|---|---|
| 86 | | amorphous |
| 87 | | 196–197 |
| 88 | | 259–261 |
| 89 | | 230 (dec.) |
| 90 | | 170–172 |
| 91 | | 248–251 |

TABLE 23

| Ex. | Structural formula | m.p. (° C.) |
|---|---|---|
| 92 | | 230 (dec.) |

TABLE 23-continued

| Ex. | Structural formula | m.p. (° C.) |
|---|---|---|
| 93 | | 168–171 |
| 94 | | 230 (dec.) |
| 95 | | 230 (dec.) |
| 96 | | 236–238 |
| 97 | | 230 (dec.) |

TABLE 24

| Ex. | Structural formula | m.p. (° C.) |
|---|---|---|
| 98 | | 230 (dec.) |

TABLE 24-continued

| Ex. | Structural formula | m.p. (° C.) |
| --- | --- | --- |
| 99 | | 175–178 |
| 100 | | 222–224 |
| 101 | | 230 (dec.) |
| 102 | | 240 |

TABLE 25

| Ex. | Structural formula | m.p. (° C.) |
| --- | --- | --- |
| 103 | | amorphous |

TABLE 25-continued

| Ex. | Structural formula | m.p. (° C.) |
|---|---|---|
| 104 | | 178–180 |
| 105 | | 193–195 |
| 106 | | 132–134 |
| 107 | | amorphous |

TABLE 26

| Ex. | Structural formula | m.p. (° C.) |
|---|---|---|
| 108 | | amorphous |

TABLE 26-continued

| Ex. | Structural formula | m.p. (° C.) |
|---|---|---|
| 109 | | 144–146 |
| 110 | | amorphous |
| 111 | | amorphous |
| 112 | | amorphous |

TABLE 27

| Ex. | Structural formula | m.p. (° C.) |
|---|---|---|
| 113 | | amorphous |
| 114 | | amorphous |
| 115 | | 184 (dec.) |
| 116 | | amorphous |

TABLE 27-continued

| Ex. | Structural formula | m.p. (° C.) |
|---|---|---|
| 117 | | 120 (dec.) |

TABLE 28

| Ex. | Structural formula | m.p. (° C.) |
|---|---|---|
| 118 | | 125–127 |
| 119 | | 139–141 |
| 120 | | 250 (dec.) |
| 121 | | 170–174 |

TABLE 28-continued

| Ex. | Structural formula | m.p. (° C.) |
|---|---|---|
| 122 | | 186–189 |

TABLE 29

| Ex. | Structural formula | m.p. (° C.) |
|---|---|---|
| 123 | | amorphous |
| 124 | | amorphous |
| 125 | | 270 (dec.) |
| 126 | | 270 (dec.) |

TABLE 29-continued

| Ex. | Structural formula | m.p. (° C.) |
|---|---|---|
| 127 | | 135–140 |

TABLE 30

| Ex. | Structural formula | m.p. (° C.) |
|---|---|---|
| 128 | | 223–225 |
| 129 | | 187–189 |
| 130 | | 200–202 |
| 131 | | 167–169 |

TABLE 30-continued

| Ex. | Structural formula | m.p. (° C.) |
|---|---|---|
| 132 | | 185–189 |

TABLE 31

| Ex. | Structural formula | m.p. (° C.) |
|---|---|---|
| 133 | | 230 (dec.) |
| 134 | | 199–203 |
| 135 | | amorphous |

TABLE 31-continued
| Ex. | Structural formula | m.p. (° C.) |
| --- | --- | --- |
| 136 | 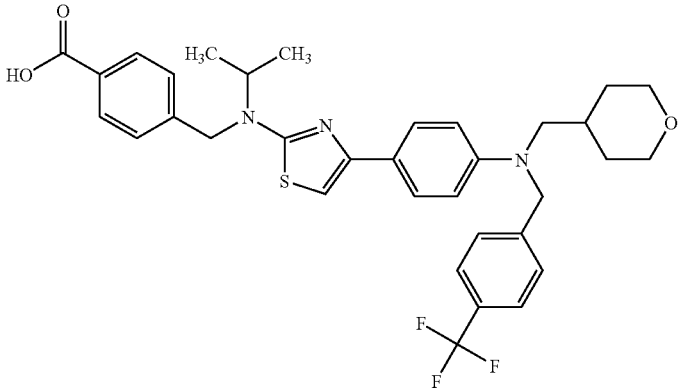 | amorphous |
TABLE 32
| Ex. | Structural formula | m.p. (° C.) |
| --- | --- | --- |
| 137 | 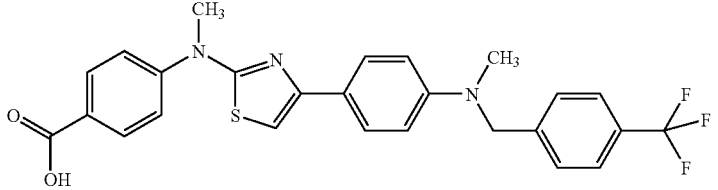 | 218–220 |
| 138 | 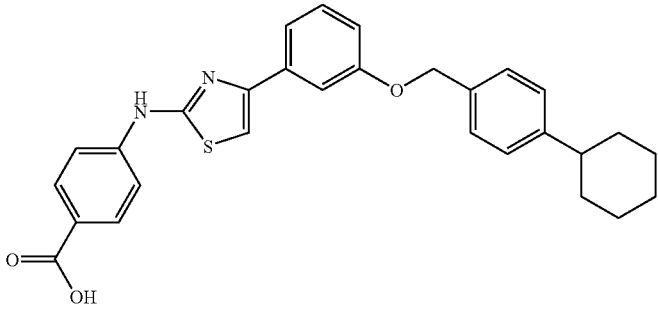 | 235–236 |
| 139 | 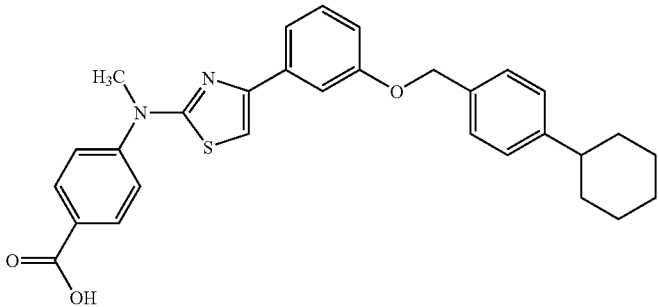 | 250 (dec.) |

TABLE 32-continued
| Ex. | Structural formula | m.p. (° C.) |
|---|---|---|
| 140 | 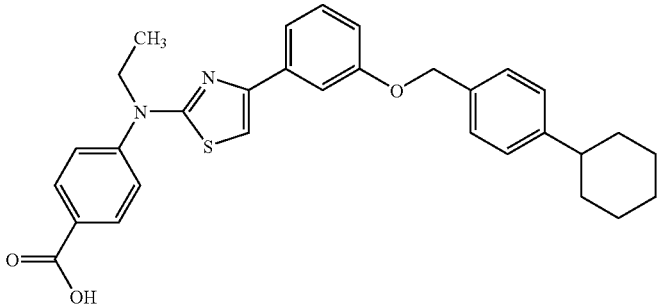 | 179–180 |
TABLE 33
| Ex. | Structural formula | m.p. (° C.) |
|---|---|---|
| 141 | 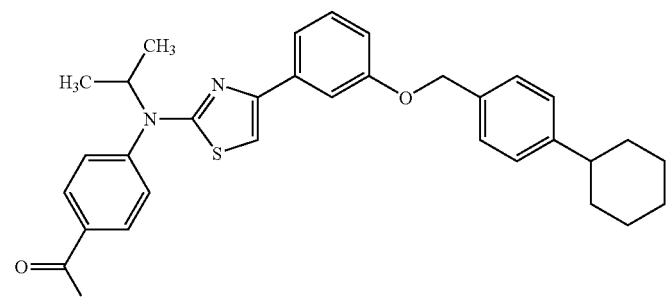 | 189–190 |
| 142 | 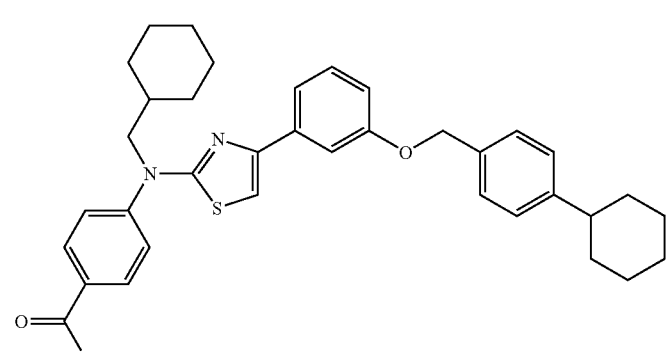 | 195–197 |
| 143 | 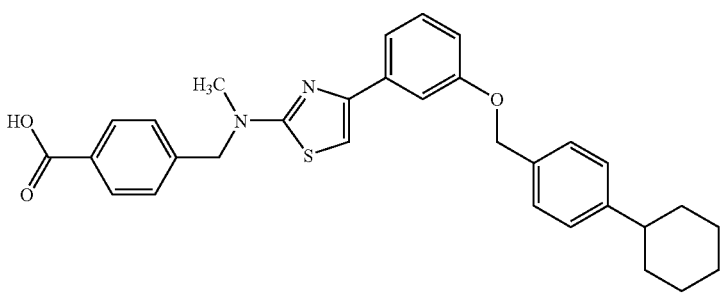 | amorphous |

TABLE 33-continued

| Ex. | Structural formula | m.p. (° C.) |
|---|---|---|
| 144 | | amorphous |

TABLE 34

| Ex. | Structural formula | m.p. (° C.) |
|---|---|---|
| 145 | | amorphous |
| 146 | | 228–230 |
| 147 | | amorphous |

TABLE 34-continued
| Ex. | Structural formula | m.p. (° C.) |
|---|---|---|
| 148 | 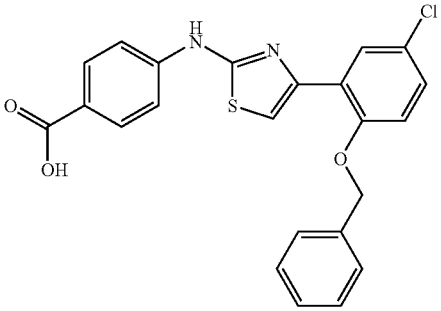 | 208–211 |
TABLE 35
| Ex. | Structural formula | m.p. (° C.) |
|---|---|---|
| 149 | 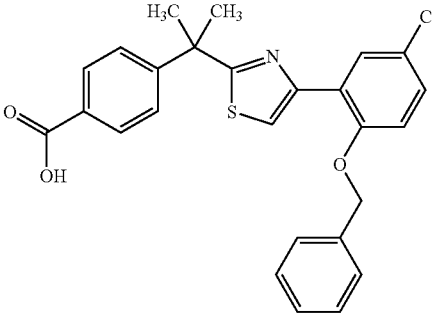 | 152–154 |
| 150 | 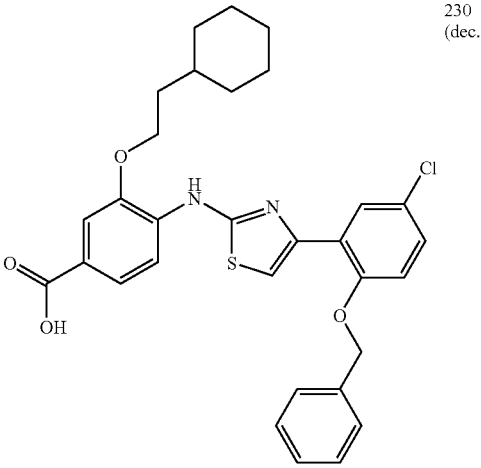 | 230 (dec.) |

TABLE 35-continued
| Ex. | Structural formula | m.p. (° C.) |
|---|---|---|
| 151 | 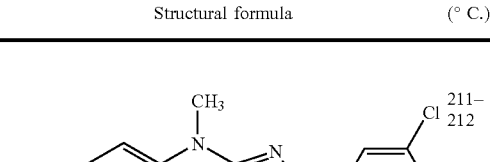 | 211–212 |
TABLE 36
| Ex. | Structural formula | m.p. (° C.) |
|---|---|---|
| 152 | 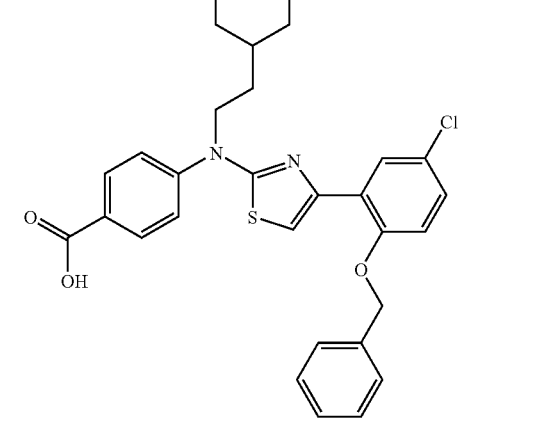 | 160–163 |
| 153 | 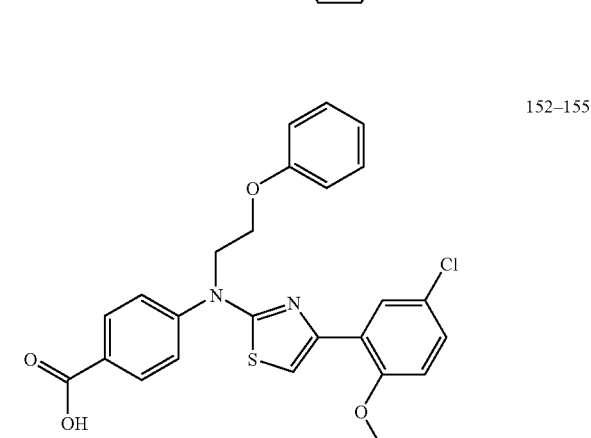 | 152–155 |

TABLE 36-continued

| Ex. | Structural formula | m.p. (° C.) |
|---|---|---|
| 154 | | 184–185 |

TABLE 37

| Ex. | Structural formula | m.p. (° C.) |
|---|---|---|
| 155 | | 218–219 |
| 156 | | 218–221 |

TABLE 37-continued

| Ex. | Structural formula | m.p. (° C.) |
|---|---|---|
| 157 | (structure) | 230–234 |

TABLE 38

| Ex. | Structural formula | m.p. (° C.) |
|---|---|---|
| 158 | (structure) | 212–213 |
| 159 | (structure) | 194–196 |

TABLE 38-continued

| Ex. | Structural formula | m.p. (° C.) |
|---|---|---|
| 160 | (structure) | 184–185 |

TABLE 39

| Ex. | Structural formula | m.p. (° C.) |
|---|---|---|
| 161 | (structure) | amorphous |
| 162 | (structure) | 210–211 |

TABLE 39-continued

| Ex. | Structural formula | m.p. (° C.) |
| --- | --- | --- |
| 163 | | 169–171 |

TABLE 40

| Ex. | Structural formula | m.p. (° C.) |
| --- | --- | --- |
| 164 | | 158–160 |
| 165 | | 171–172 |

TABLE 41
| Ex. | Structural formula | m.p. (° C.) |
|---|---|---|
| 166 | 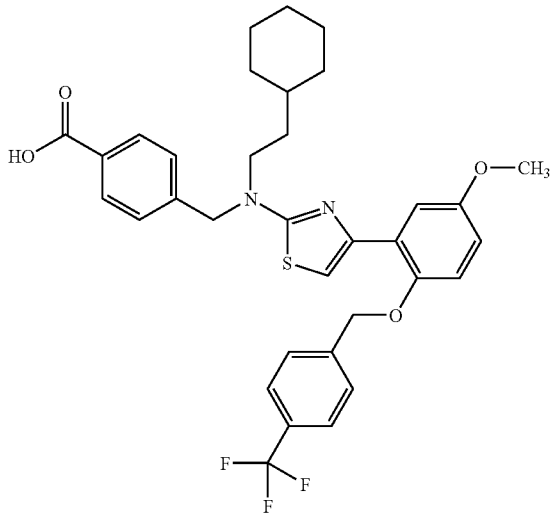 | 183–184 |
| 167 | 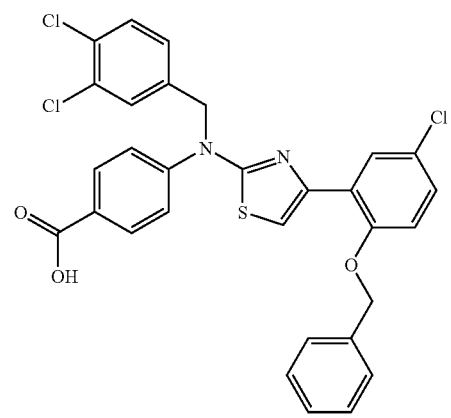 | 196–198 |
| 168 | 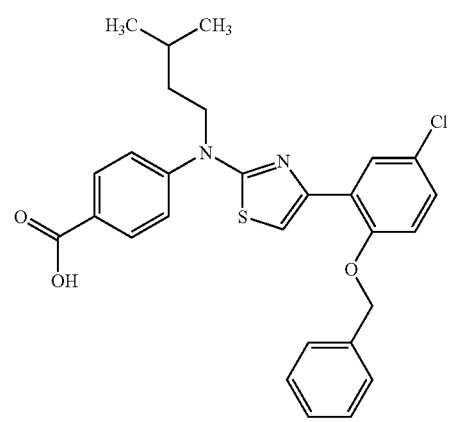 | 143–149 |

TABLE 42
| Ex. | Structural formula | m.p. (° C.) |
|---|---|---|
| 169 | 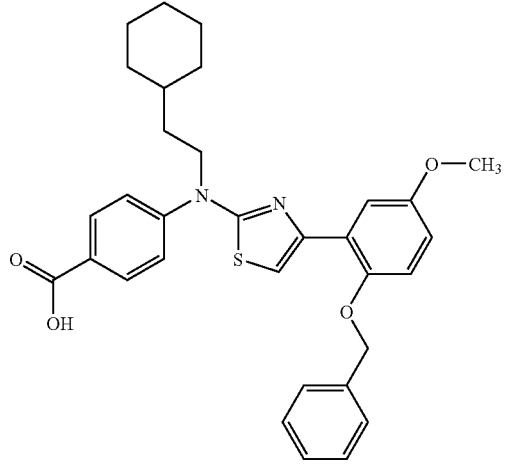 | 132–137 |
| 170 | 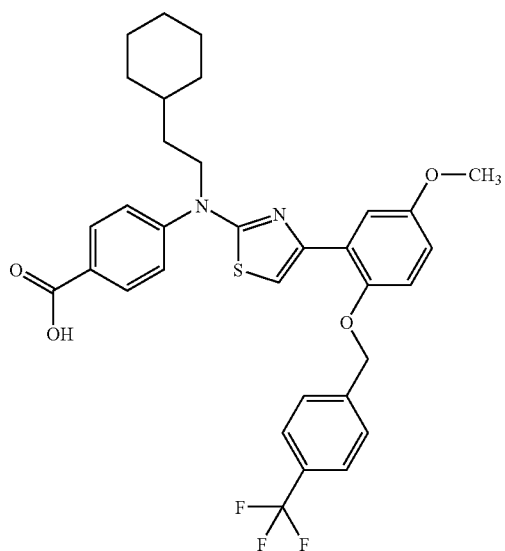 | 104–107 |

TABLE 43

| Ex. | Structural formula | m.p. (° C.) |
|---|---|---|
| 171 | | 111–114 |
| 172 | | 170–171 |
| 173 | | 215–218 |

TABLE 44
| Ex. | Structural formula | m.p. (° C.) |
|---|---|---|
| 174 | 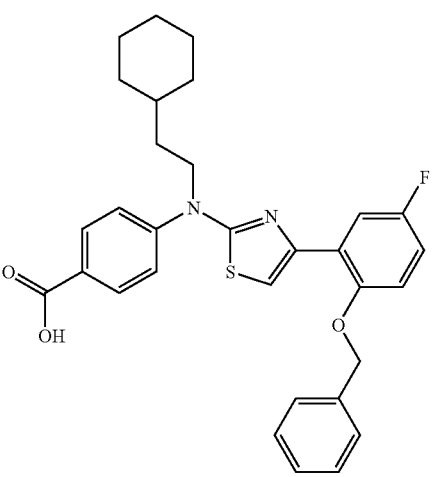 | 125–130 |
| 175 | 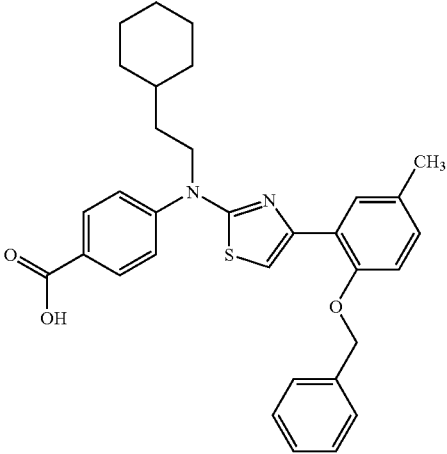 | 148–150 |
TABLE 45
| Ex. | Structural formula | m.p (° C.) |
|---|---|---|
| 176 | 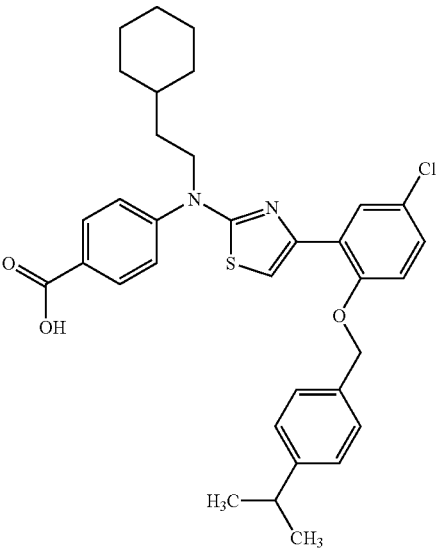 | 190–192 |
| 177 | 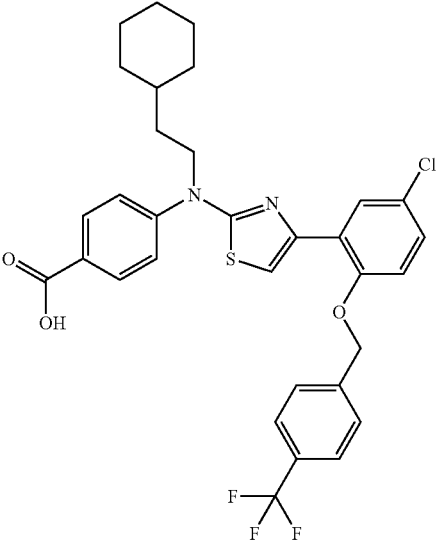 | 170–175 |

TABLE 46
| Ex. | Structural formula | m.p (° C.) |
|---|---|---|
| 178 | 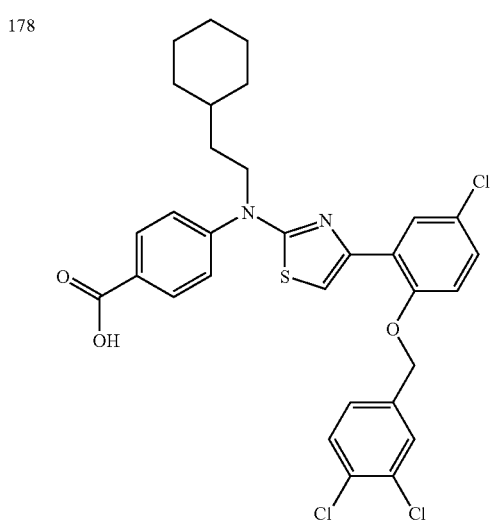 | 195–198 |
TABLE 46-continued
| Ex. | Structural formula | m.p (° C.) |
|---|---|---|
| 179 | 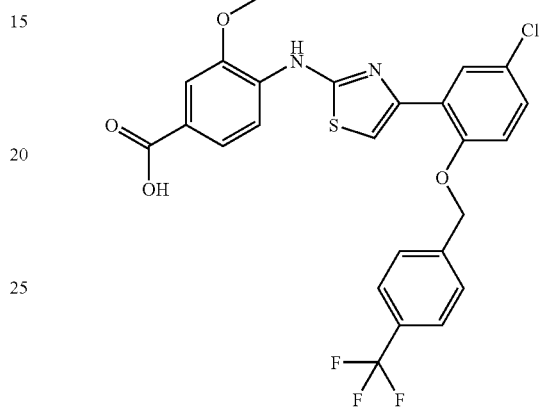 | 134–140 |
TABLE 47
| Ex. | Structural formula | m.p. (° C.) |
|---|---|---|
| 180 | 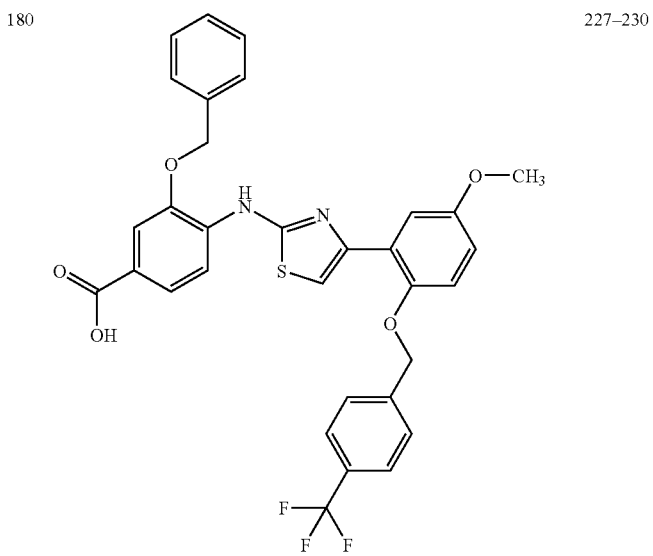 | 227–230 |

TABLE 47-continued
| Ex. | Structural formula | m.p. (° C.) |
|---|---|---|
| 181 | 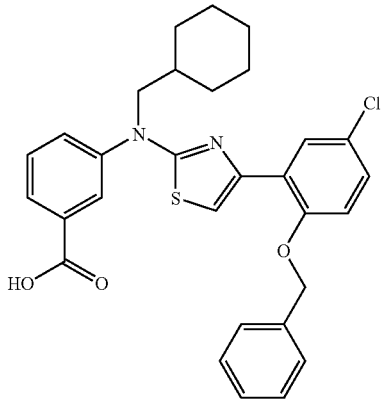 | 98–100 |
TABLE 48
| Ex. | Structural formula | m.p. (° C.) |
|---|---|---|
| 182 | 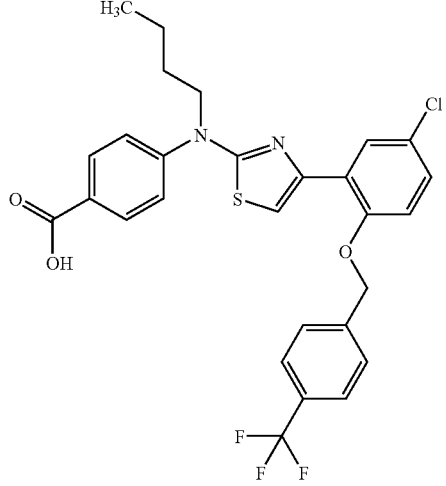 | 216–218 |
| 183 | 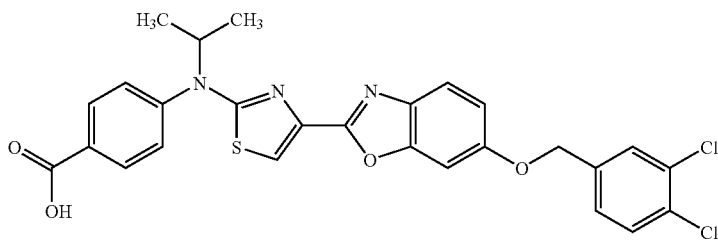 | 230 |
| 184 | 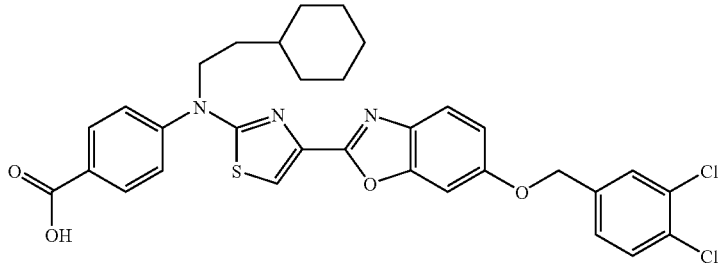 | 195–197 |

TABLE 48-continued
| Ex. | Structural formula | m.p. (° C.) |
|---|---|---|
| 185 | 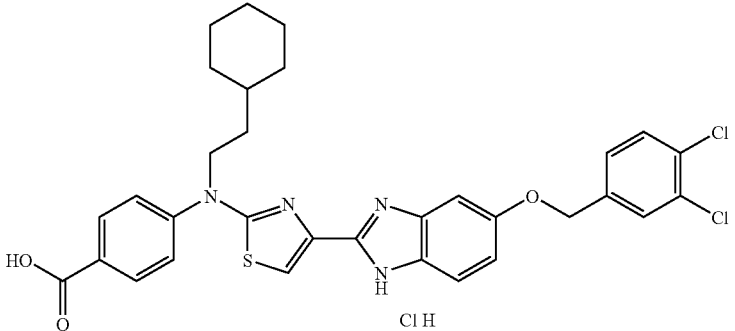 | 173–176 |
TABLE 49
| Ex. | Structural formula | m.p. (° C.) |
|---|---|---|
| 186 | 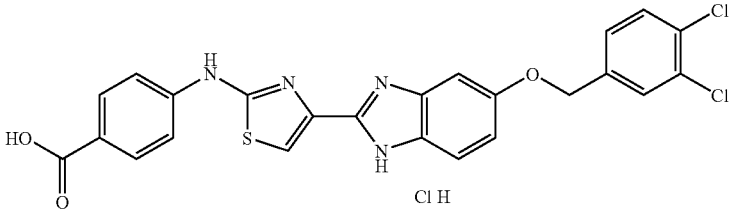 | 220 |
| 187 | 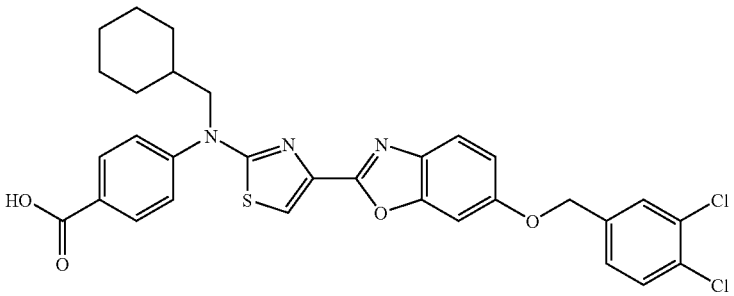 | 182–189 |
| 188 | 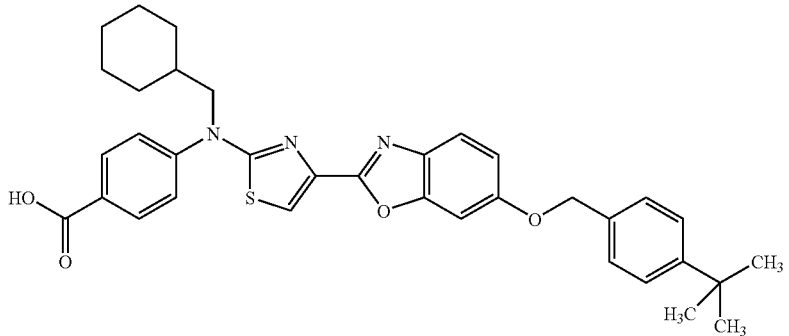 | 230 (dec.) |

TABLE 49-continued

| Ex. | Structural formula | m.p. (° C.) |
|---|---|---|
| 189 | | 213–214 |

TABLE 50

| Ex. | Structural formula | m.p. (° C.) |
|---|---|---|
| 190 | | 228–230 |
| 191 | | 160–162 |
| 192 | | amorphous |

TABLE 50-continued
| Ex. | Structural formula | m.p. (° C.) |
|---|---|---|
| 193 | 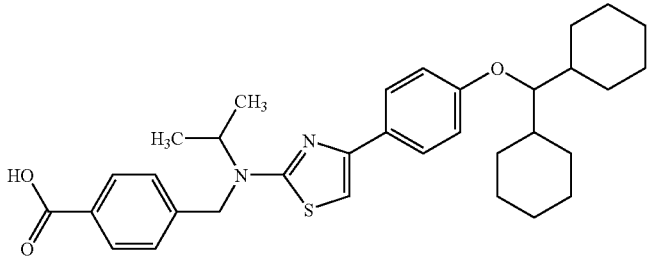 | amorphous |
TABLE 51
| Ex. | Structural formula | m.p. (° C.) |
|---|---|---|
| 194 | 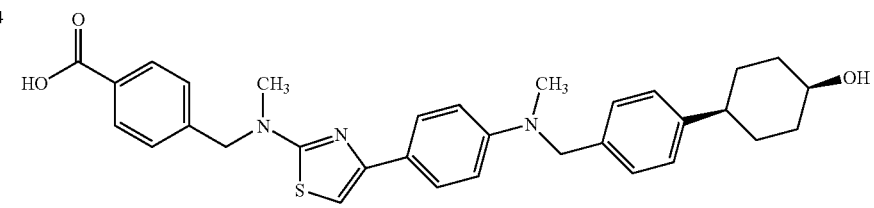 | 180–181 |
| 195 | 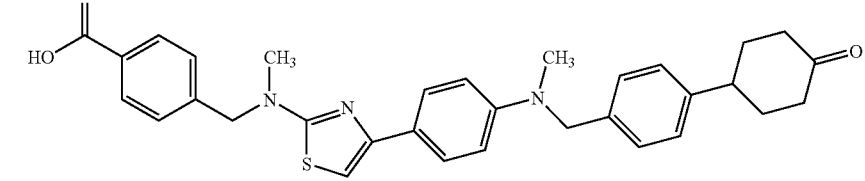 | amorphous |
| 196 | 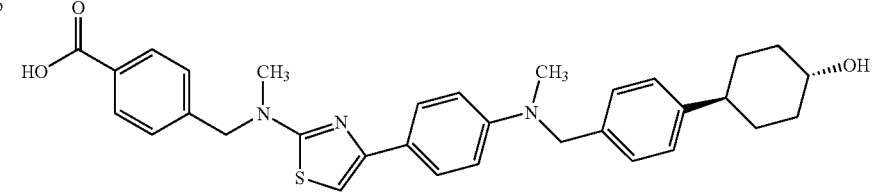 | 194–196 |
| 197 | 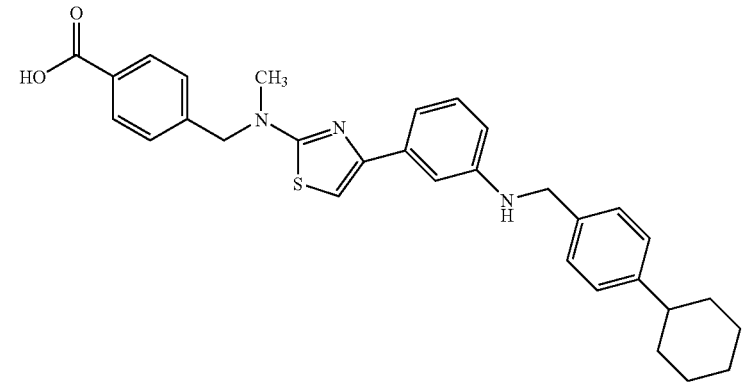 | amorphous |

TABLE 51-continued
| Ex. | Structural formula | m.p. (° C.) |
|---|---|---|
| 198 | 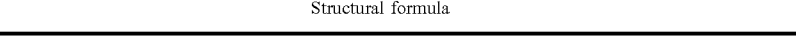 | amorphous |
TABLE 52
| Ex. | Structural formula | m.p. (° C.) |
|---|---|---|
| 199 | | amorphous |
| 200 | | amorphous |
| 201 | | amorphous |
| 202 | | amorphous |

TABLE 53

| Ex. | Structural formula | m.p. (° C.) |
|---|---|---|
| 203 | | amorphous |
| 204 | | 183 (dec.) |
| 205 | | 220 |
| 206 | | 159–161 |
| 207 | | 189–191 |
| 208 | | 210–213 |

TABLE 54

| Ex. | Structural formula | m.p. (° C.) |
|---|---|---|
| 209 | | 190–193 |

TABLE 54-continued
| Ex. | Structural formula | m.p. (° C.) |
|---|---|---|
| 210 | 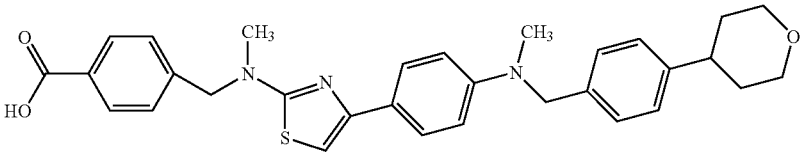 | 225–227 |
| 211 | 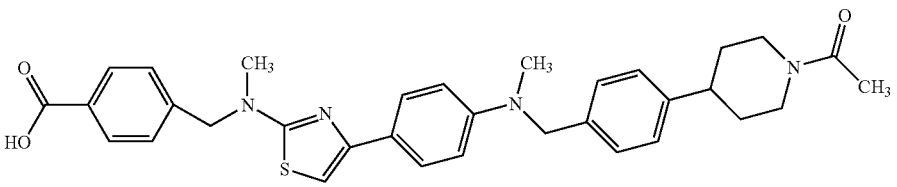 | 208–210 |
| 212 | 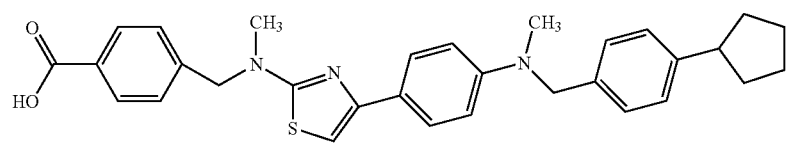 | 181–183 |
| 213 | 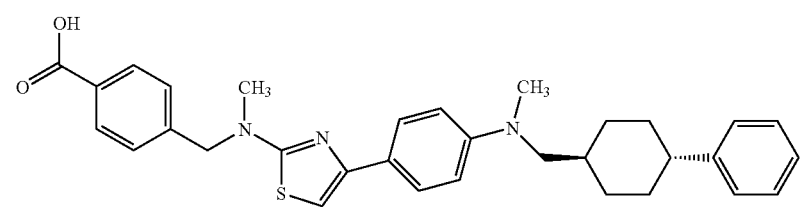 | 191–193 |
| 214 | 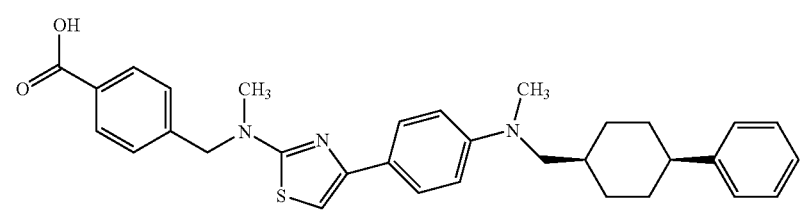 | amorphous |
TABLE 55
| Ex. | Structural formula | m.p. (° C.) |
|---|---|---|
| 215 | 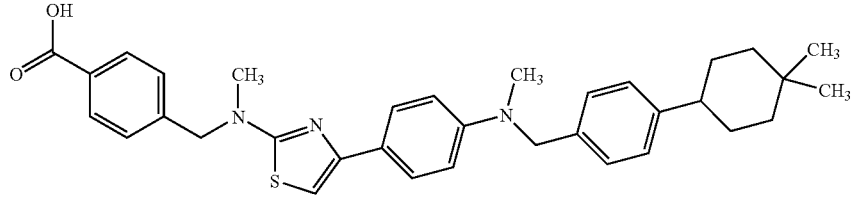 | 155–158 |
| 216 | 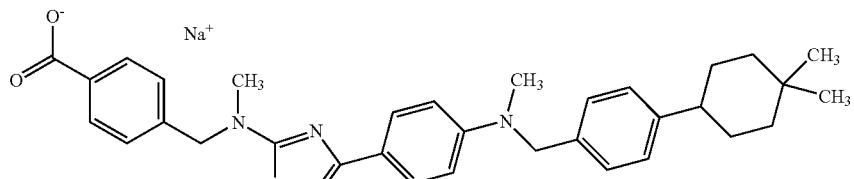 | 230 |

TABLE 55-continued

| Ex. | Structural formula | m.p. (° C.) |
|---|---|---|
| 217 | | 188–190 |
| 218 | | 185–191 |

TABLE 56

| Ex. | Structural formula | m.p. (° C.) |
|---|---|---|
| 219 | | amorphous |
| 220 | | 117–119 |
| 221 | | 105–108 |

TABLE 56-continued

| Ex. | Structural formula | m.p. (° C.) |
|---|---|---|
| 222 | | 146–147 |

TABLE 57

| Ex. | Structural formula | m.p. (° C.) |
|---|---|---|
| 223 | | 174–176 |
| 224 | | 151–152 |
| 225 | | 127–128 |
| 226 | | 157–159 |

TABLE 58

| Ex. | Structural formula | m.p. (° C.) |
|---|---|---|
| 227 | | 172–173 |
| 228 | | 155–157 |
| 229 | | 176–177 |
| 230 | | 114–115 |

TABLE 59

| Ex. | Structural formula | m.p. (° C.) |
|---|---|---|
| 231 | | 250 |

TABLE 59-continued

| Ex. | Structural formula | m.p. (° C.) |
|---|---|---|
| 232 | | 144–145 |
| 233 | | 166–167 |
| 234 | | 180–181 |
| 235 | | 162 |

TABLE 60

| Ex. | Structural formula | m.p. (° C.) |
|---|---|---|
| 236 | | 158–159 |

TABLE 60-continued
| Ex. | Structural formula | m.p. (° C.) |
|---|---|---|
| 237 | 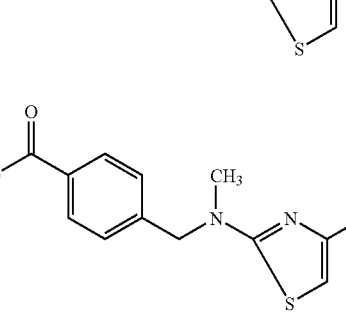 | 164–167 |
| 238 | 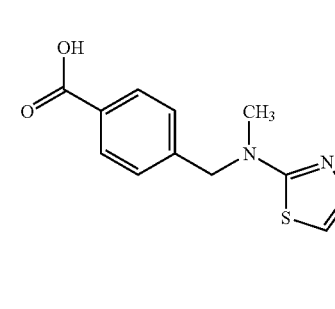 | 212–213 |
| 239 | 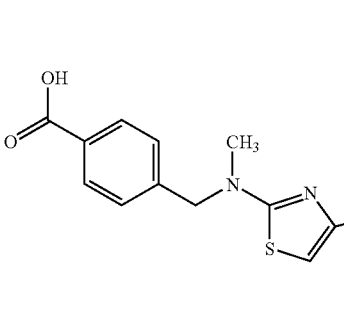 | 159–163 |
| 240 | 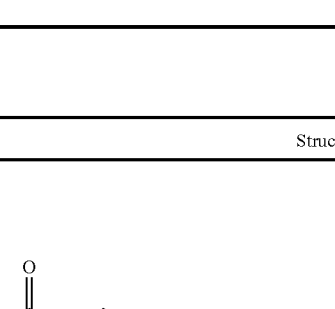 | 130–135 |
TABLE 61
| Ex. | Structural formula | m.p. (° C.) |
|---|---|---|
| 241 |  | 147–148 |

TABLE 61-continued

| Ex. | Structural formula | m.p. (° C.) |
|---|---|---|
| 242 | | 149–150 |
| 243 | | 122–127 |
| 244 | | 153–154 |

TABLE 62

| Ex. | Structural formula | m.p. (° C.) |
|---|---|---|
| 245 | | 132–134 |

TABLE 62-continued

| Ex. | Structural formula | m.p. (° C.) |
|---|---|---|
| 246 | | 205 (dec.) |
| 247 | | 209 (dec.) |
| 248 | | 104–105 |
| 249 | | 117–118 |

TABLE 63

| Ex. | Structural formula | m.p. (° C.) |
|---|---|---|
| 250 | | 116–117 |
| 251 | | 175 (dec.) |

TABLE 63-continued
| Ex. | Structural formula | m.p. (° C.) |
|---|---|---|
| 252 | 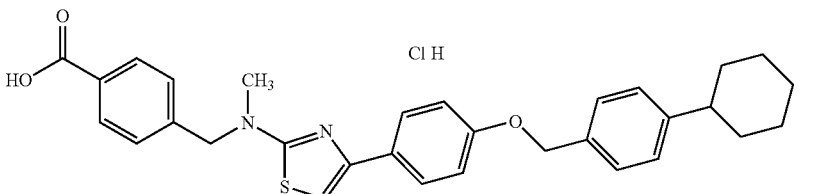 | 174 (dec.) |
| 253 |  | 240 |
| 254 | 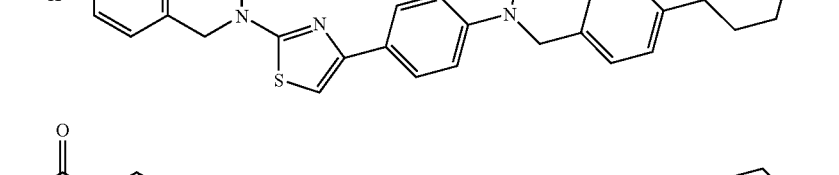 | amorphous |
TABLE 64
| Ex. | Structural formula | m.p. (° C.) |
|---|---|---|
| 255 | 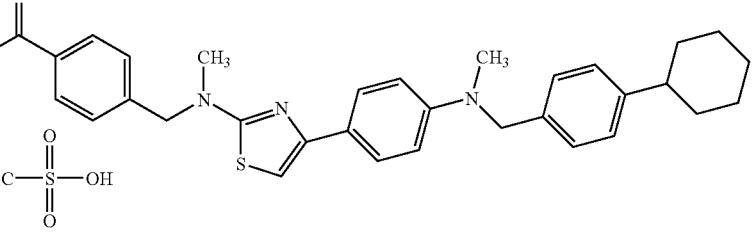 | 167–170 |
| 256 | 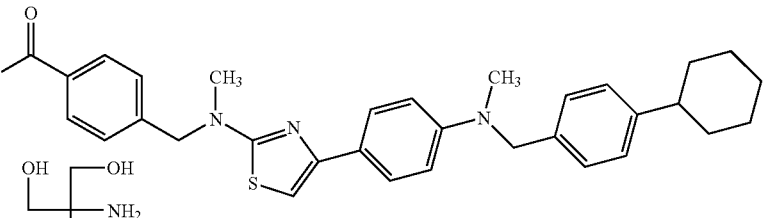 | 168–170 |
| 257 | 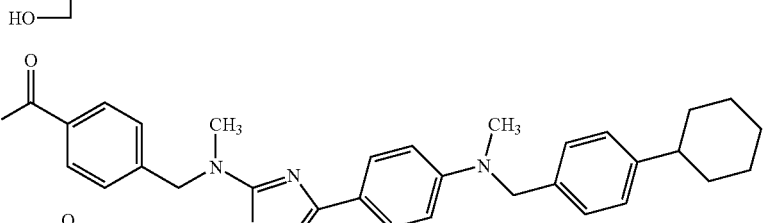 | 130 (dec.) |

TABLE 64-continued
| Ex. | Structural formula | m.p. (° C.) |
|---|---|---|
| 258 | 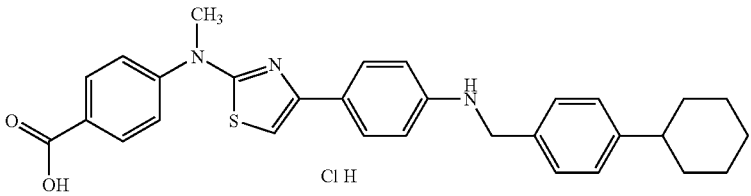 Cl H | 234–236 |
| 259 | 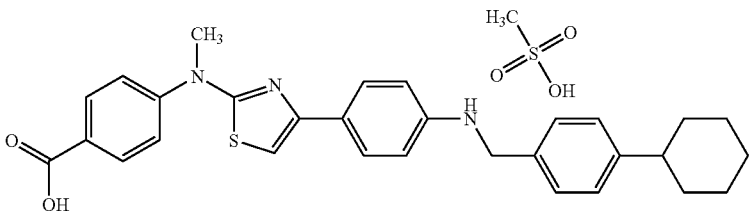 | 231–233 |
TABLE 65
| Ex. | Structural formula | m.p. (° C.) |
|---|---|---|
| 260 | 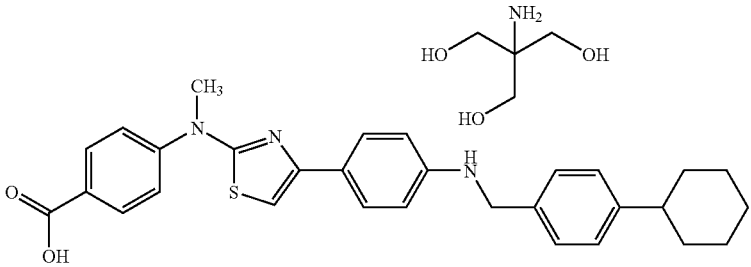 | 220–223 |
| 261 | 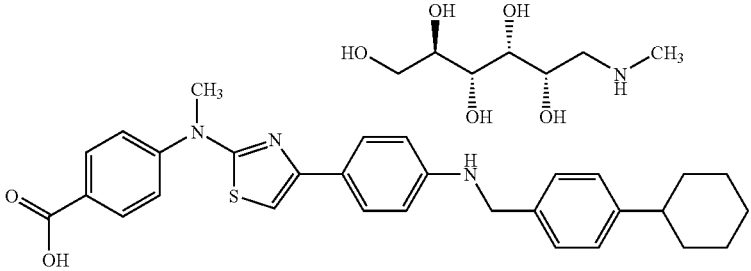 | 159 (dec.) |
| 262 | 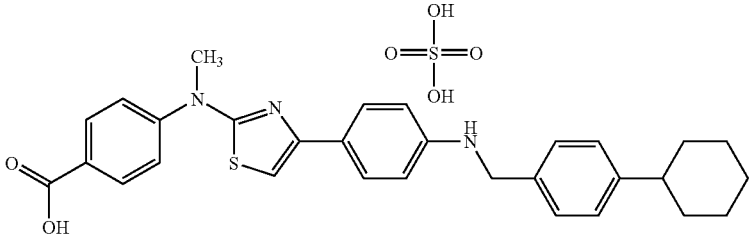 | 239 (dec.) |

TABLE 65-continued
| Ex. | Structural formula | m.p. (° C.) |
|---|---|---|
| 263 | 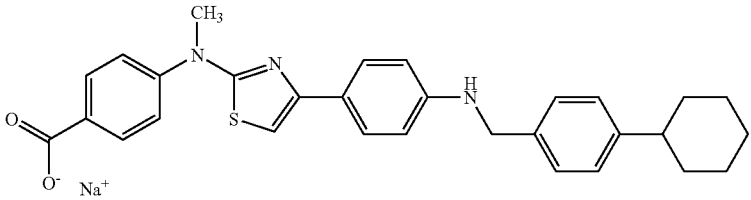 | 260 |
| 264 | 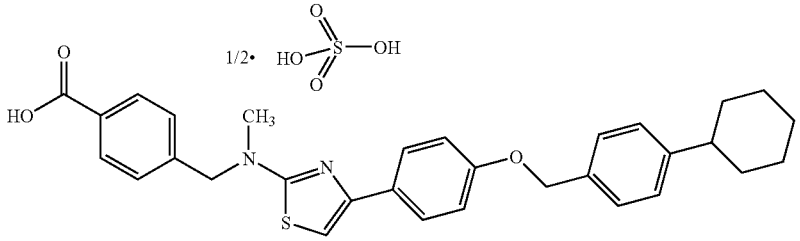 | 182–183 |
TABLE 66
| Ex. | Structural formula | m.p. (° C.) |
|---|---|---|
| 265 | 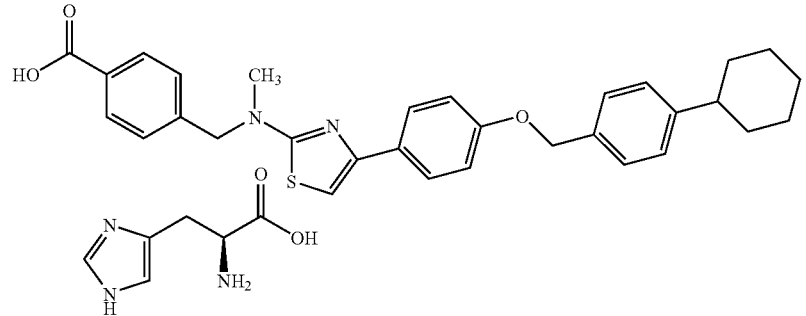 | 208–221 |
| 266 | 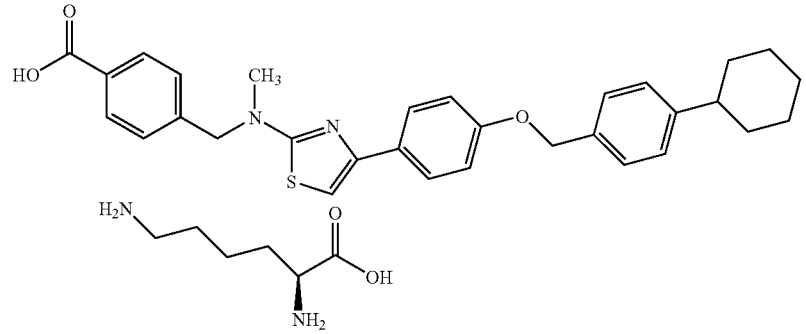 | 200–202 |
| 267 | 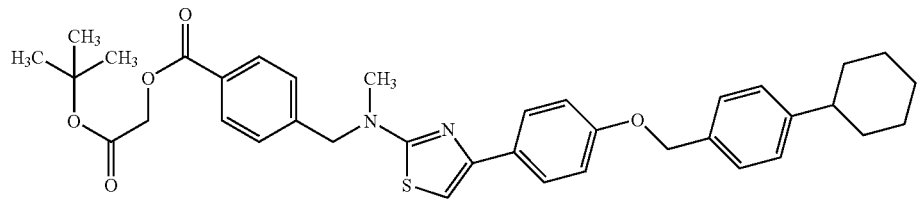 | 122–123 |

TABLE 66-continued

| Ex. | Structural formula | m.p. (° C.) |
|---|---|---|
| 268 | | 88–90 |
| 269 | | 99–101 |

TABLE 67

| Ex. | Structural formula | m.p. (° C.) |
|---|---|---|
| 270 | | 100–104 |
| 271 | | 76–84 |
| 272 | | 75–79 |

TABLE 67-continued

| Ex. | Structural formula | m.p. (° C.) |
|---|---|---|
| 273 | | 87–92 |
| 274 | | 230 (dec.) |

A Formulation Example is shown in the following, which is not to be construed as limitative.

FORMULATION EXAMPLE

| | |
|---|---|
| (a) Compound of Example 1 | 10 g |
| (b) Lactose | 50 g |
| (c) Corn starch | 15 g |
| (d) Sodium carboxymethyl cellulose | 44 g |
| (e) Magnesium stearate | 1 g |

The total amount of (a), (b) and (c) and 30 g of (d) were kneaded with water, dried in vacuo and granulated. The granulated powder was mixed with 14 g of (d) and 1 g of (e) and the mixture was punched with a tableting machine to give 1000 tablets containing 10 mg of (a) per tablet.

The test results of the protein tyrosine phosphatase 1B inhibitory action of the present invention are shown in the following.

EXPERIMENTAL EXAMPLE

Experimental Example 1

Protein Tyrosine Phosphatase 1B Inhibitory Action

Preparation of Assay Buffer:
50 mM Tris-HCl buffer (pH 7.5), and 50 mM NaCl and 3 mM dithiothreitol (DTT) were prepared.

Preparation of Sample:
Respective 10 mM DMSO solutions of 0.1, 0.3, 1, 3 and 10 μM test compounds were diluted with the above-mentioned assay buffer so that the final dimethyl sulfoxide (DMSO) concentration would be not more than 1%. As a control, an assay buffer was used.

Preparation of Substrate:
A synthetic peptide consisting of 12 amino acids corresponding to 1142nd–1153rd of insulin receptor sequence, wherein three tyrosines therein had been phosphorylated, was diluted with the above-mentioned assay buffer to 80 μM.

Preparation of Enzyme:
A recombinant human protein tyrosine phosphatase 1B (manufactured by UBI) was diluted with the above-mentioned assay buffer (1.2 ng/25 μl).

(Evaluation Method)
A sample (10 μl) and a substrate (25 μl) prepared as mentioned above were successively added to a 96 well plate, and an enzyme (25 μl) prepared as mentioned above was added and mixed. After incubation at room temperature for 60 min., malachite green (120 μl, Biomol), which is a phosphorus color fixing agent, was added, and the mixture was further incubated at room temperature for 20 min. to allow color development. The absorbance at 650 nm was measured on a plate reader, and the protein tyrosine phosphatase 1B inhibitory action of the test compound was evaluated. The results are shown in Table 68.

Experimental Example 2

Hypoglycemic Action

A 0.5% methyl cellulose suspension of the test compound was orally administered to male ob/ob mice (6 to 9 weeks old) grouped based on blood glucose level. A 0.5% methyl cellulose solution alone was administered to a control group.

The blood was drawn from the orbital vein with anesthesia at 3 hours after the administration. The blood was drawn under fasting by removing the feed immediately before test compound administration. The blood thus drawn was separated by centrifugation and the blood glucose level was measured from the obtained plasma according to the hexokinase method (glucose measure kit). For evaluation, decrease in the blood glucose level of the test compound administration group relative to the control group was shown in percentage. The results are shown in Table 68.

TABLE 68

| Example | PTP1B inhibitory action (IC$_{50}$:μM) | Decrease in blood glucose level (%) | |
|---|---|---|---|
| | | Dose (mg/kg) | 3 hr |
| 1 | 0.32 | 0.3 | 35 |
| | | 1 | 35 |
| | | 3 | 35 |
| 2 | 0.22 | 1 | 37 |
| | | 3 | 47 |
| 3 | 0.50 | 1 | 27 |
| | | 3 | 35 |
| 115 | 0.48 | 3 | 34 |
| 196 | 0.83 | 3 | −8 |
| 208 | 0.11 | 3 | 21 |
| 209 | 0.49 | 3 | 20 |
| 215 | 0.11 | 0.3 | −9 |
| | | 1 | 32 |
| | | 3 | 39 |
| 217 | 0.26 | 3 | 20 |
| 218 | 0.15 | 3 | 27 |
| 230 | 0.15 | 3 | 40 |

Experimental Example 3

Blood Lipid Lowering Action

A 0.5% methyl cellulose suspension of the test compound was orally administered to 7-week-old db/db mice once a day for 14 days. The 0.5% methyl cellulose solution alone was administered to the control group.

The blood was drawn from the orbital vein with light ether anesthesia before test compound administration on day 7 day 14 under non-fasting condition. The blood thus drawn was separated by centrifugation and the plasma triglyceride concentration was measured from the obtained plasma according to the enzyme method (triglyceride measure kit). The results are shown in Table 69.

TABLE 69

| | Dose (mg/kg) | Plasma triglyceride concentration (mg/dL) | |
|---|---|---|---|
| | | Day 7 | Day 14 |
| Control group | — | 508 | 622 |
| test compound administration group (Example 102) | 10 | 277 | 349 |
| | 30 | 250 | 307 |

INDUSTRIAL APPLICABILITY

From the foregoing test results and the like, the compound [I] of the present invention is suggested have a superior PTP1B inhibitory action. That is, the compound [I] of the present invention is expected to be a new type of drug for the prophylaxis or treatment of diabetes that can directly improve the insulin action, insulin sensitivity, insulin resistance and/or glucose resistance. In addition, the compound [I] of the present invention is also expected as a drug for the prophylaxis or treatment of diabetic complications (retinopathy, nephropathy, neuropathy, cardiac infarction and cerebral infarction based on arteriosclerosis etc.), and further as a treatment drug of a disease mediated by PTP1B. Moreover, because compound [I] of the present invention has been confirmed to show a blood lipid lowering action from the above test results, it is also expected as a drug for the prophylaxis or treatment of hyperlipidemia.

This application is based on a patent application No. 368567/2001 filed in Japan, the contents of which are hereby incorporated by reference.

The invention claimed is:

1. An azole compound represented by the formula [I]

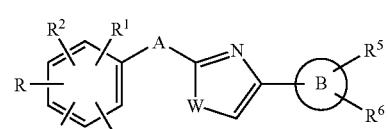

[I]

wherein
W is a sulfur atom or an oxygen atom;
R is
(1) —COOR$^7$ wherein R$^7$ is a hydrogen atom or a lower alkyl group),
(2) —X$^1$-A$^1$-COOR$^7$
wherein
X$^1$ is —O—, —N(R$^{15}$)— or —S(O)$_p$— wherein R$^{15}$ is a hydrogen atom or a lower alkyl group, p is 0, 1 or 2,
A$^1$ is a lower alkylene group, and
R$^7$ is a hydrogen atom or a lower alkyl group, or
(3) a tetrazolyl group;
R$^1$, R$^2$, R$^3$ and R$^4$ are each independently
(1) a hydrogen atom,
(2) a halogen atom,
(3) a hydroxyl group,
(4) an optionally substituted lower cycloalkylalkyloxy group,
(5) an optionally substituted aralkyloxy group,
(6) a cyano group,
(7) a nitro group,
(8) a lower alkyl group,
(9) a lower haloalkyl group,
(10) a lower alkoxy group or
(11) a lower haloalkoxy group;
A is a group represented by —(CH$_2$)$_m$—X—
wherein
X is —N(R$^8$)—, —C(R$^9$)(R$^{10}$)—, —CO— or —CO—N(R$^8$)—
wherein
R$^8$ is a hydrogen atom, —SO$_2$R$^{16}$ (R$^{16}$ is a lower alkyl group or an aryl group) or a lower alkyl group, wherein said lower alkyl group is optionally substituted by a substituent selected from the group consisting of a lower alkoxy group, an aryloxy group, —N(R$^{11}$)(R$^{12}$) (R$^{11}$ and R$^{12}$ are each independently a hydrogen atom or a lower alkyl group or may form, together with a nitrogen atom bonded thereto, a 5- to 7-membered hetero ring optionally further having at least one hetero atom selected from the group consisting of nitrogen atom, oxygen atom and sulfur atom), a carboxy group, a lower cycloalkyl group and an optionally substituted aryl group, and
R$^9$ and R$^{10}$ are each independently a hydrogen atom or a lower alkyl group or may form lower cycloalkane together with a carbon atom bonded thereto, or may form, together with a carbon atom bonded thereto, a 5- to 7-membered hetero ring optionally further having at least one hetero atom selected from the group consisting of nitrogen atom, oxygen atom and sulfur atom, and m is 0 or an integer of 1 to 3;
B is an aryl group or an aromatic heterocyclic group;
$R^5$ is
(1) a hydrogen atom,
(2) a halogen atom,
(3) a lower alkyl group,
(4) a lower alkoxy group,
(5) a cyano group,
(6) a nitro group,
(7) a lower haloalkyl group or
(8) —S(O)$_r$—R$^{17}$ (R$^{17}$ is a lower alkyl group or an aryl group and r is 0, 1 or 2); and
$R^6$ is —(Y)$_{s1}$-(A$^2$)$_s$-Z
wherein
s1 and s are each independently 0 or 1,
Y is —O—, —S(O)$_t$—, —N(R$^{13}$)—, —N(R$^{14}$)—CO—, —N(R$^{14}$)—SO$_2$—, —SO$_2$—N(R$^{14}$))—, —C(R$^{18}$)(R$^{19}$)— or —CO—
(wherein
t is 0, 1 or 2,
R$^{13}$ is
(1) a hydrogen atom,
(2) a lower alkyl group
(wherein said lower alkyl group optionally substituted by a substituent selected from the group consisting of
(a) a lower cycloalkyl group,
(b) an optionally substituted aryl group,
(c) an optionally substituted heterocyclic group and
(d) a hydroxyl group),
(3) a lower alkenyl group,
(4) a lower alkylsulfonyl group or
(5) a lower alkylcarbonyl group
(wherein said lower alkylcarbonyl group is optionally substituted by a hydroxyl group or a lower alkoxy group),
R$^{14}$ is a hydrogen atom or a lower alkyl group, and
R$^{18}$ and R$^{19}$ are each independently a hydrogen atom or a lower alkyl group or may form lower cycloalkane together with a carbon atom bonded thereto, or may form, together with a carbon atom bonded thereto, a 5- to 7-membered hetero ring optionally further having at least one hetero atom selected from the group consisting of nitrogen atom, oxygen atom and sulfur atom),
A$^2$ is a lower alkylene group optionally substituted by a lower cycloalkyl group, and
Z is
(1) a lower cycloalkyl group
(wherein said a lower cycloalkyl group is optionally substituted by an optionally substituted phenyl group),
(2) an aryl group
(wherein said aryl group is optionally substituted by a substituent selected from the group consisting of
(a) a heterocyclic group optionally substituted by a substituent selected from the group consisting of a lower alkyl group and a lower alkylcarbonyl group,
(b) a lower cycloalkyl group optionally substituted by a substituent selected from the group consisting of a hydroxyl group, an oxo group, a halogen atom and a lower alkyl group,
(c) a carboxy group,
(d) a halogen atom,
(e) an alkyl group,
(f) a lower haloalkyl group,
(g) a lower alkylamino group,
(h) a di(lower alkyl)amino group,
(i) a lower alkylthio group and
(j) a lower alkoxy group),
(3) an optionally substituted aromatic heterocyclic group,
(4) an indanyl group or
(5) a piperazinyl group
(wherein said piperazinyl group is optionally substituted by a substituent selected from the group consisting of
(a) a phenyl group,
(b) a phenyl lower alkyl group,
(c) a benzoyl group optionally substituted by a halogen atom and
(d) a phenyl lower alkoxycarbonyl group),
a prodrug thereof or a pharmaceutically acceptable salt thereof.

2. The azole compound of claim 1, wherein, in the formula [I],
W is a sulfur atom or an oxygen atom;
R is
(1) —COOR$^7$ wherein R$^7$ is a hydrogen atom or a C$_{1-4}$ alkyl group,
(2) —X$^1$-A$^1$-COOR$^7$
wherein
X$^1$ is —O—, —N(R$^{15}$)— or —S(O)$_p$— wherein R$^{15}$ is a hydrogen atom or a C$_{1-4}$ alkyl group and p is 0, 1 or 2,
A$^1$ is a C$_{1-4}$ alkylene group,
R$^7$ is a hydrogen atom or a C$_{1-4}$ alkyl group or
(3) a tetrazolyl group,
R$^1$, R$^2$, R$^3$ and R$^4$ are each independently,
(1) a hydrogen atom,
(2) a halogen atom,
(3) a hydroxyl group,
(4) an optionally substituted C$_{3-7}$cycloalkyl C$_{1-4}$ alkyloxy group,
(5) an optionally substituted aralkyloxy group,
(6) a cyano group,
(7) a nitro group,
(8) a C$_{1-4}$ alkyl group,
(9) a C$_{1-4}$ haloalkyl group,
(10) a C$_{1-4}$ alkoxy group or
(11) a C$_{1-4}$ haloalkoxy group;
A is a group represented by —(CH$_2$)$_m$—X—
wherein
X is —N(R$^8$)—, —C(R$^9$)(R$^{10}$)—, —CO— or —CO—N(R$^8$)—
wherein
R$^8$ is a hydrogen atom, —SO$_2$R$^{16}$ (R$^{16}$ is a C$_{1-6}$ alkyl group or an aryl group) or a C$_{1-6}$ alkyl group, wherein said C$_{1-6}$ alkyl group is optionally substituted by a substituent selected from the group consisting of a C$_{1-4}$ alkoxy group, an aryloxy group, —N(R$^{11}$)(R$^{12}$) (R$^{11}$ and R$^{12}$ are each independently a hydrogen atom or a C$_{1-4}$ alkyl group or may form, together with a nitrogen atom bonded thereto, a 5- to 7-membered hetero ring optionally further having at least one hetero atom selected from the group consisting of nitrogen atom, oxygen atom and sulfur atom), a carboxy group, C$_{3-7}$cycloalkyl group and an optionally substituted aryl group,
R$^9$ and R$^{10}$ are each independently a hydrogen atom or a C$_{1-4}$ alkyl group, or may form a C$_{3-7}$ cycloalkane together with a carbon atom bonded thereto, or may form, together with a carbon atom bonded thereto, a 5- to 7-membered hetero ring optionally further having at least one hetero atom selected from the group consisting of nitrogen atom, oxygen atom and sulfur atom,
m is 0 or an integer of 1 to 3;
B is an aryl group or an aromatic heterocyclic group;
R$^5$ is
(1) a hydrogen atom,
(2) a halogen atom, (3) a $C_{1-4}$ alkyl group,
(4) a $C_{1-4}$ alkoxy group,
(5) a cyano group,
(6) a nitro group,
(7) a $C_{1-4}$ haloalkyl group or
(8) —S(O)$_r$—R$^{17}$ (R$^{17}$ is a $C_{1-6}$ alkyl group or an aryl group and r is 0, 1 or 2);
R$^6$ is —(Y)$_{s1}$-(A$^2$)$_s$-Z
wherein
s1 and s are each independently 0 or 1,
Y is —O—, —S(O)$_t$—, —N(R$^{13}$)—, —N(R$^{14}$)—CO—, —N(R$^{14}$)—SO$_2$—, —SO$_2$—N(R$^{14}$))—, —C(R$^{18}$)(R$^{19}$)— or —CO—
(wherein
t is 0, 1 or 2,
R$^{13}$ is
(1) a hydrogen atom,
(2) a C-4 alkyl group
(wherein said $C_{1-4}$ alkyl group is optionally substituted by a substituent selected from the group consisting of
  (a) a $C_{3-7}$ cycloalkyl group,
  (b) an optionally substituted aryl group,
  (c) an optionally substituted heterocyclic group and
  (d) a hydroxyl group),
(3) a $C_{2-4}$ alkenyl group,
(4) a $C_{1-4}$ alkylsulfonyl group or
(5) a $C_{1-4}$ alkylcarbonyl group
(wherein said $C_{1-4}$ alkylcarbonyl group is optionally substituted by a hydroxyl group or a $C_{1-4}$ alkoxy group),
R$^{14}$ is a hydrogen atom or a $C_{1-4}$ alkyl group,
R$^{18}$ and R$^{19}$ are each independently a hydrogen atom or a $C_{1-4}$ alkyl group, or may form $C_{3-7}$ cycloalkane together with a carbon atom bonded thereto, or may form, together with a carbon atom bonded thereto, a 5- to 7-membered hetero ring optionally further having at least one hetero atom selected from the group consisting of nitrogen atom, oxygen atom and sulfur atom),
A$^2$ is a $C_{1-4}$ alkylene group optionally substituted by a $C_{3-7}$ cycloalkyl group,
Z is
(1) a $C_{3-7}$cycloalkyl group
(wherein said $C_{3-7}$ cycloalkyl group is optionally substituted by a phenyl group optionally substituted by a halogen atom),
(2) an aryl group
(wherein said aryl group is optionally substituted by a substituent selected from the group consisting of
  (a) a heterocyclic group optionally substituted by a substituent selected from the group consisting of a $C_{1-4}$ alkyl group and a $C_{1-4}$ alkylcarbonyl group,
  (b) a $C_{3-7}$ cycloalkyl group optionally substituted by a substituent selected from the group consisting of a hydroxyl group, an oxo group, a halogen atom and a $C_{1-4}$ alkyl group,
  (c) a carboxy group,
  (d) a halogen atom,
  (e) a $C_{1-8}$ alkyl group,
  (f) a $C_{1-4}$ haloalkyl group,
  (g) a $C_{1-4}$ alkylamino group,
  (h) a di($C_{1-4}$ alkyl)amino group,
  (i) a $C_{1-4}$ alkylthio group and
  (j) a $C_{1-4}$ alkoxy group),
(3) an aromatic heterocyclic group
(wherein said aromatic heterocyclic group is optionally substituted by a substituent selected from the group consisting of
  (a) a heterocyclic group optionally substituted by a $C_{1-4}$ alkyl group,
  (b) a $C_{1-6}$ alkyl group,
  (c) an aryl group optionally substituted by a halogen atom or a $C_{1-4}$ haloalkyl group,
  (d) a halogen atom,
  (e) a $C_{1-4}$ haloalkyl group,
  (f) a carboxy group,
  (g) a $C_{3-7}$ cycloalkyl group and
  (h) a $C_{1-4}$ alkoxy group),
(4) an indanyl group or
(5) a piperazinyl group
(wherein said piperazinyl group is optionally substituted by a substituent selected from the group consisting of
  (a) a phenyl group,
  (b) a phenyl $C_{1-4}$ alkyl group,
  (c) a benzoyl group optionally substituted by a halogen atom and
  (d) a phenyl $C_{1-4}$ alkoxycarbonyl group),
a prodrug thereof or a pharmaceutically acceptable salt thereof.

3. The azole compound of claim 2, wherein W is a sulfur atom or an oxygen atom,
R is
(1) —COOR$^7$ wherein R$^7$ is a hydrogen atom,
(2) —X$^1$-A$^1$-COOR$^7$
wherein
X$^1$ is —O—,
A$^1$ is a $C_{1-4}$ alkylene group,
R$^7$ is a hydrogen atom or
(3) a tetrazolyl group;
R$^1$, R$^2$, R$^3$ and R$^4$ are each independently
(1) a hydrogen atom,
(2) a halogen atom,
(3) a hydroxyl group,
(4) an optionally substituted $C_{3-7}$ cycloalkyl $C_{1-4}$ alkyloxy group or
(5) an optionally substituted aralkyloxy group;
A is a group represented by —(CH$_2$)$_m$—X—
wherein
X is —N(R$^8$)—, —C(R$^9$)(R$^{10}$)— or —CO—
wherein
R$^8$ is a hydrogen atom or a $C_{1-6}$ alkyl group, wherein said $C_{1-6}$ alkyl group is optionally substituted by a substituent selected from the group consisting of a $C_{1-4}$ alkoxy group, an aryloxy group, —N(R$^{11}$)(R$^{12}$) (R$^{11}$ and R$^{12}$ are each independently a hydrogen atom or a $C_{1-4}$ alkyl group or may form, together with a nitrogen atom bonded thereto, a 5- to 7-membered hetero ring optionally further having at least one hetero atom selected from the group consisting of nitrogen atom, oxygen atom and sulfur atom), a carboxy group, a $C_{3-7}$ cycloalkyl group and an optionally substituted aryl group,
R$^9$ and R$^{10}$ are each independently a hydrogen atom or a $C_{1-4}$ alkyl group, or may form $C_{3-7}$ cycloalkane together with a carbon atom bonded thereto, or may form, together with a carbon atom bonded thereto, a 5- to 7-membered hetero ring optionally further having at least one hetero atom selected from the group consisting of nitrogen atom, oxygen atom and sulfur atom,
m is 0 or an integer of 1 to 3;
B is an aryl group or an aromatic heterocyclic group;
R$^5$ is
(1) a hydrogen atom,
(2) a halogen atom,
(3) a $C_{1-4}$ alkyl group or
(4) a $C_{1-4}$ alkoxy group;
R$^6$ is —(Y)$_{s1}$-(A$^2$)$_s$-Z wherein
  s1 and s are each independently 0 or 1,
  Y is —O—, —S(O)$_t$—, —N(R$^{13}$)—, —N(R$^{14}$)—CO— or —N(R$^{14}$)—SO$_2$—
wherein
  t is 0, 1 or 2,
  R$^{13}$ is
    (1) a hydrogen atom,
    (2) a C-4 alkyl group
(wherein said C$_{1-4}$ alkyl group is optionally substituted by a substituent selected from the group consisting of
    (a) a C$_{3-7}$cycloalkyl group,
    (b) an optionally substituted aryl group,
    (c) an optionally substituted heterocyclic group and
    (d) a hydroxyl group),
    (3) a C$_{2-4}$ alkenyl group,
    (4) a C$_{1-4}$ alkylsulfonyl group or
    (5) a C$_{1-4}$ alkylcarbonyl group
(wherein said C$_{1-4}$ alkylcarbonyl group is optionally substituted by a hydroxyl group or a C$_{1-4}$ alkoxy group),
  R$^{14}$ is a hydrogen atom or a C$_{1-4}$ alkyl group,
  A$^2$ is a C$_{1-4}$ alkylene group optionally substituted by a C$_{3-7}$ cycloalkyl group,
  Z is
    (1) a C$_{3-7}$ cycloalkyl group
(wherein said C$_{3-7}$ cycloalkyl group is optionally substituted by a phenyl group),
    (2) an aryl group
(wherein said aryl group is optionally substituted by a substituent selected from the group consisting of
    (a) a heterocyclic group optionally substituted by a C$_{1-4}$ alkyl group or a C$_{1-4}$ alkylcarbonyl group,
    (b) a C$_{3-7}$ cycloalkyl group optionally substituted by a substituent selected from the group consisting of a hydroxyl group, an oxo group, a halogen atom and a C$_{1-4}$ alkyl group,
    (c) a carboxy group,
    (d) a halogen atom,
    (e) a C$_{1-8}$ alkyl group,
    (f) a C$_{1-4}$ haloalkyl group,
    (g) a C$_{1-4}$ alkylamino group and
    (h) a di(C$_{1-4}$ alkyl)amino group,
    (i) a C$_{1-4}$ alkylthio group and
    (j) a C$_{1-4}$ alkoxy group),
    (3) an aromatic heterocyclic group
(wherein said aromatic heterocyclic group is optionally substituted by a substituent selected from the group consisting of
    (a) a heterocyclic group,
    (b) a C$_{1-4}$ alkyl group and
    (c) a phenyl group optionally substituted by a halogen atom or a C$_{1-4}$ haloalkyl group),
    (4) an indanyl group or
    (5) a piperazinyl group
(wherein said piperazinyl group is optionally substituted by a substituent selected from the group consisting of
    (a) a phenyl group,
    (b) a phenyl C$_{1-4}$ alkyl group and
    (c) a phenyl C$_{1-4}$ alkoxycarbonyl group),
      a prodrug thereof or a pharmaceutically acceptable salt thereof.

4. The azole compound of claim 3, wherein W is a sulfur atom and m is 0 or 1, a prodrug thereof or a pharmaceutically acceptable salt thereof.

5. The azole compound of claim 4, wherein A is —(CH$_2$)$_m$—X— wherein
  X is —N(R$^8$)— wherein R$^8$ is a hydrogen atom or a C$_{1-6}$ alkyl group, wherein said C$_{1-6}$ alkyl group is optionally substituted by a substituent selected from the group consisting of a C$_{1-4}$ alkoxy group, an aryloxy group, —N(R$^{11}$)(R$^{12}$) (R$^{11}$ and R$^{12}$ are each independently a hydrogen atom or a C$_{1-4}$ alkyl group or may form, together with a nitrogen atom bonded thereto, a 5- to 7-membered hetero ring optionally further having at least one hetero atom selected from the group consisting of nitrogen atom, oxygen atom and sulfur atom), a carboxy group, a C$_{3-7}$ cycloalkyl group and an optionally substituted aryl group, and
  m is 0 or 1,
a prodrug thereof or a pharmaceutically acceptable salt thereof.

6. The azole compound of claim 5, wherein R is —X$^1$-A$^1$-COOR$^7$ wherein each symbol is as defined in claim 3, a prodrug thereof or a pharmaceutically acceptable salt thereof.

7. The azole compound of claim 5, wherein R is —COOR$^7$ wherein R$^7$ is a hydrogen atom,
a prodrug thereof or a pharmaceutically acceptable salt thereof.

8. The azole compound of claim 7, wherein R$^1$, R$^2$, R$^3$ and R$^4$ are hydrogen atoms,
a prodrug thereof or a pharmaceutically acceptable salt thereof.

9. The azole compound of claim 8, wherein B is a phenyl group, a thiazolyl group, a pyridyl group, a benzothiazolyl group, a benzoimidazolyl group or a benzoxazolyl group,
a prodrug thereof or a pharmaceutically acceptable salt thereof.

10. The azole compound of claim 9, wherein B is a phenyl group,
a prodrug thereof or a pharmaceutically acceptable salt thereof.

11. The azole compound of claim 10, wherein R$^5$ is a hydrogen atom,
a prodrug thereof or a pharmaceutically acceptable salt thereof.

12. The azole compound of claim 11, wherein, for R$^6$, Z is
  (1) a C$_{3-7}$ cycloalkyl group
(wherein said C$_{3-7}$ cycloalkyl group is optionally substituted by a phenyl group),
  (2) an aryl group
(wherein said aryl group is optionally substituted by a substituent selected from the group consisting of
    (a) a heterocyclic group optionally substituted by a C$_{1-4}$ alkyl group or a C$_{1-4}$ alkylcarbonyl group,
    (b) a C$_{3-7}$ cycloalkyl group optionally substituted by a substituent selected from the group consisting of a hydroxyl group, an oxo group, a halogen atom and a C$_{1-4}$ alkyl group,
    (c) a carboxy group,
    (d) a halogen atom,
    (e) a C$_{1-8}$ alkyl group,
    (f) a C$_{1-4}$ haloalkyl group,
    (g) a C$_{1-4}$ alkylamino group,
    (h) a di(C$_{1-4}$ alkyl)amino group,
    (i) a C$_{1-4}$ alkylthio group and
    (j) a C$_{1-4}$ alkoxy group) or
  (3) an aromatic heterocyclic group (wherein said aromatic heterocyclic group is optionally substituted by a substituent selected from the group consisting of
  (a) a heterocyclic group,
  (b) a $C_{1-4}$ alkyl group and
  (c) a phenyl group optionally substituted by a halogen atom or a $C_{1-4}$ haloalkyl group),
a prodrug thereof or a pharmaceutically acceptable salt thereof.

13. The azole compound of claim 12, wherein Z is an aryl group optionally substituted by a substituent selected from the group consisting of
  (a) a heterocyclic group optionally substituted by a $C_{1-4}$ alkyl group or a $C_{1-4}$ alkylcarbonyl group,
  (b) a $C_{3-7}$ cycloalkyl group optionally substituted by a substituent selected from the group consisting of a hydroxyl group, an oxo group, a halogen atom and a $C_{1-4}$ alkyl group,
  (c) a carboxy group,
  (d) a halogen atom,
  (e) a $C_{1-8}$ alkyl group,
  (f) a $C_{1-4}$ haloalkyl group,
  (g) a $C_{1-4}$ alkylamino group,
  (h) a di($C_{1-4}$ alkyl)amino group,
  (i) a $C_{1-4}$ alkylthio group and
  (j) a $C_{1-4}$ alkoxy group,
a prodrug thereof or a pharmaceutically acceptable salt thereof.

14. The azole compound of claim 13, wherein Z is a phenyl group substituted by a substituent selected from the group consisting of
  (a) a cyclohexyl group or a cyclopentyl group optionally substituted by a substituent selected from the group consisting of a hydroxyl group, an oxo group, a halogen atom and a $C_{1-4}$ alkyl group,
  (b) a heterocyclic group optionally substituted by a $C_{1-4}$ alkyl group or a $C_{1-4}$ alkylcarbonyl group (wherein said heterocyclic group is selected from the group consisting of a piperidinyl group, a morpholinyl group, a piperazinyl group, a tetrahydropyranyl group, a pyrrolidinyl group and a pyrrolyl group) and
  (c) a $C_{1-8}$ alkyl group,
a prodrug thereof or a pharmaceutically acceptable salt thereof.

15. The azole compound of claim 14, wherein Z is a phenyl group substituted by a cyclohexyl group optionally substituted by a substituent selected from the group consisting of a hydroxyl group, an oxo group, a halogen atom and a $C_{1-4}$ alkyl group,
a prodrug thereof or a pharmaceutically acceptable salt thereof.

16. The azole compound of claim 13 wherein, for $R^{16}$, Y is —O—, —N($R^{13}$)— or —N($R^{14}$)—CO—
wherein
  $R^{13}$ is a hydrogen atom, a $C_{1-4}$ alkyl group or a $C_{2-4}$ alkenyl group, wherein said $C_{1-4}$ alkyl group is optionally substituted by a substituent selected from the group consisting of a $C_{3-7}$ cycloalkyl group, an optionally substituted aryl group, an optionally substituted heterocyclic group and a hydroxyl group,
  $R^{14}$ is a hydrogen atom or a $C_{1-4}$ alkyl group, and s1 is 1,
a prodrug thereof or a pharmaceutically acceptable salt thereof.

17. The azole compound of claim 16, wherein, for $R^6$, $A^2$ is a methylene group,
a prodrug thereof or a pharmaceutically acceptable salt thereof.

18. A pharmaceutical composition comprising an azole compound of claim 1, a prodrug thereof or a pharmaceutically acceptable salt thereof, and a pharmaceutically acceptable carrier.

19. A pharmaceutical composition for inhibiting protein Tyrosine Phosphatase 1B, which comprises an azole compound of claim 1, a prodrug thereof or a pharmaceutically acceptable salt thereof, and a pharmaceutically acceptable carrier.

20. A pharmaceutical composition for treating diabetes, which comprises an azole compound of claim 1, a prodrug thereof or a pharmaceutically acceptable salt thereof, and a pharmaceutically acceptable carrier.

21. A pharmaceutical composition for treating hyperlipidemia, which comprises an azole compound of claim 1, a prodrug thereof or a pharmaceutically acceptable salt thereof, and a pharmaceutically acceptable carrier.

22. The pharmaceutical composition of claim 18, which is used in combination with a different therapeutic drug for hyperlipidemia.

23. The pharmaceutical composition of claim 22, wherein the therapeutic drug for hyperlipidemia is a statin pharmaceutical agent.

24. The pharmaceutical composition of claim 23, wherein the statin pharmaceutical agent is selected from the group consisting of lovastatin, simvastatin, pravastatin, fluvastatin, atorvastatin and cerivastatin.

25. The pharmaceutical composition of claim 18, which is used in combination with a different therapeutic drug for diabetes.

26. The pharmaceutical composition of claim 25, which is used in combination with a therapeutic agent for diabetes selected from the group consisting of an insulin secretagogue, a sulfonylurea, a sulfonamide, a biguanide, an α glucosidase inhibitor, an insulin preparation and an insulin sensitizer.

27. The pharmaceutical composition of claim 26, wherein the therapeutic agent for diabetes is selected from the group consisting of nateglide, glimepiride, glibenclamide, gliclazide, acetohexamide, tolbutamide, glyclopyramide, tolazamide, glybuzole, metformin hydrochloride, buformin hydrochloride, voglibose, acarbose, insulin and pioglitazone hydrochloride.

28. The pharmaceutical composition of claim 20, which is used in combination with a different therapeutic drug for hyperlipidemia.

29. The pharmaceutical composition of claim 28, wherein the therapeutic drug for hyperlipidemia is a statin pharmaceutical agent.

30. The pharmaceutical composition of claim 29, wherein the statin pharmaceutical agent is selected from the group consisting of lovastatin, simvastatin, pravastatin, fluvastatin, atorvastatin and cerivastatin.

31. The pharmaceutical composition of claim 20, which is used in combination with a different therapeutic drug for diabetes.

32. The pharmaceutical composition of claim 31, which is used in combination with a therapeutic drug for diabetes selected from the group consisting of an insulin secretagogue, a sulfonylurea, a sulfonamide, a biguanide, an α glucosidase inhibitor, an insulin preparation and an insulin sensitizer.

33. The pharmaceutical composition of claim 32, wherein the therapeutic agent for diabetes is selected from the group consisting of nateglide, glimepiride, glibenclamide, gliclazide, acetohexamide, tolbutamide, glyclopyramide, tolazamide, glybuzole, metformin hydrochloride, buformin hydrochloride, voglibose, acarbose, insulin and pioglitazone hydrochloride.

34. The pharmaceutical composition of claim 21, which is used in combination with a different therapeutic drug for hyperlipidemia.

35. The pharmaceutical composition of claim 34, wherein the therapeutic drug for hyperlipidemia is a statin pharmaceutical agent.

36. The pharmaceutical composition of claim 35, wherein the statin pharmaceutical agent is selected from the group consisting of lovastatin, simvastatin, pravastatin, fluvastatin, atorvastatin and cerivastatin.

37. The pharmaceutical composition of claim 21, which is used in combination with a different therapeutic drug for diabetes.

38. The pharmaceutical composition of claim 37, which is used in combination with a therapeutic drug for diabetes selected from the group consisting of an insulin secretagogue, a sulfonylurea, a sulfonamide, a biguanide, an α glucosidase inhibitor, an insulin preparation and an insulin sensitizer.

39. The pharmaceutical composition of claim 38, wherein the therapeutic agent for diabetes is selected from the group consisting of nateglide, glimepiride, glibenclamide, gliclazide, acetohexamide, tolbutamide, glyclopyramide, tolazamide, glybuzole, metformin hydrochloride, buformin hydrochloride, voglibose, acarbose, insulin and pioglitazone hydrochloride.

40. A method of inhibiting protein Tyrosine Phosphatase 1B, which comprises administering an effective amount of an azole compound of claim 1, a prodrug thereof or a pharmaceutically acceptable salt thereof to a mammal.

41. A method of treating diabetes, which comprises administering an effective amount of an azole compound of claim 1, a prodrug thereof or a pharmaceutically acceptable salt thereof to a mammal.

42. A method of treating hyperlipidemia, which comprises administering an effective amount of an azole compound of claim 1, a prodrug thereof or a pharmaceutically acceptable salt thereof to a mammal.

43. Use of an azole compound of claim 1, a prodrug thereof or a pharmaceutically acceptable salt thereof for the production of a protein tyrosine phosphatase 1B inhibitor.

44. Use of an azole compound of claim 1, a prodrug thereof or a pharmaceutically acceptable salt thereof for the production of a therapeutic agent for diabetes.

45. Use of an azole compound of claim 1, a prodrug thereof or a pharmaceutically acceptable salt thereof for the production of a therapeutic agent for hyperlipidemia.

46. A commercial package comprising the pharmaceutical composition of claim 18 and a written matter associated therewith, the written matter stating that said pharmaceutical composition can or should be used for inhibiting protein Tyrosine Phosphatase 1B.

47. A commercial package comprising the pharmaceutical composition of claim 18 and a written matter associated therewith, the written matter stating that said pharmaceutical composition can or should be used for treating diabetes.

48. A commercial package comprising the pharmaceutical composition of claim 18 and a written matter associated therewith, the written matter stating that said pharmaceutical composition can or should be used for treating hyperlipidemia.

49. A method of treating hyperlipidemia, which comprises administering an effective amount of an azole compound of claim 1, a prodrug thereof or a pharmaceutically acceptable salt thereof to a mammal, and administering an effective amount of a different therapeutic drug for hyperlipidemia to said mammal.

50. The method of treating of claim 49, wherein the therapeutic drug for hyperlipidemia is a statin pharmaceutical agent.

51. The method of treating of claim 50, wherein the statin pharmaceutical agent is selected from the group consisting of lovastatin, simvastatin, pravastatin, fluvastatin, atorvastatin and cerivastatin.

52. A method of treating diabetes, which comprises administering an effective amount of an azole compound of claim 1, a prodrug thereof or a pharmaceutically acceptable salt thereof to a mammal, and administering an effective amount of a different therapeutic agent for diabetes to said mammal.

53. The method of treating of claim 52, wherein the therapeutic agent for diabetes is selected from the group consisting of an insulin secretagogue, a sulfonylurea, a sulfonamide, a biguanide, an α glucosidase inhibitor, an insulin preparation and an insulin sensitizer.

54. The method of treating of claim 53, wherein the therapeutic agent for diabetes is selected from the group consisting of nateglide, glimepiride, glibenclamide, gliclazide, acetohexamide, tolbutamide, glyclopyramide, tolazamide, glybuzole, metformin hydrochloride, buformin hydrochloride, voglibose, acarbose, insulin and pioglitazone hydrochloride.

* * * * *